(12) United States Patent
Childs et al.

(10) Patent No.: US 11,540,891 B2
(45) Date of Patent: Jan. 3, 2023

(54) ACCESSORY SUPPORT AND COUPLING SYSTEMS FOR AN ACCESSORY SUPPORT

(71) Applicant: Stryker Corporation, Kalamazoo, MI (US)

(72) Inventors: William D. Childs, Plainwell, MI (US); Brian J. Tessmer, Mattawan, MI (US); Connor F. St. John, Kalamazoo, MI (US); Krishna Sandeep Bhimavarapu, Kalamazoo, MI (US); Isaac A. Schaberg, Kalamazoo, MI (US); Zachary J. Sadler, South Lyon, MI (US); Kirby M. Neihouser, Francesville, IN (US)

(73) Assignee: Stryker Corporation, Kalamazoo, MI (US)

(*) Notice: Subject to any disclaimer, the term of this patent is extended or adjusted under 35 U.S.C. 154(b) by 84 days.

(21) Appl. No.: 17/226,425

(22) Filed: Apr. 9, 2021

(65) Prior Publication Data
US 2021/0220071 A1 Jul. 22, 2021

Related U.S. Application Data

(63) Continuation of application No. 16/782,163, filed on Feb. 5, 2020, now Pat. No. 11,000,340, which is a
(Continued)

(51) Int. Cl.
*H02B 1/04* (2006.01)
*A61G 12/00* (2006.01)
(Continued)

(52) U.S. Cl.
CPC ............ *A61B 50/26* (2016.02); *A61B 5/02* (2013.01); *A61B 50/13* (2016.02); *A61B 90/50* (2016.02);
(Continued)

(58) Field of Classification Search
None
See application file for complete search history.

(56) References Cited

U.S. PATENT DOCUMENTS

| 277,374 A | 5/1883 | Strohm |
| 289,164 A | 11/1883 | Strohm |

(Continued)

FOREIGN PATENT DOCUMENTS

| AU | 2012211373 A1 | 3/2013 |
| CA | 2461209 A1 | 9/2004 |

(Continued)

OTHER PUBLICATIONS

English language abstract and machine-assisted English translation for KR 2013-0076922 extracted from espacenet.com database on May 2, 2018, 8 pages.
(Continued)

*Primary Examiner* — Courtney L Smith
(74) *Attorney, Agent, or Firm* — Howard & Howard Attorneys PLLC

(57) ABSTRACT

The present disclosure provides a coupling system for coupling a medical accessory to an accessory support is provided. The present disclosure also provides a system for powering a medical accessory with an accessory support.

16 Claims, 40 Drawing Sheets

Related U.S. Application Data continuation of application No. 15/422,979, filed on Feb. 2, 2017, now Pat. No. 10,582,981.

(60) Provisional application No. 62/314,561, filed on Mar. 29, 2016, provisional application No. 62/290,244, filed on Feb. 2, 2016.

(51) Int. Cl.

| | | |
|---|---|---|
| *A61B 50/26* | (2016.01) | |
| *A61G 7/05* | (2006.01) | |
| *A61G 5/10* | (2006.01) | |
| *A61M 5/14* | (2006.01) | |
| *H01R 13/639* | (2006.01) | |
| *H02B 1/26* | (2006.01) | |
| *H01R 13/627* | (2006.01) | |
| *A61B 90/50* | (2016.01) | |
| *A61B 50/13* | (2016.01) | |
| *A61B 90/57* | (2016.01) | |
| *A61B 5/02* | (2006.01) | |
| *H02B 1/056* | (2006.01) | |
| *H02B 1/052* | (2006.01) | |
| *A61G 13/10* | (2006.01) | |

(52) U.S. Cl.
CPC ............... *A61B 90/57* (2016.02); *A61G 5/10* (2013.01); *A61G 7/0503* (2013.01); *A61G 12/008* (2013.01); *A61M 5/1415* (2013.01); *H01R 13/6275* (2013.01); *H01R 13/639* (2013.01); *H02B 1/26* (2013.01); *A61B 2090/508* (2016.02); *A61B 2090/571* (2016.02); *A61G 13/107* (2013.01); *A61G 2203/78* (2013.01); *A61G 2203/80* (2013.01); *A61M 2205/82* (2013.01); *A61M 2205/8237* (2013.01); *H02B 1/04* (2013.01); *H02B 1/052* (2013.01); *H02B 1/0565* (2013.01)

(56) References Cited

U.S. PATENT DOCUMENTS

| | | |
|---|---|---|
| 450,378 A | 4/1891 | Robinson |
| 1,342,001 A | 6/1920 | Schulte |
| 2,289,164 A | 7/1942 | Strohm |
| D140,317 S | 2/1945 | Allen |
| 2,397,291 A | 3/1946 | Robertson |
| 2,790,570 A | 4/1957 | Hodges et al. |
| 2,888,546 A | 5/1959 | Kinney |
| 2,902,821 A | 9/1959 | Kelly, Jr. |
| 2,983,014 A | 5/1961 | Greenwood |
| 3,123,879 A | 3/1964 | Boduroff et al. |
| 3,132,822 A | 5/1964 | Arthur |
| 3,136,515 A | 6/1964 | Potruch |
| 3,308,703 A | 3/1967 | Sauer |
| 3,363,216 A | 1/1968 | Benedetto |
| 3,576,304 A | 4/1971 | Gillemot et al. |
| 3,676,900 A | 7/1972 | De Valenzuela |
| 4,023,757 A | 5/1977 | Allard et al. |
| 4,120,304 A | 10/1978 | Moor |
| 4,244,544 A | 1/1981 | Komat |
| 4,332,378 A | 6/1982 | Pryor |
| 4,352,991 A | 10/1982 | Kaufman |
| 4,511,157 A | 4/1985 | Wilt, Jr. |
| 4,511,158 A | 4/1985 | Varga et al. |
| 4,572,536 A | 2/1986 | Doughty |
| 4,584,989 A | 4/1986 | Stith |
| 4,600,209 A | 7/1986 | Kerr, Jr. |
| 4,659,279 A | 4/1987 | Akeel et al. |
| 4,715,571 A | 12/1987 | Soltow et al. |
| 4,725,027 A | 2/1988 | Bekanich |
| 4,756,706 A | 7/1988 | Kerns et al. |
| 4,767,131 A | 8/1988 | Springer et al. |
| 4,768,241 A | 9/1988 | Beney |
| 4,832,294 A | 5/1989 | Eidem |
| 4,840,391 A | 6/1989 | Schneider |
| 4,886,237 A | 12/1989 | Dennis |
| 4,892,279 A | 1/1990 | Lafferty et al. |
| 4,898,578 A | 2/1990 | Rubalcaba, Jr. |
| 4,905,944 A | 3/1990 | Jost et al. |
| D308,933 S | 7/1990 | Hube et al. |
| 4,945,592 A | 8/1990 | Sims et al. |
| 4,966,340 A | 10/1990 | Hunter |
| 4,969,768 A | 11/1990 | Young |
| 4,971,271 A | 11/1990 | Sularz |
| 5,009,442 A | 4/1991 | Schneider |
| 5,027,478 A | 7/1991 | Suhr |
| 5,046,899 A | 9/1991 | Nishi |
| 5,077,843 A | 1/1992 | Dale et al. |
| 5,083,807 A | 1/1992 | Bobb et al. |
| 5,110,076 A | 5/1992 | Snyder et al. |
| 5,112,019 A | 5/1992 | Metzler et al. |
| 5,117,521 A | 6/1992 | Foster et al. |
| 5,125,607 A | 6/1992 | Pryor |
| 5,135,191 A | 8/1992 | Schmuhl |
| 5,149,036 A | 9/1992 | Sheehan |
| 5,172,927 A | 12/1992 | Bobb et al. |
| 5,186,337 A | 2/1993 | Foster et al. |
| 5,188,323 A | 2/1993 | David |
| D333,933 S | 3/1993 | Feinbloom |
| 5,219,139 A | 6/1993 | Hertzler et al. |
| 5,236,213 A | 8/1993 | Trickett |
| D340,942 S | 11/1993 | Smith |
| 5,284,255 A | 2/1994 | Foster et al. |
| 5,288,093 A | 2/1994 | Gross |
| 5,292,094 A | 3/1994 | VanKuiken |
| 5,309,604 A | 5/1994 | Poulsen |
| 5,316,246 A | 5/1994 | Scott et al. |
| 5,319,816 A | 6/1994 | Ruehl |
| 5,323,992 A | 6/1994 | Sifers et al. |
| 5,332,184 A | 7/1994 | Davis |
| 5,335,651 A | 8/1994 | Foster et al. |
| 5,337,992 A | 8/1994 | Pryor et al. |
| 5,355,539 A | 10/1994 | Boettger |
| 5,374,074 A | 12/1994 | Smith |
| 5,385,324 A | 1/1995 | Pryor et al. |
| 5,396,673 A | 3/1995 | Foster |
| 5,398,359 A | 3/1995 | Foster |
| D358,545 S | 5/1995 | Price |
| 5,421,548 A | 6/1995 | Bennett et al. |
| 5,455,975 A * | 10/1995 | Foster ................ A61G 12/004 5/658 |
| 5,457,831 A | 10/1995 | Foster et al. |
| 5,458,305 A | 10/1995 | Woodward |
| 5,475,884 A | 12/1995 | Kirmse et al. |
| 5,479,953 A | 1/1996 | Pasulka |
| 5,481,939 A | 1/1996 | Bernardini |
| 5,509,680 A | 4/1996 | Scharf et al. |
| 5,513,406 A | 5/1996 | Foster et al. |
| 5,527,289 A | 6/1996 | Foster et al. |
| 5,532,184 A | 7/1996 | Kato |
| D372,419 S | 8/1996 | Ikegami |
| 5,551,105 A | 9/1996 | Short |
| 5,556,065 A | 9/1996 | Wadley |
| 5,566,676 A | 10/1996 | Rosenfeldt et al. |
| 5,624,403 A | 4/1997 | Jaquith |
| 5,644,876 A | 7/1997 | Walker |
| 5,647,491 A | 7/1997 | Foster et al. |
| 5,687,717 A | 11/1997 | Halpern et al. |
| 5,699,988 A | 12/1997 | Boettger et al. |
| 5,702,845 A | 12/1997 | Kawakami et al. |
| 5,704,577 A | 1/1998 | Gordon |
| 5,742,982 A | 4/1998 | Dodd et al. |
| 5,771,511 A | 6/1998 | Kummer et al. |
| D395,815 S | 7/1998 | Walters et al. |
| 5,784,542 A * | 7/1998 | Ohm .................... A61B 34/35 901/34 |
| 5,820,086 A | 10/1998 | Hoftman et al. |
| 5,857,685 A | 1/1999 | Phillips et al. |
| 5,890,687 A | 4/1999 | Pryor et al. |
| 5,892,177 A | 4/1999 | Mazaris |
| 5,898,961 A | 5/1999 | Ambach et al. |

(56) References Cited

U.S. PATENT DOCUMENTS

| | | | |
|---|---|---|---|
| 5,901,930 A | 5/1999 | Harrel | |
| 5,924,658 A | 7/1999 | Shiery et al. | |
| 5,957,352 A | 9/1999 | Gares | |
| 5,966,760 A | 10/1999 | Gallant et al. | |
| 5,987,670 A | 11/1999 | Sims et al. | |
| 5,991,947 A | 11/1999 | Lavin et al. | |
| D419,674 S | 1/2000 | Schattner | |
| 6,012,940 A | 1/2000 | Wheeler | |
| 6,056,249 A | 5/2000 | Fillon, Jr. | |
| 6,073,285 A | 6/2000 | Ambach et al. | |
| 6,079,678 A | 6/2000 | Schott et al. | |
| D428,325 S | 7/2000 | van Dreumel et al. | |
| 6,095,468 A * | 8/2000 | Chirico | F16M 11/2014 248/125.7 |
| 6,179,260 B1 | 1/2001 | Ohanian | |
| 6,183,417 B1 | 2/2001 | Geheb et al. | |
| 6,186,977 B1 | 2/2001 | Andrews et al. | |
| 6,227,502 B1 | 5/2001 | Derman | |
| 6,230,710 B1 | 5/2001 | Sobko et al. | |
| 6,351,678 B1 | 2/2002 | Borders | |
| 6,360,051 B1 | 3/2002 | Daoud | |
| 6,360,389 B1 | 3/2002 | Gallant et al. | |
| 6,390,311 B1 | 5/2002 | Belokin | |
| 6,458,104 B2 | 10/2002 | Gautsche | |
| 6,552,270 B1 | 4/2003 | Heacox | |
| 6,585,206 B2 | 7/2003 | Metz et al. | |
| 6,619,599 B2 | 9/2003 | Elliott et al. | |
| 6,704,956 B2 | 3/2004 | Riley et al. | |
| 6,708,991 B1 | 3/2004 | Ortlieb | |
| 6,710,249 B1 | 3/2004 | Denton | |
| 6,725,483 B2 * | 4/2004 | Gallant | A61G 7/05 5/503.1 |
| 6,752,360 B2 | 6/2004 | Bennett | |
| 6,801,704 B1 | 10/2004 | Daoud et al. | |
| 6,899,103 B1 | 5/2005 | Hood et al. | |
| 6,965,932 B1 | 11/2005 | Rajaram et al. | |
| 6,966,086 B2 | 11/2005 | Metz et al. | |
| 6,969,031 B2 | 11/2005 | Ugent et al. | |
| 6,993,799 B2 | 2/2006 | Foster et al. | |
| 7,017,208 B2 | 3/2006 | Weismiller et al. | |
| 7,065,811 B2 | 6/2006 | Newkirk et al. | |
| 7,065,812 B2 | 6/2006 | Newkirk et al. | |
| D526,885 S | 8/2006 | Kelleghan | |
| 7,083,150 B2 | 8/2006 | Newkirk et al. | |
| 7,154,397 B2 | 12/2006 | Zerhusen et al. | |
| 7,216,382 B2 | 5/2007 | Newkirk et al. | |
| 7,237,287 B2 | 7/2007 | Weismiller et al. | |
| 7,303,568 B2 | 12/2007 | Jannot | |
| D559,080 S | 1/2008 | Boote | |
| 7,314,200 B2 | 1/2008 | Bally et al. | |
| 7,320,681 B2 | 1/2008 | Gillis et al. | |
| D568,722 S | 5/2008 | King | |
| 7,394,963 B2 | 7/2008 | Hartlef | |
| 7,418,749 B2 | 9/2008 | Graham et al. | |
| 7,451,506 B2 | 11/2008 | Kummer et al. | |
| 7,480,951 B2 | 1/2009 | Weismiller et al. | |
| D587,101 S | 2/2009 | Morgan | |
| D587,102 S | 2/2009 | Morgan | |
| 7,497,407 B2 | 3/2009 | Blankenship et al. | |
| 7,500,644 B2 | 3/2009 | Naudet et al. | |
| 7,533,428 B2 | 5/2009 | Yunker | |
| 7,556,226 B2 | 7/2009 | Muncie | |
| D597,403 S | 8/2009 | Ho et al. | |
| 7,570,152 B2 | 8/2009 | Smith et al. | |
| 7,624,463 B2 | 12/2009 | Graham et al. | |
| 7,624,953 B2 | 12/2009 | Silverman et al. | |
| 7,636,966 B2 | 12/2009 | Gallant et al. | |
| 7,637,464 B2 | 12/2009 | Heimbrock et al. | |
| 7,641,158 B2 | 1/2010 | Ferguson | |
| 7,680,605 B2 | 3/2010 | Yung et al. | |
| D613,412 S | 4/2010 | DeCarlo | |
| 7,715,387 B2 | 5/2010 | Schuman | |
| 7,731,136 B1 | 6/2010 | Chisolm et al. | |
| 7,735,788 B2 | 6/2010 | Newkirk et al. | |
| 7,735,789 B2 | 6/2010 | Blankenship et al. | |
| D619,940 S | 7/2010 | Strang | |
| D620,781 S | 8/2010 | Weckworth | |
| 7,793,902 B2 | 9/2010 | Buchanan et al. | |
| 7,802,764 B2 | 9/2010 | Leinen | |
| D628,218 S | 11/2010 | Tommassini | |
| 7,831,447 B2 | 11/2010 | Schuman | |
| 7,845,601 B1 | 12/2010 | Culpepper et al. | |
| 7,865,983 B2 | 1/2011 | Newkirk et al. | |
| 7,874,410 B2 | 1/2011 | Fulbrook et al. | |
| 7,884,735 B2 | 2/2011 | Newkirk | |
| 7,896,298 B2 | 3/2011 | Meyers et al. | |
| 7,911,349 B2 | 3/2011 | Zerhusen et al. | |
| 7,918,422 B2 | 4/2011 | Blankenship et al. | |
| 7,921,489 B2 * | 4/2011 | Newkirk | A61G 7/1076 248/326 |
| 7,933,669 B2 | 4/2011 | Rawls-Meehan | |
| D638,690 S | 5/2011 | Hoek | |
| D638,691 S | 5/2011 | Hoek | |
| D638,692 S | 5/2011 | Hoek | |
| D639,145 S | 6/2011 | Hoek | |
| D639,146 S | 6/2011 | Hoek | |
| D640,527 S | 6/2011 | Hoek | |
| 7,979,136 B2 | 7/2011 | Young et al. | |
| D644,501 S | 9/2011 | Chen | |
| 8,056,162 B2 | 11/2011 | Newkirk et al. | |
| 8,075,513 B2 | 12/2011 | Rudko et al. | |
| 8,082,160 B2 | 12/2011 | Collins, Jr. et al. | |
| 8,082,857 B2 | 12/2011 | George et al. | |
| 8,100,371 B2 | 1/2012 | Eggleston et al. | |
| 8,104,729 B2 | 1/2012 | Walke et al. | |
| 8,117,701 B2 | 2/2012 | Bobey et al. | |
| D655,598 S | 3/2012 | Hsu | |
| 8,136,773 B2 | 3/2012 | Schmutzer et al. | |
| D657,869 S | 4/2012 | Mammen | |
| 8,152,181 B2 | 4/2012 | Tomlinson | |
| 8,156,582 B2 | 4/2012 | Rupar et al. | |
| 8,166,585 B2 | 5/2012 | Settgast et al. | |
| 8,191,909 B2 | 6/2012 | Livengood et al. | |
| 8,196,874 B2 | 6/2012 | Zitting et al. | |
| 8,240,620 B2 | 8/2012 | Walter | |
| 8,258,973 B2 | 9/2012 | Newkirk | |
| 8,292,310 B2 | 10/2012 | Turner | |
| 8,292,656 B2 | 10/2012 | Mydlarz | |
| 8,313,066 B2 | 11/2012 | Hampton et al. | |
| 8,313,067 B2 | 11/2012 | Knieriem et al. | |
| 8,314,781 B2 | 11/2012 | Pittenger et al. | |
| 8,334,779 B2 | 12/2012 | Zerhusen et al. | |
| D674,271 S | 1/2013 | Rodwin | |
| 8,344,246 B2 | 1/2013 | Lipiansky et al. | |
| 8,360,975 B1 | 1/2013 | Schwieterman et al. | |
| 8,361,040 B2 | 1/2013 | Spohn et al. | |
| 8,370,977 B2 | 2/2013 | Newkirk et al. | |
| 8,403,275 B2 | 3/2013 | Cote | |
| D680,419 S | 4/2013 | Green et al. | |
| 8,421,635 B2 | 4/2013 | Liu et al. | |
| 8,452,413 B2 | 5/2013 | Young et al. | |
| 8,511,468 B2 | 8/2013 | Reeves et al. | |
| 8,516,637 B2 | 8/2013 | Karwal et al. | |
| 8,534,616 B2 | 9/2013 | Schmutzer et al. | |
| D691,873 S | 10/2013 | Ganski | |
| D691,874 S | 10/2013 | Ganski | |
| D691,875 S | 10/2013 | Ganski | |
| D691,876 S | 10/2013 | Ganski | |
| D691,877 S | 10/2013 | Ganski | |
| 8,567,730 B1 | 10/2013 | Stevenson | |
| 8,618,918 B2 | 12/2013 | Tallent et al. | |
| 8,657,241 B2 | 2/2014 | Zitting et al. | |
| D701,448 S | 3/2014 | Rodwin | |
| 8,672,842 B2 | 3/2014 | Kenalty et al. | |
| 8,674,839 B2 | 3/2014 | Zerhusen et al. | |
| 8,684,375 B2 | 4/2014 | Fink et al. | |
| 8,689,798 B2 | 4/2014 | Sabin | |
| 8,707,515 B2 | 4/2014 | Payne et al. | |
| 8,733,719 B2 | 5/2014 | Gaal et al. | |
| 8,740,301 B2 | 6/2014 | Liu | |
| 8,747,764 B1 | 6/2014 | Burchman et al. | |
| 8,752,220 B2 | 6/2014 | Soderberg et al. | |
| 8,752,799 B2 | 6/2014 | Johnson | |
| 8,756,078 B2 | 6/2014 | Collins, Jr. et al. | |

(56) References Cited

U.S. PATENT DOCUMENTS

| | | |
|---|---|---|
| RE45,058 E | 8/2014 | Blankenship et al. |
| 8,814,792 B2 | 8/2014 | Raptis et al. |
| 8,826,475 B2 | 9/2014 | Jackson |
| 8,827,215 B2 | 9/2014 | Hilton |
| 8,843,832 B2 | 9/2014 | Frields et al. |
| 8,857,920 B2 | 10/2014 | Wollborg |
| 8,864,205 B2 | 10/2014 | Lemire et al. |
| D719,013 S | 12/2014 | St. John et al. |
| 8,953,308 B2 | 2/2015 | Riley et al. |
| 8,998,151 B2 | 4/2015 | Hoek |
| 9,033,349 B2 | 5/2015 | Graves et al. |
| 9,044,361 B2 | 6/2015 | Bell et al. |
| 9,259,369 B2 | 2/2016 | Derenne et al. |
| 9,289,336 B2 | 3/2016 | Lambarth et al. |
| 9,320,444 B2 | 4/2016 | Hayes et al. |
| 9,330,046 B2 | 5/2016 | Keegan et al. |
| 9,528,536 B2 | 12/2016 | Bally et al. |
| 9,569,591 B2 | 2/2017 | Vanderpohl, III |
| 10,278,827 B2 | 5/2019 | Drury et al. |
| 10,582,981 B2 | 3/2020 | Childs et al. |
| 2002/0036184 A1 | 3/2002 | Sohn |
| 2002/0044059 A1 | 4/2002 | Reeder et al. |
| 2002/0096608 A1 | 7/2002 | Cedarberg |
| 2002/0134570 A1 | 9/2002 | Franklin-Lees |
| 2002/0152555 A1* | 10/2002 | Gallant ............... A61G 7/05 5/658 |
| 2003/0132352 A1 | 7/2003 | Weaver |
| 2004/0011941 A1 | 1/2004 | Roepke et al. |
| 2004/0075228 A1 | 4/2004 | Duffey |
| 2004/0118982 A1 | 6/2004 | Shillings et al. |
| 2004/0164220 A1* | 8/2004 | Newkirk ............... A61M 16/12 248/647 |
| 2004/0186358 A1 | 9/2004 | Chernow et al. |
| 2004/0201191 A1 | 10/2004 | Jacques et al. |
| 2005/0006534 A1 | 1/2005 | Shillings |
| 2005/0006538 A1 | 1/2005 | Turi et al. |
| 2005/0017468 A1 | 1/2005 | Gallant et al. |
| 2005/0077436 A1 | 4/2005 | Nelson |
| 2005/0139736 A1 | 6/2005 | Breda et al. |
| 2005/0189453 A1 | 9/2005 | DeGuevara |
| 2005/0230575 A1 | 10/2005 | Zelenski et al. |
| 2006/0031989 A1 | 2/2006 | Graham et al. |
| 2006/0036184 A1 | 2/2006 | Tenzer et al. |
| 2006/0179571 A1* | 8/2006 | Newkirk ............... A61G 13/107 5/503.1 |
| 2006/0207026 A1 | 9/2006 | Newkirk et al. |
| 2006/0235283 A1 | 10/2006 | Vinarov et al. |
| 2006/0237597 A1 | 10/2006 | D'Andria |
| 2006/0249635 A1 | 11/2006 | Newkirk et al. |
| 2007/0018058 A1 | 1/2007 | Graham et al. |
| 2007/0097601 A1* | 5/2007 | Hughes ............... H01R 13/53 361/600 |
| 2007/0120023 A1 | 5/2007 | Martinez et al. |
| 2007/0135866 A1 | 6/2007 | Baker et al. |
| 2007/0137371 A1* | 6/2007 | Devengenzo ......... A61B 34/30 74/490.01 |
| 2007/0159772 A1 | 7/2007 | Morice |
| 2007/0235597 A1 | 10/2007 | Winchester |
| 2007/0246613 A1 | 10/2007 | Kennedy |
| 2008/0004904 A1 | 1/2008 | Tran |
| 2008/0120784 A1 | 5/2008 | Warner et al. |
| 2008/0126132 A1 | 5/2008 | Warner et al. |
| 2008/0234555 A1 | 9/2008 | Lafleche et al. |
| 2008/0263769 A1 | 10/2008 | Newkirk et al. |
| 2009/0065249 A1 | 3/2009 | Silvers |
| 2009/0070472 A1 | 3/2009 | Baldus et al. |
| 2009/0261215 A1 | 10/2009 | Lambert |
| 2009/0262266 A1 | 10/2009 | Harbin |
| 2009/0294604 A1 | 12/2009 | Sunderland |
| 2010/0006711 A1 | 1/2010 | Roth |
| 2010/0117281 A1 | 5/2010 | Doyle |
| 2010/0132979 A1 | 6/2010 | Chen |
| 2010/0212087 A1 | 8/2010 | Leib et al. |
| 2010/0233917 A1 | 9/2010 | Sorensen |
| 2010/0263123 A1 | 10/2010 | Newkirk et al. |
| 2011/0131057 A1* | 6/2011 | Newkirk ............... A61G 13/107 705/2 |
| 2011/0147542 A1 | 6/2011 | Hoek |
| 2011/0153659 A1 | 6/2011 | Postrel |
| 2011/0231996 A1 | 9/2011 | Lemire et al. |
| 2011/0248125 A1 | 10/2011 | D'Andria |
| 2012/0089419 A1 | 4/2012 | Huster et al. |
| 2012/0124746 A1 | 5/2012 | Andrienko et al. |
| 2012/0191474 A1 | 7/2012 | Postrel |
| 2012/0265148 A1 | 10/2012 | Nokes, Jr. et al. |
| 2012/0277682 A1 | 11/2012 | Corato et al. |
| 2012/0284777 A1 | 11/2012 | Eugenio et al. |
| 2013/0037663 A1 | 2/2013 | Walther et al. |
| 2013/0046197 A1 | 2/2013 | Dlugos, Jr. et al. |
| 2013/0091631 A1 | 4/2013 | Hayes et al. |
| 2013/0181100 A1 | 7/2013 | Blankenship et al. |
| 2013/0228997 A1 | 9/2013 | Fukuhara et al. |
| 2013/0283529 A1 | 10/2013 | Hayes et al. |
| 2013/0292521 A1 | 11/2013 | Chepurny |
| 2013/0312691 A1 | 11/2013 | Harada |
| 2013/0318716 A1 | 12/2013 | Vanderpohl, III |
| 2014/0026322 A1 | 1/2014 | Bell et al. |
| 2014/0057463 A1 | 2/2014 | Bhimavarapu et al. |
| 2014/0080413 A1 | 3/2014 | Hayes et al. |
| 2014/0090173 A1 | 4/2014 | DiMaio et al. |
| 2014/0166828 A1 | 6/2014 | Zitting et al. |
| 2014/0201414 A1 | 7/2014 | Keegan et al. |
| 2014/0209530 A1 | 7/2014 | Flansburg et al. |
| 2014/0209550 A1 | 7/2014 | Pryor et al. |
| 2014/0259414 A1 | 9/2014 | Hayes et al. |
| 2014/0259837 A1 | 9/2014 | Belliveau et al. |
| 2014/0265611 A1 | 9/2014 | Fern et al. |
| 2014/0297327 A1 | 10/2014 | Heil et al. |
| 2014/0305995 A1* | 10/2014 | Shelton, IV ......... A61B 17/105 227/180.1 |
| 2014/0306070 A1 | 10/2014 | Hartsock et al. |
| 2014/0312691 A1 | 10/2014 | Doljack et al. |
| 2014/0323816 A1 | 10/2014 | Soderberg et al. |
| 2014/0358917 A1 | 12/2014 | Johnson |
| 2014/0361129 A1 | 12/2014 | Gomez |
| 2014/0367540 A1 | 12/2014 | Gaal et al. |
| 2015/0033295 A1 | 1/2015 | Huster |
| 2015/0034776 A1 | 2/2015 | St.John et al. |
| 2015/0059150 A1 | 3/2015 | Hilton |
| 2015/0157522 A1 | 6/2015 | Blankenship et al. |
| 2015/0216606 A1 | 8/2015 | Bally et al. |
| 2016/0000995 A1 | 1/2016 | Blankenship et al. |
| 2016/0022900 A1 | 1/2016 | Pryor et al. |
| 2016/0080365 A1 | 3/2016 | Baker et al. |
| 2016/0157951 A1 | 6/2016 | Schoenig et al. |
| 2016/0166216 A1 | 6/2016 | Igney et al. |
| 2016/0302982 A1 | 10/2016 | Blankenship et al. |
| 2017/0079434 A1 | 3/2017 | Paul et al. |
| 2020/0170744 A1 | 6/2020 | Childs et al. |

FOREIGN PATENT DOCUMENTS

| | | |
|---|---|---|
| CN | 2461209 Y | 11/2001 |
| CN | 201949145 U | 8/2011 |
| CN | 202376384 U | 8/2012 |
| CN | 202951084 U | 5/2013 |
| EP | 1032350 B1 | 2/2002 |
| EP | 1309304 A2 | 5/2003 |
| EP | 1265660 B1 | 11/2005 |
| EP | 1690517 A2 | 8/2006 |
| EP | 1432375 B1 | 3/2009 |
| EP | 2416822 A1 | 2/2012 |
| KR | 20130076922 A | 7/2013 |
| WO | 0205740 A2 | 1/2002 |
| WO | 2005051278 A1 | 6/2005 |
| WO | 2010030981 A1 | 3/2010 |
| WO | 2010126668 A1 | 11/2010 |
| WO | 2011055173 A1 | 5/2011 |
| WO | 2013078481 A1 | 5/2013 |
| WO | 2015017685 A1 | 2/2015 |
| WO | 2015031394 A1 | 3/2015 |

(56) References Cited

FOREIGN PATENT DOCUMENTS

| WO | 2015106232 A1 | 7/2015 |
|----|---------------|--------|
| WO | 2016167917 A1 | 10/2016 |

OTHER PUBLICATIONS

English language abstract and machine-assisted translation for CN20194145 extracted from espacenet.com Sep. 29, 2017; 4 pages.
English language abstract and machine-assisted translation for CN202376384 extracted from espacenet.com Sep. 29, 2017; 4 pages.
English language abstract and machine-assisted translation for CN2461209 extracted from espacenet.com Oct. 2, 2017; 6 pages.
English language abstract and machine-assisted translation for WO2005051278 extracted from espacenet.com Sep. 29, 2017; 4 pages.
English language abstract for CN202951084 extracted from espacenet.com Sep. 29, 2017; 1 page.
Hill-Rom, "Latitude (R) Arm System, Taking patient care in a new direction", Mar. 2014; 4 pages.
International Search Report and Written Opinon for PCT/US2014/049209 dated Nov. 10, 2014; 8 pages.
IVEA, "IVEA Patient Ambulation Webpage,"http://www.iveamobility.com/, 2018, 6 pages.
Youtube, "IVEA by Firefly Medical Video Preview-Short Version", Oct. 5, 2015, https://www.youtube.com/watch?v=GQSWUWODaEI, 2 pages.

\* cited by examiner

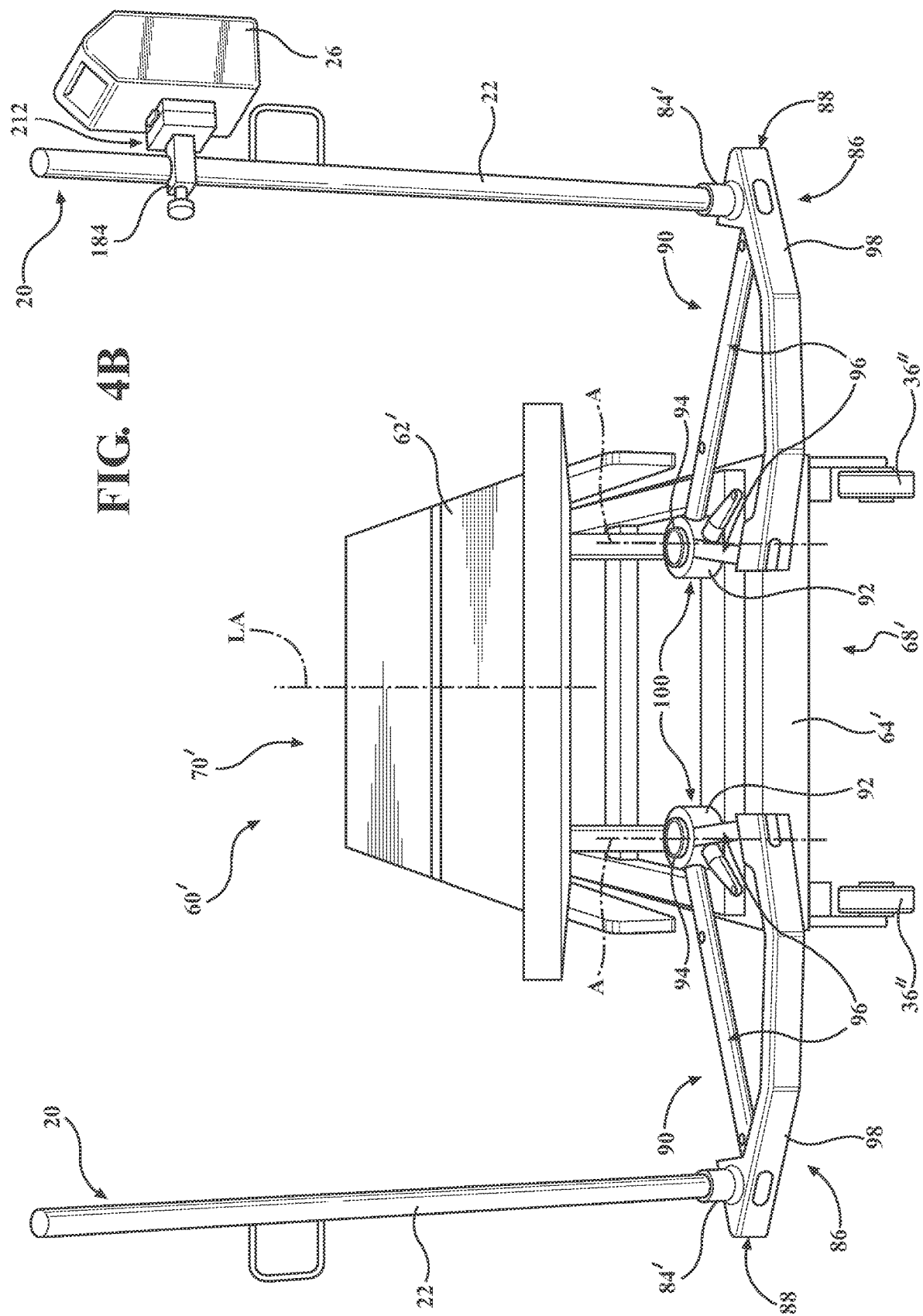

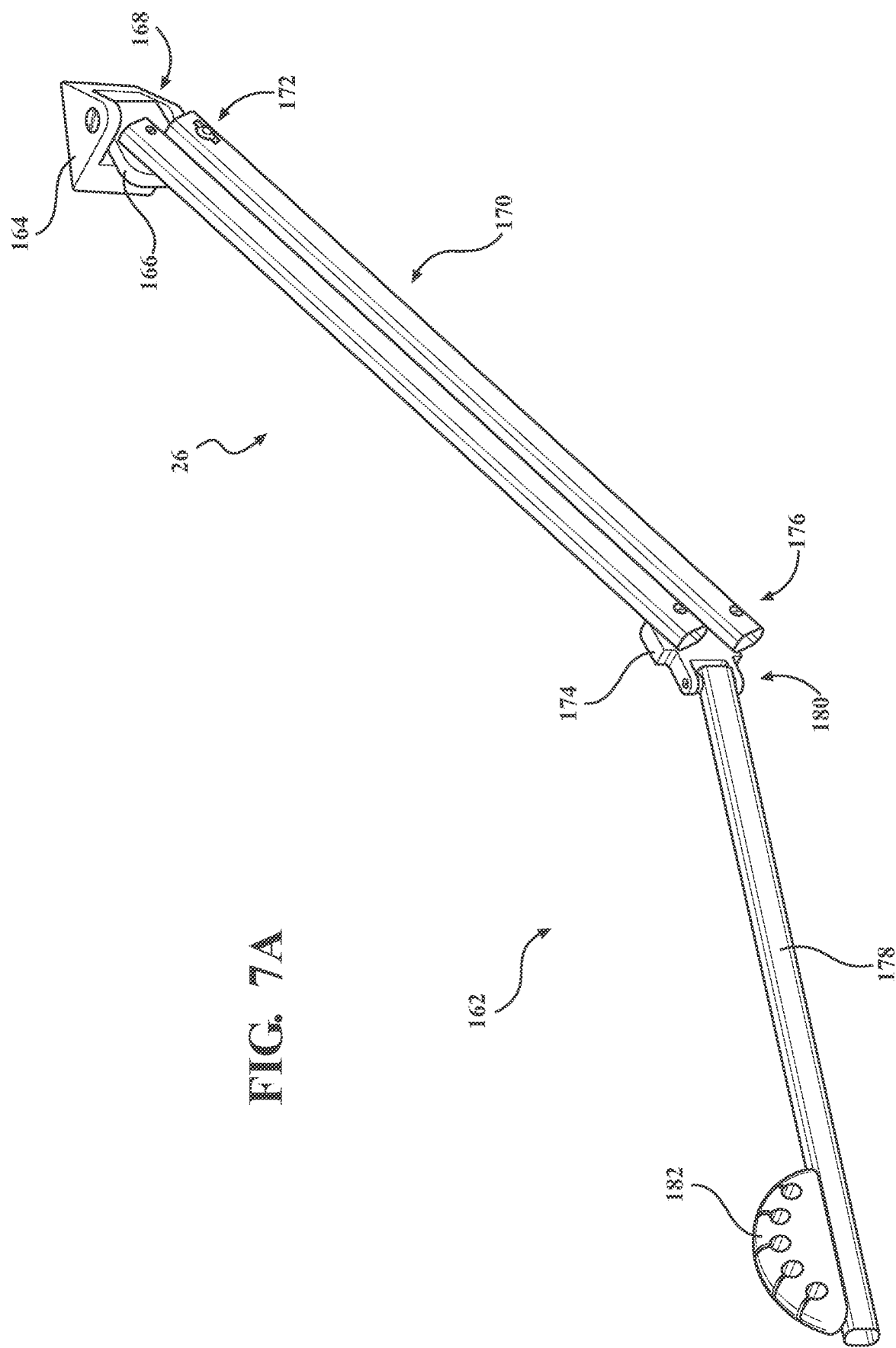

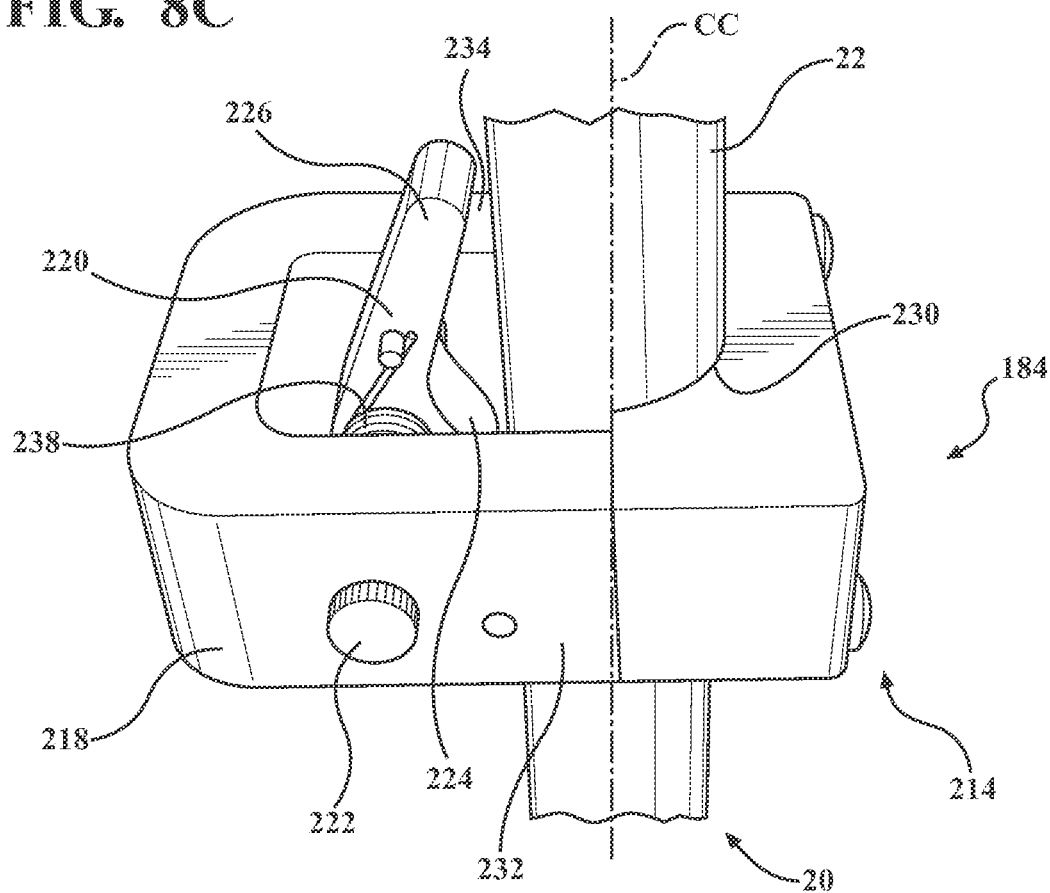

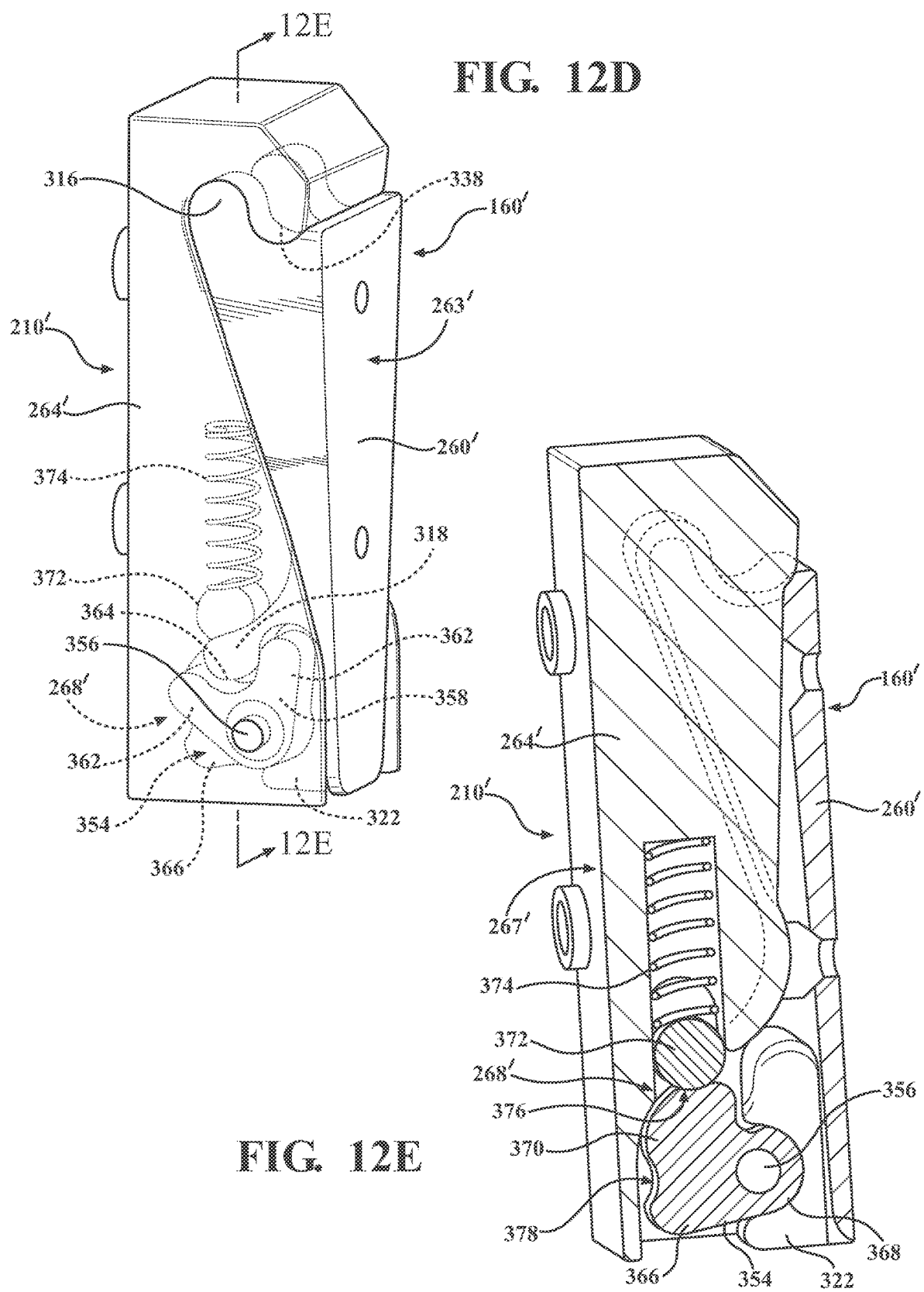

ACCESSORY SUPPORT AND COUPLING SYSTEMS FOR AN ACCESSORY SUPPORT

RELATED APPLICATIONS

This application is a continuation of U.S. patent application Ser. No. 16/782,163, filed on Feb. 5, 2020, which is a continuation of U.S. patent application Ser. No. 15/422,979, filed on Feb. 2, 2017, which, in turn, claims priority to and the benefit of U.S. Provisional Patent Application No. 62/290,244, filed on Feb. 2, 2016, and to U.S. Provisional Patent Application No. 62/314,561, filed on Mar. 29, 2016, the entire contents of each of which are hereby incorporated by reference.

TECHNICAL FIELD

The embodiments described herein relate to an accessory support and devices for an accessory support.

BACKGROUND

Accessory supports are used in the medical field and may support intravenous fluid containers. In some instances, accessory supports may be used to support other medical accessories that assist with patient care. By way of non-limiting example, medical accessories may include an infusion pump, a line coupler assembly, an oxygen bottle holder, a fluid warmer, a monitor, a respirator, a physiological sensor, and an oxygen bottle.

Caregivers, such as nurses, are often required to transfer medical accessories from one accessory support to another accessory support as a patient travels to various locations within a healthcare facility. Furthermore, movement of the patient in a wheelchair or bed with the attached accessory support can be cumbersome.

A system that overcomes one or more of the aforementioned challenges is desired.

SUMMARY

In one embodiment, a coupling system for coupling a medical accessory to an accessory support is provided. The coupling system comprises an accessory support having a power distribution system. The coupling system further comprises a first component supported by and electrically coupled to the accessory support. The first component comprises a first coupling portion, and a first electrical connector for electrically coupling the power distribution system of the accessory support to the medical accessory. The coupling system further comprises a second component configured to support the medical accessory and be electrically coupled to the medical accessory. The second component comprises a second coupling portion configured for being removably coupled to the first coupling portion of the first component, and a second electrical connector for electrically coupling the medical accessory to the first electrical connector. The first coupling portion and the second coupling portion are configured to allow pivoting motion between a first and second position. In the first position the second component is supported by the first component. In the second position the second component is supported by the first component and the first electrical connector is electrically coupled to the second electrical connector.

The present disclosure also provides a system for powering a medical accessory with an accessory support. The system comprises an accessory support having a DC power distribution system configured to output DC power. The system further comprises, a medical accessory that is free from an AC/DC converter and is configured to receive DC power. The system further comprises a first component. The first component comprises a first mounting portion, a first coupling portion, and a first electrical connector. The system further comprises a second component. The second component comprises a second mounting portion, a second coupling portion, and a second electrical connector. The first mounting portion is supported by the accessory support and the medical accessory is supported by the second mounting portion. The first electrical connector is electrically coupled to the power distribution system of the accessory support. The second electrical connector is electrically coupled to the medical accessory. The first component and the second component are configured such that when the first coupling portion is coupled to the second coupling portion, the first electrical connector is electrically coupled to the second electrical connector to enable the power distribution system of the accessory support to provide DC power to the medical accessory.

The present disclosure also provides, in another embodiment, a system for powering a medical accessory with an accessory support. The system comprises an accessory support. The accessory support comprises a power distribution system configured to selectively output D/C power and A/C power. The accessory support further comprises a controller configured to control the power distribution system. The system further comprises a first component. The first component comprises a first mounting portion, a first coupling portion, and a first electrical connector. The system further comprises a second component. The second component comprises a second mounting portion, a second coupling portion, and a second electrical connector. The first mounting portion is supported by the accessory support and the second mounting portion is configured to support the medical accessory. The first electrical connector is electrically coupled to the power distribution system of the accessory support. The second electrical connector is configured to be electrically coupled to the medical accessory. The first component and the second component are configured such that when the first coupling portion is coupled to the second coupling portion, the first electrical connector is electrically coupled to the second electrical connector to enable the power distribution system of the accessory support to provide power to the medical accessory, and the controller is configured to determine an identity of the medical accessory coupled to the second component, and cause the power distribution system to output A/C or D/C power based on the identity of the medical accessory.

BRIEF DESCRIPTION OF THE DRAWINGS

Advantages of the present invention will be readily appreciated as the same become better understood by reference to the following detailed description when considered in connection with the accompanying drawings.

FIG. 4B is a perspective view of the patient support apparatus of FIG. 4A with the two arm assemblies shown in a patient-care position.

FIG. 7A is a perspective view of an exemplary line coupler assembly.

FIG. 8C is a perspective view of the cam clamp of FIG. 8A shown engaging and unsecured to a portion of the accessory support.

FIG. 12D is a perspective view of the second component of FIG. 12B engaging the first component of FIG. 12A in a locked arrangement.

FIG. 12E is a sectioned perspective view of the second component of FIG. 12B engaging the first component of FIG. 12A in a locked arrangement.

DETAILED DESCRIPTION

Figure 1:
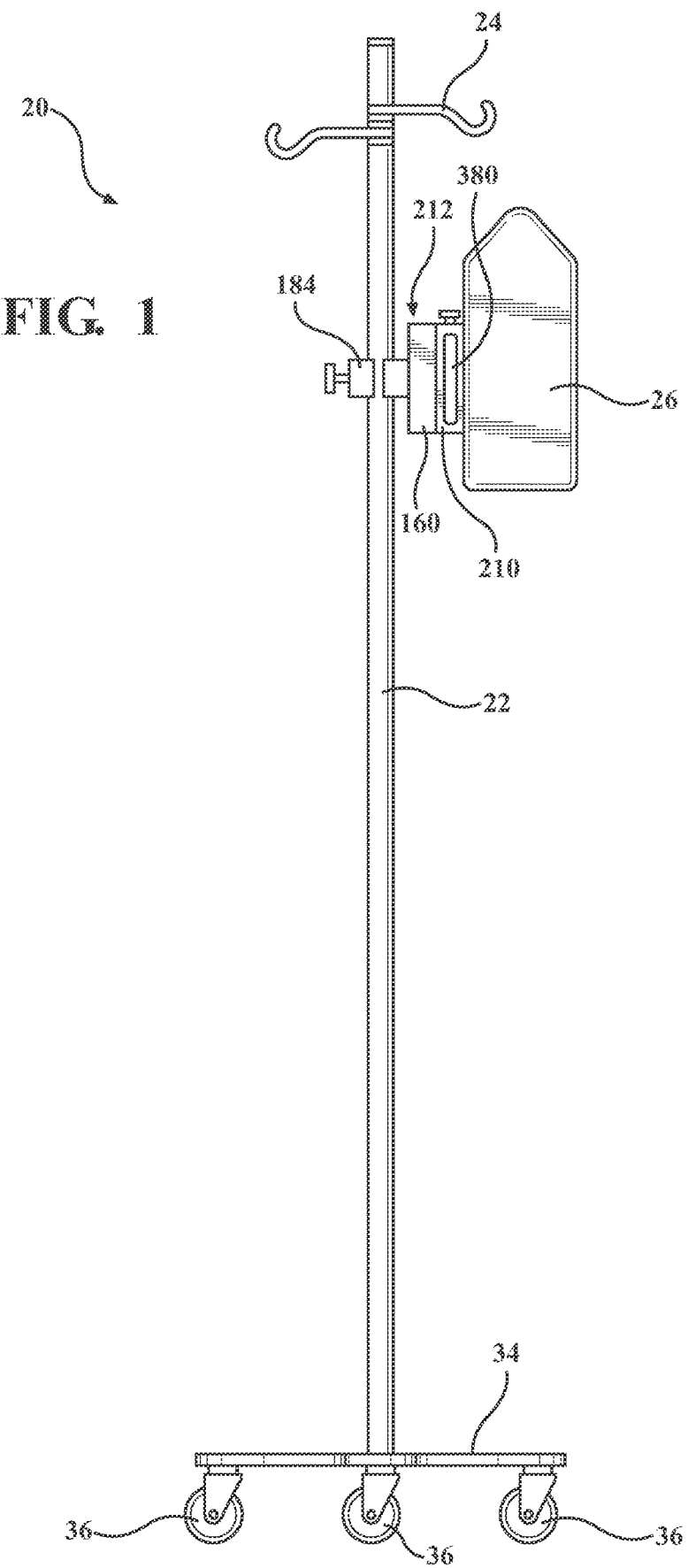
FIG. 1 is a side view of a first embodiment of an accessory support coupled to a wheeled base.

With reference to FIG. 1, an accessory support 20 for assisting with patient treatment is provided. The accessory support 20 is configured to support one or more medical accessories.

In FIG. 1, the accessory support 20 comprises a post 22, such as the illustrated cylindrical pole. The accessory support 20 is configured to aid patient treatment in different locations within a healthcare facility.

In some instances, it is necessary to provide fluids to a patient intravenously. The fluids may be disposed within an intravenous fluid container, which may be coupled to the post 22, or may be hung on a pole topper 24, which may be coupled to the post 22. In the illustrated embodiment, the pole topper 24 comprises a pair of hooks. Of course, still other pole topper configurations are contemplated. The intravenous fluid container may be coupled to the patient via an intravenous line such that the fluid can flow from the intravenous fluid container to the patient via the intravenous line.

A medical accessory 26 may be coupled to the accessory support 20. As illustrated in FIG. 1, the medical accessory 26 comprises a fluid infusion pump 26. The fluid infusion pump 26 may be fluidly coupled to the intravenous fluid container to control the flow rate of the intravenous fluid to the patient. The type and configuration of medical accessory that may be coupled to or supported by the accessory support 20 is not particularly limited. The medical accessory may comprise, by way of non-limiting example, an oxygen bottle holder, a fluid warmer, a monitor, a respirator, a physiological sensor, an oxygen bottle, a ventilator, a cardiac monitor, a pulse oximeter, a non-invasive blood pressure measuring device, a digital thermometer, a liquid oxygen module, a defibrillator, a respiratory rate measuring device and other medical accessories.

As illustrated in FIG. 1, the accessory support 20, such as post 22, can be coupled to a wheeled base 34. One exemplary wheeled base 34 is illustrated in FIG. 1. The wheeled base 34 comprises wheels 36 that permit the accessory support 20 to be transported throughout the healthcare facility in an upright position. Of course, the type of wheeled base 34 is not particularly limited. In the illustrated embodiment, the post 22 is non-telescopic.

Figure 2A:
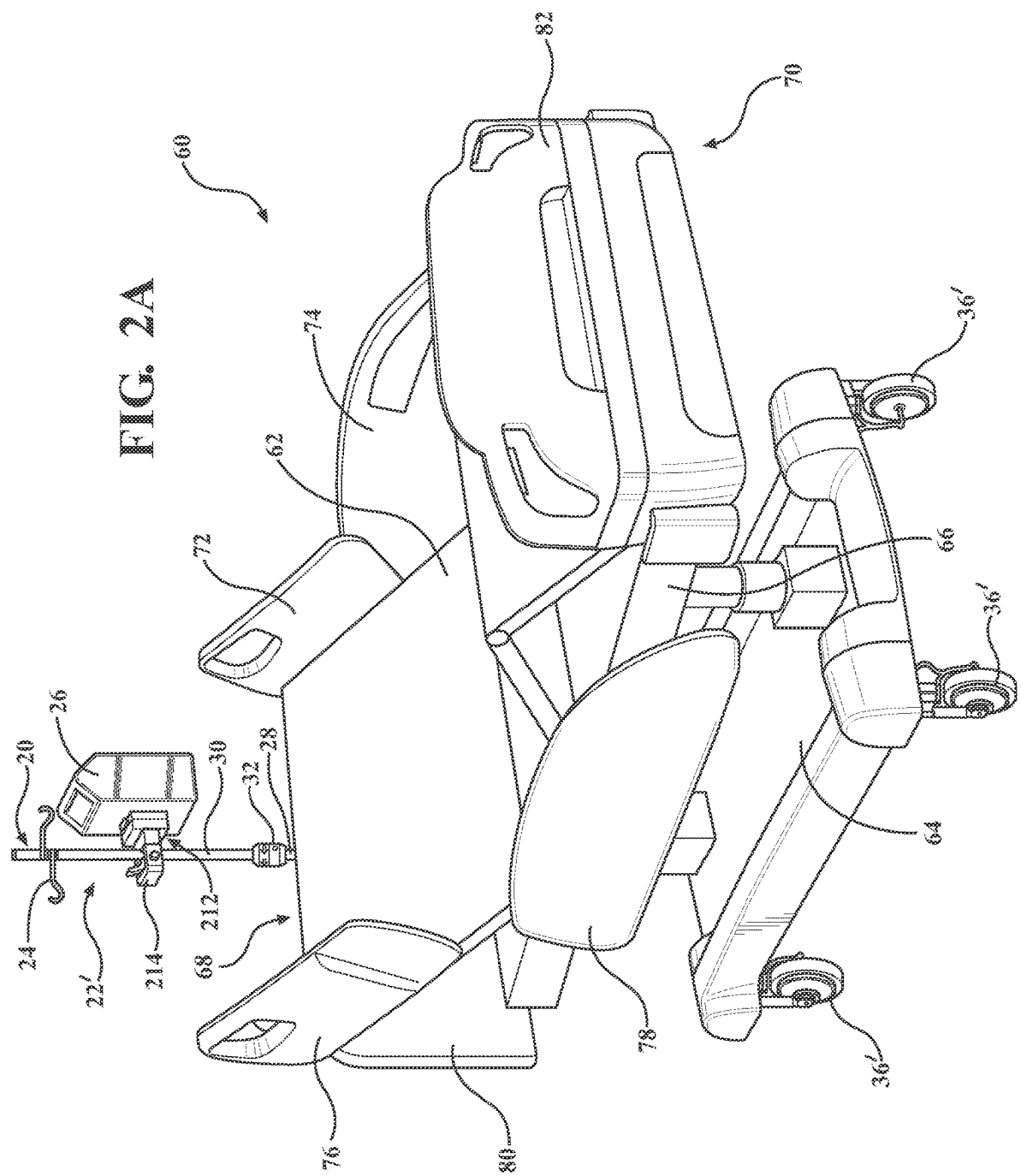
FIG. 2A is a perspective view of a patient support apparatus.
Figure 2B:
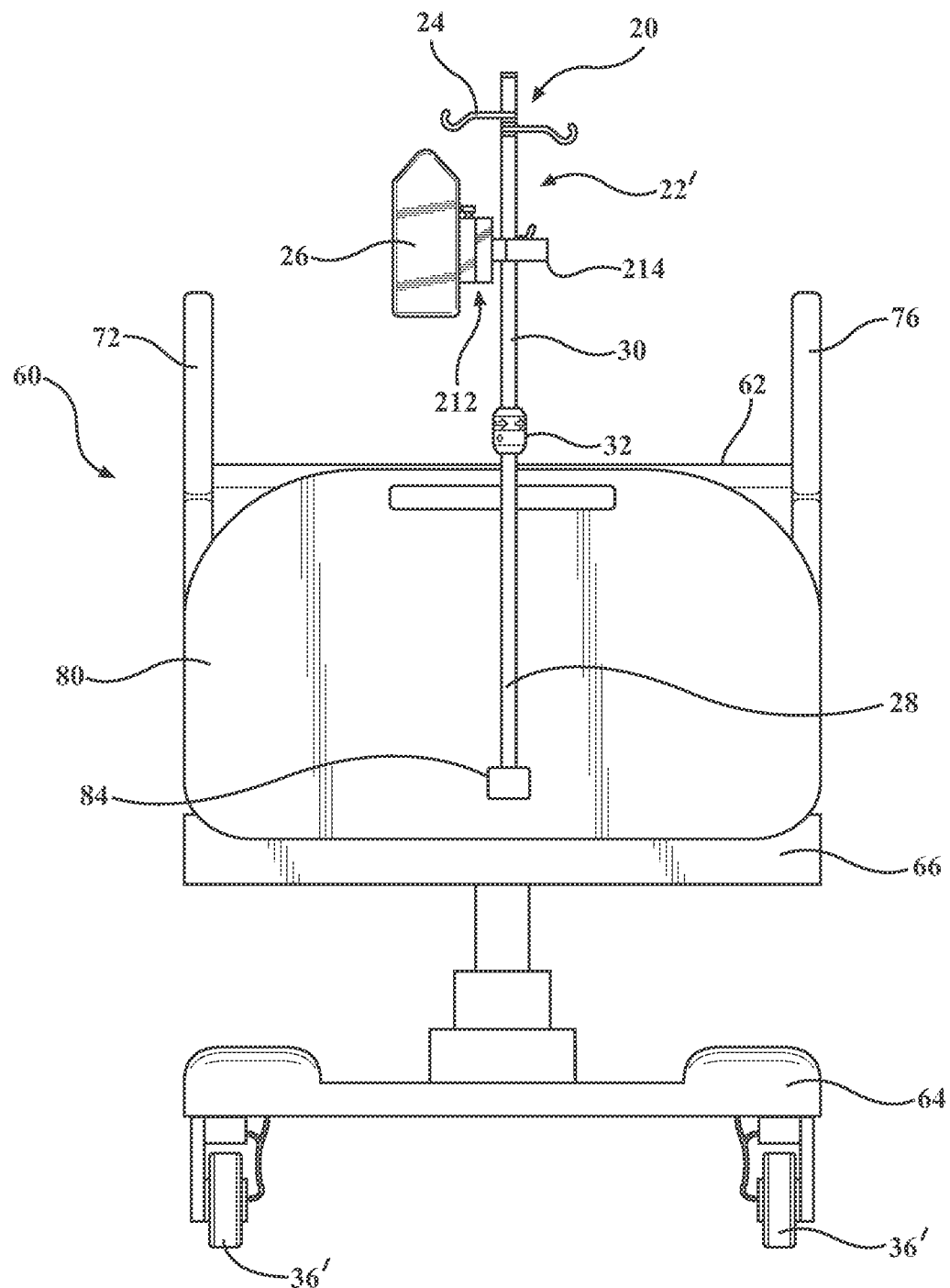
FIG. 2B is a back view of a head end of the patient support apparatus of FIG. 2A with the second embodiment of the accessory support coupled thereto.

In alternative embodiments, it should also be appreciated that the accessory support 20 may assume any suitable configuration, including a post 22' that is telescopic, as shown in FIGS. 2A and 2B. The telescopic post 22' comprises a bottom tube 28 coupled to a top tube 30, and a latching mechanism 32. The latching mechanism 32 is configured to fix the position of the top tube 30 relative to the bottom tube 28.

In other embodiments, when the post is non-telescopic, the post may be foldable about one or more folding junctions between a folded position and an extended position. In the extended position, the post has a greater length then when the post is in the folded position. Thus, the caregiver can advantageously extend or fold the post based on the needs of the patient.

In still other embodiments, when the post is non-telescopic, the post may comprise a first tube and a second tube adjacent the first tube and not coaxial with the first tube. The first and second tubes may be coupled together by one or more post sliders. The post slider is configured to allow the second tube slide upward relative to the first tube between a raised position and a lowered position. In the lowered position, the first tube is generally parallel and coextensive with the second tube but not coaxial. In the raised position, the post has a greater length then when the post is in the lowered position. Thus, the caregiver can advantageously slide the second tube to reach a total length appropriate for the needs of the patient or caregiver.

The accessory support 20, such as posts 22, 22' may comprise metal such as stainless steel, or a composite material such as carbon fiber, or any other material that provides sufficient rigidity to support medical accessories.

Figure 3A:
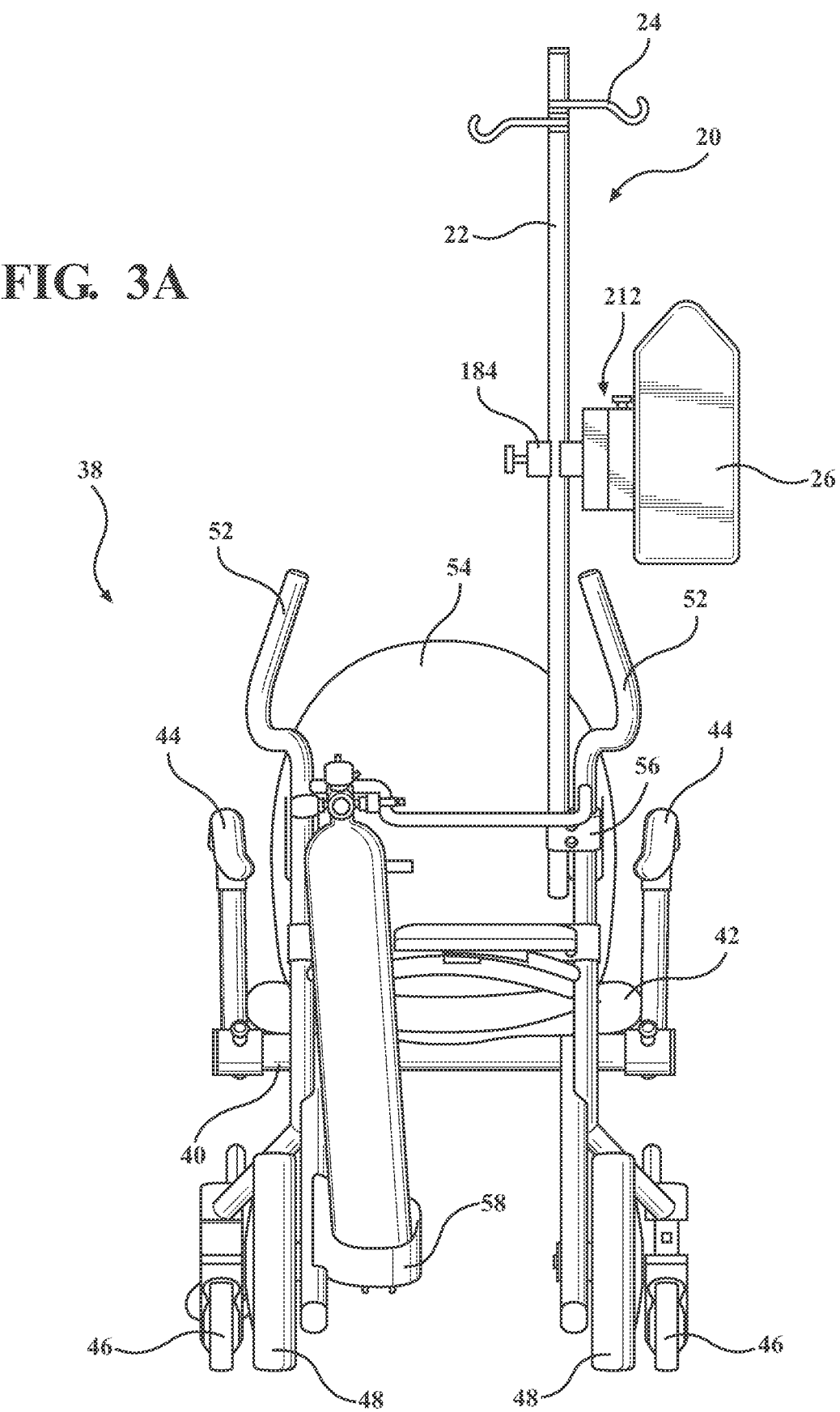
FIG. 3A is a back view of a patient transport chair.
Figure 3B:
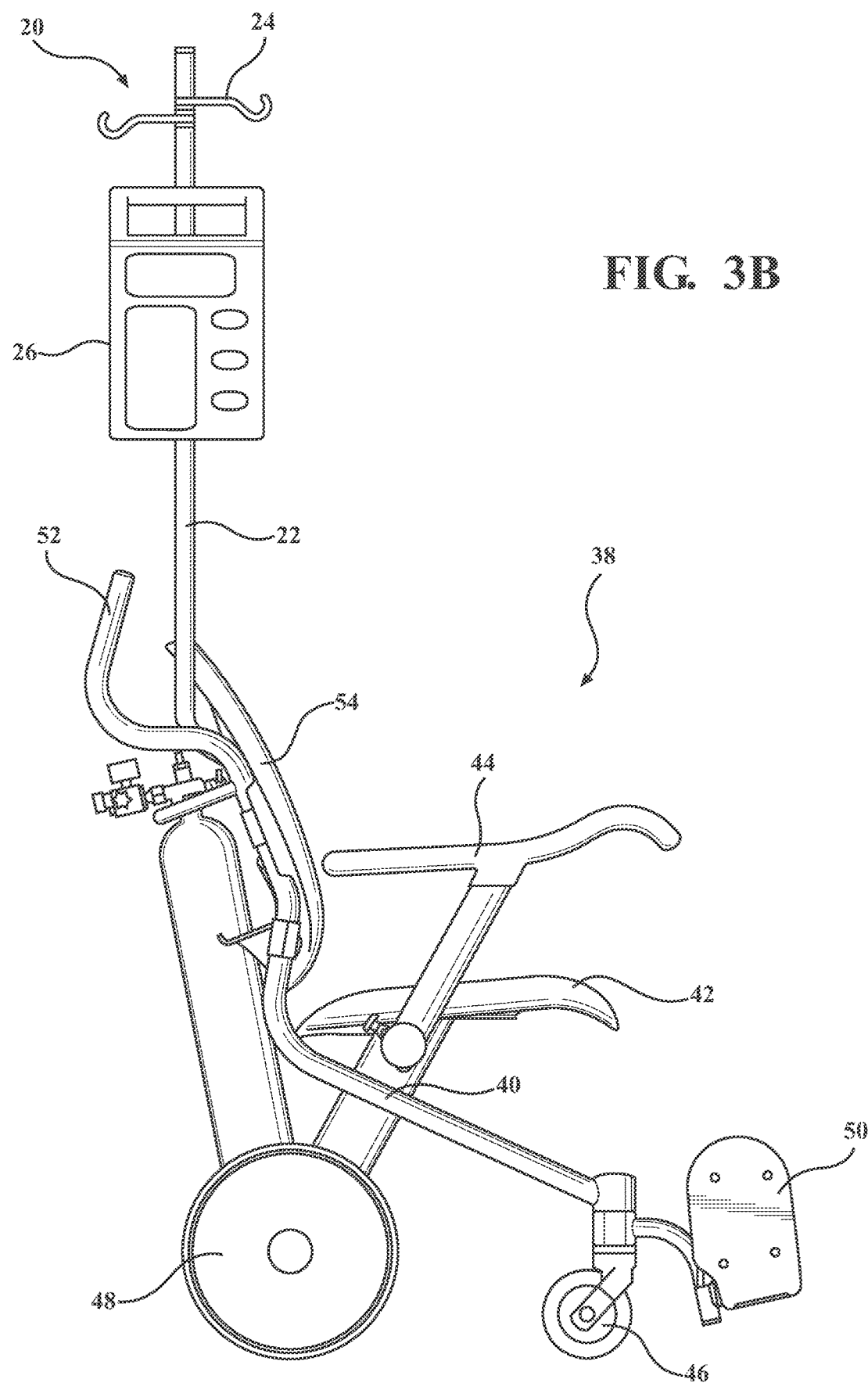
FIG. 3B is a right-side view of the patient transport chair of FIG. 2A.

As shown in FIGS. 3A and 3B, in some instances the accessory support 20, illustrated as post 22, may be coupled to a patient transport chair 38. The patient transport chair 38 is adapted to allow a patient to be transported to different locations within a healthcare facility. The patient transport chair 38 comprises a chair frame 40, a seat 42 supported thereon, a pair of armrests 44, a plurality of front wheels 46, a plurality of rear wheels 48, a footrest 50, a pair of handles 52, a back rest 54, and a frame mount 56. It should be appreciated that the design of the patient transport chair 38 is not particularly limited, and may assume any suitable configuration. For example, the patient transport chair 38 may also comprise a brake pedal, a stop pedal, an additional footrest, and an oxygen bottle holder 58. Still other features may also be added to the patient transport chair 38.

Post 22, is configured to be removably retained within the frame mount 56 of the patient transport chair 38. The frame mount 56 may engage the post 22 such that the post 22 maintains its upright orientation. The configuration of frame mount 56 is not particularly limited, and may comprise a void or cavity that the post 22 rests within. Alternatively, the frame mount 56 may comprise screw threads that are complementary with a set of threads that are disposed at the bottom of the post 22. Alternatively still, the frame mount 56 may be configured to releasably engage the bottom of the post 22 to prevent rotational and/or axial movement of the post 22 relative to the patient transport chair 38.

As shown in FIGS. 2A and 2B, the accessory support 20 such as one or more telescopic posts 22', may alternatively be coupled to a patient support apparatus 60. In the illustrated embodiment, the patient support apparatus 60 comprises a patient support deck 62, a support base 64 and an intermediate frame 66. The intermediate frame 66 is spaced above the support base 64. The patient support deck 62 is disposed on the intermediate frame 66. The patient support deck 62 comprises several sections, some of which are pivotable relative to the intermediate frame 66. The patient support deck 62 provides a surface upon which the patient is supported.

The patient support deck 62, support base 64, and intermediate frame 66, each have a head end 68 and a foot end 70 corresponding to the designated placement of the patient's head and feet on the patient support apparatus 60. The construction of the patient support apparatus 60 may take on any known or conventional design, and is not limited to that specifically set forth above. In some instances, a mattress may be disposed on the patient support deck 62 such that the patient rests directly on the mattress.

Side rails 72, 74, 76, 78 are supported by the support base 64. A first side rail 72 is positioned at a right head end of the intermediate frame 66. A second side rail 74 is positioned at a right foot end of the intermediate frame 66. A third side rail 76 is positioned at a left head end of the intermediate frame 66. A fourth side rail 78 is positioned at a left foot end of the intermediate frame 66. If the patient support apparatus 60 is a stretcher or a cot, there may be fewer side rails. The side rails 72, 74, 76, 78 are movable between a raised position in which they block ingress and egress into and out of the patient support apparatus 60, and a lowered position in which they are not an obstacle to such ingress and egress. The side rails 72, 74, 76, 78 may also be movable to one or more intermediate positions between the raised position and the lowered position. In still other configurations, the patient support apparatus 60 may not comprise any side rails.

A headboard 80 and a footboard 82 are coupled to the intermediate frame 66. In other embodiments, when the headboard 80 and footboard 82 are included, the headboard 80 and footboard 82 may be coupled to other locations on the patient support apparatus 60, such as the support base 64. In still other embodiments, the patient support apparatus 60 does not comprise the headboard 80 and/or the footboard 82.

In the illustrated embodiment, the patient support apparatus 60 may comprise wheels 36'. The wheels 36' are coupled to the support base 64 to facilitate transport of the patient support apparatus 60 over floor surfaces. The wheels 36' are arranged in each of four quadrants of the support base 64 adjacent to corners of the support base 64. In the embodiment shown, the wheels 36' are able to rotate and swivel relative to the support base 64 during transport. It should be understood that various configurations of the wheels 36' are contemplated. By way of non-limiting example, the wheels 36' may be caster wheels, non-steerable, steerable, or combinations thereof. The wheels 36' may be movable between a stowed position for instances where the patient support apparatus 60 is not required to be transported and a deployed position for when the patient support apparatus 60 is required to be transported. Additional wheels are also contemplated. In some cases, the patient support apparatus 60 may not comprise any wheels 36'.

In the illustrated embodiment, the patient support apparatus 60 is a hospital bed. It is contemplated, however, that the patient support apparatus 60 may be a stretcher, cot, table, or similar apparatus utilized in the care of a patient.

Referring to FIG. 2B, the headboard 80 comprises a post mount 84. In the illustrated embodiment, the post mount 84 is configured to engage the bottom of the accessory support 20, such as the bottom of the post 22' to prevent movement of the post 22' relative to the patient support apparatus 60. The post mount 84 may be configured to engage the post 22' to prevent axial or rotational movement of the post 22' relative to the headboard 80. The design of the post mount 84 will depend on the accessory support 20 that will be engaged. Of course, it is also contemplated that the other portions of the patient support apparatus 60 may comprise the post mount 84 including, but not limited to, the foot board, the side rails, one or more portions of the support base, intermediate frame, or patient support deck. Furthermore, it should be appreciated that a single patient support apparatus 60 may comprise multiple post mounts 84 and, hence, may be coupled to multiple accessory supports 20.

Figure 4A:
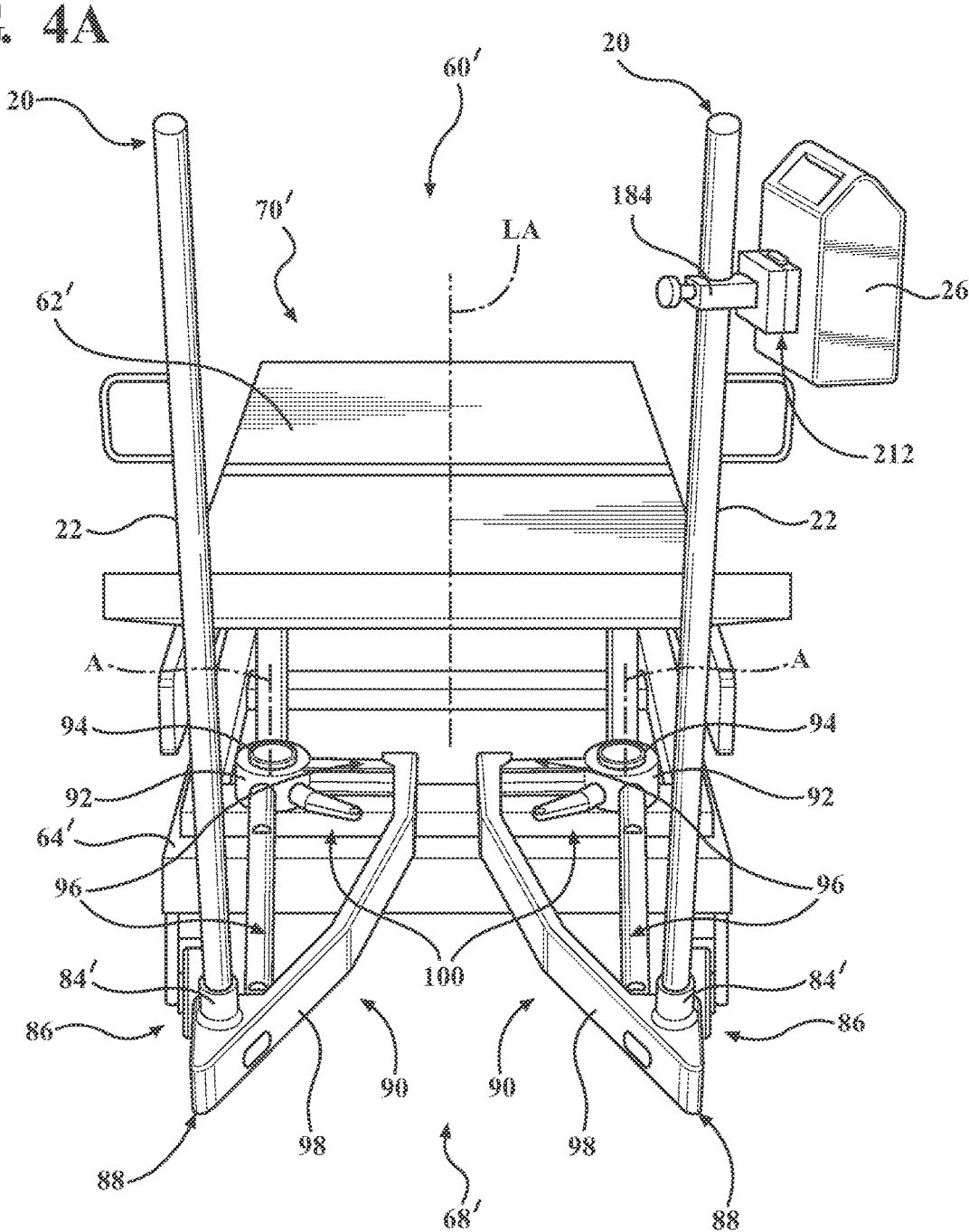
FIG. 4A is a perspective view of a head end of a second type of patient support apparatus including two arm assemblies shown in a transport position.

With reference to FIGS. 4A and 4B, an alternative patient support apparatus 60' is provided. The patient support apparatus 60' comprises a patient support deck 62' and a support base 64'. Each of the support base 64' and patient support deck 62' have a head end 68' and a foot end 70' corresponding to the designated placement of the patient's head and feet on the patient support apparatus 60'.

As illustrated, patient support apparatus 60' comprises at least one arm assembly 86 pivotably mounted to the support base 64' about a pivot axis A, such that each arm assembly 86 can independently assume a number of different rotational positions relative to the patient support deck 62'. In embodiments where multiple arm assemblies are present, it should be appreciated that the arm assemblies 86 may be linked with one or more timing arms, such that they move in tandem with one another. It should also be appreciated that the arm assemblies 86 may be coupled to other portions of the patient support apparatus 60' such as the intermediate frame.

In the illustrated embodiment, the arm assemblies 86 are mounted at the head end 68' of the support base 64'; however, it should be appreciated that the arm assemblies 86 may be mounted at other locations on the patient support apparatus 60' such as, by way of non-limiting example, the foot end 70' of the support base 64', or the head end 68' of the patient support deck 62'.

Throughout this disclosure, the terms 'coupling', 'mounting', 'coupled', 'mounted', etc. are used interchangeably. In some cases, the terms refer to semi-permanent connections created through the use of various fasteners. In other cases, the terms refer to 'quick-connections' configured to be easily connected and disconnected from one another.

The arm assemblies 86 may be configured to be rotatable relative to the support base 64' into a transport position (see FIG. 4A) and a patient-care position (see FIG. 4B). The arm assemblies 86 each have a free end 88 corresponding to the end of the rotatable arm assemblies 86 extending outward from the patient support apparatus 60', as shown in FIGS. 4A and 4B. In the illustrated embodiment, a post mount 84' is coupled to the free end 88 of each arm assembly 86. In this embodiment, the accessory support 20, such as post 22, may be coupled to the post mount 84'. In the illustrated embodiment, the post mount 84' is movable relative to the head end 68' of the patient support apparatus 60' by virtue of movement of the arm assembly 86 relative to the support base 64'. However, it should be appreciated that the post mount 84 may be coupled to any suitable location on the arm assembly 86, and may assume any suitable configuration.

In accordance with one embodiment, and with reference to FIG. 4A, when the arm assemblies 86 are in the transport position, the accessory support 20 coupled thereto is positioned longitudinally beyond the head end 68' of the patient support apparatus 60'. It should be appreciated that in instances where the arm assembly is positioned at the foot end 70' of the support base 64', the post 22 may be positioned longitudinally beyond the foot end 70' of the patient support apparatus 60'. In contrast, in the transport position, the arm assemblies 86 and the associated accessory support 20 may be substantially parallel with a longitudinal axis LA of the patient support apparatus 60'.

In the patient-care position, at least one of the arm assemblies 86 extend transversely to the patient support apparatus 60'. In this position, the accessory supports 20 are spaced apart from the head end 68' of the patient support apparatus 60' and, hence, medical accessories coupled thereto are spaced away from a patient's head. In some instances, when in the patient-care position, the accessory support 20 may be positioned longitudinally between the head end 68' and the foot end 70' of the patient support apparatus 60'.

Generally speaking, when the arm assemblies 86 are in the patient-care position, the accessory support 20 is positioned at a convenient location relative to the patient support apparatus 60' to facilitate care of the patient, whereas, when the arm assemblies 86 are in the transport position, the accessory support 20 is positioned substantially in-line with the patient support apparatus 60', but not necessarily spaced away from the head end 68' of the patient support apparatus 60'.

In certain embodiments, when the arm assemblies 86 are in the transport position (FIG. 4A), the width profile of the patient support apparatus 60', including the arm assemblies 86, is smaller than the width profile of the patient support apparatus 60' when the arm assemblies 86 are in the patient-care position (FIG. 4B). The smaller width profile of the patient support apparatus 60' in the transport position facilitates transport of the patient support apparatus 60' through narrow doors or elevator entrances. In addition, when the arm assemblies 86 are in the patient-care position, the proximity of the accessory support 20, and the medical accessories supported thereon, are spaced away from the head end 68' of the patient support apparatus 60' and, accordingly, away from the head of the patient. As will be appreciated, the arm assembly 86 may also be configured to pivot to any number of intermediate positions between the transport position and the patient-care position. It should be further understood that the phrases "transport position" and "patient-care position" are used to facilitate description of the positions of the various arm assemblies, and do not limit the potential uses of the arm assemblies. More specifically, it should be understood that a caregiver may find it advantageous to move the patient support apparatus while the arm assemblies are in the patient-care position or may find it advantageous to keep the arm assemblies in the transport position even while the patient support apparatus is stationary.

As shown in FIGS. 4A and 4B, in the exemplary embodiment, each arm assembly 86 comprises an arm frame 90, a pivot member 92, and a stationary member 94. In the illustrated embodiment, each arm frame 90 is substantially triangular in shape and comprises radial frame members 96 that are coupled to the pivot member 92 at a first end and coupled to a mounting arm member 98 at a second end. The pivot member 92 is rotatably coupled to the stationary member 94 such that the pivot member 92 and arm frame 90 coupled to the pivot member 92 can rotate about the pivot axis A. The stationary member 94 is coupled to the support base 64'. In some instances, by way of non-limiting example, the stationary member 94 may be integrally formed with the support base 64' by welding. It should be appreciated that other configurations of the arm assemblies 86 are also contemplated so long as they enable movement of the post mount 84', i.e. the accessory support 20, relative to the patient support apparatus 60'.

Figure 4C:
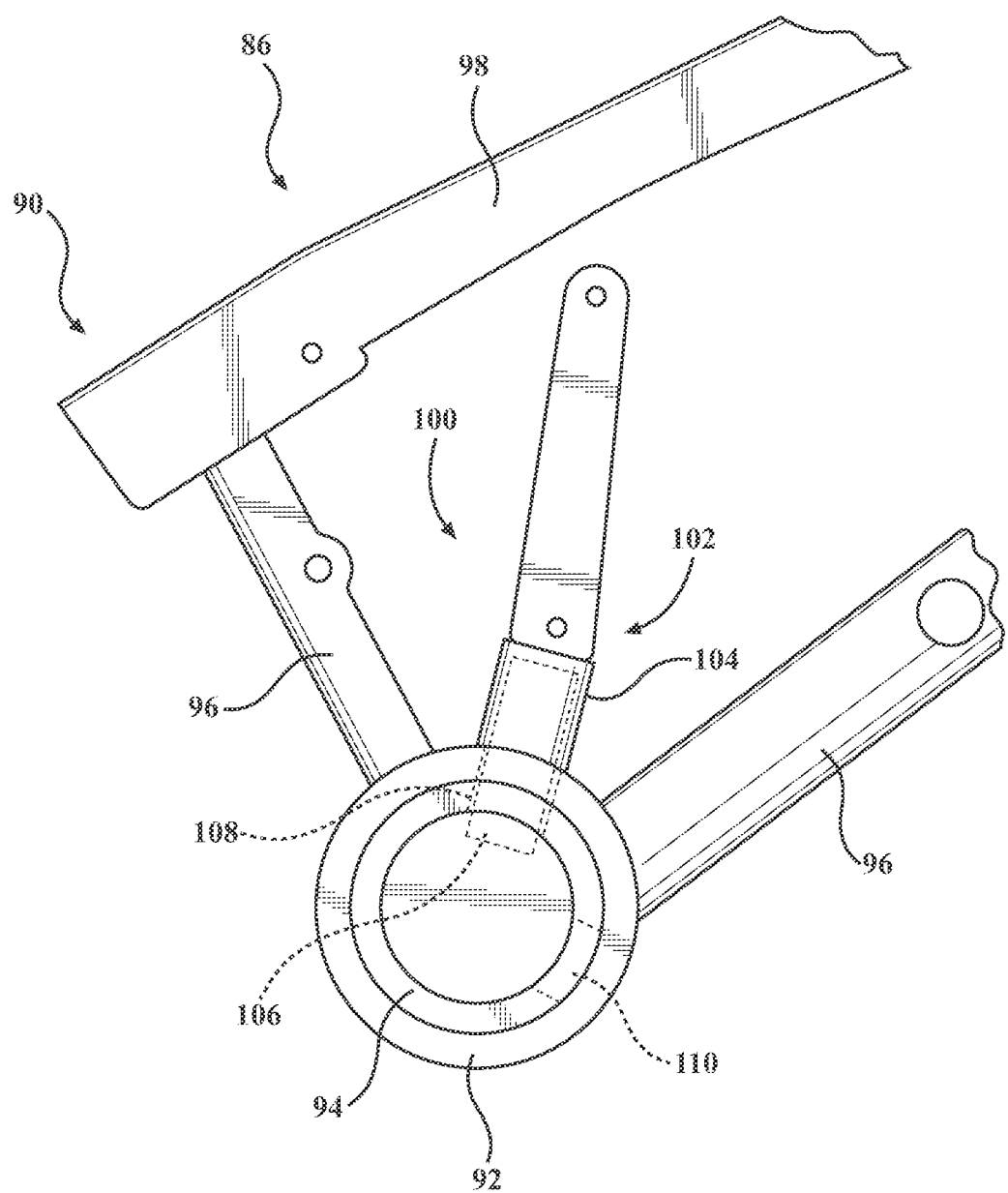
FIG. 4C is a partial top-side view of one of the arm assemblies of FIG. 4A.

As shown in FIG. 4C, in certain embodiments, the arm assembly 86 comprises a locking device 100 configured to selectively lock the arm assembly 86 in one or more of the positions such as the transport position, the patient-care position, or any number of intermediate positions.

While the configuration of the locking device 100 is not particularly limited in the illustrated embodiment, the locking device 100 comprises a plunger mechanism 102. The plunger mechanism 102 may comprise a plunger housing 104 coupled to the pivot member 92 and a pin 106 disposed within the plunger housing 104 for selective engagement with one or more notches 108, 110 of the stationary member 94. By way of non-limiting example, the plunger housing 104 may be coupled to the pivot member 92 by welding such that the plunger housing 104 and pivot member 92 are fixed relative to each other.

The plunger mechanism 102 locks when the pin 106 extends through the pivot member 92 to engage one of the notches such as, by way of non-limiting example, a first notch 108 in the stationary member 94, as shown in FIG. 4C. The first notch 108 may be substantially the same size, or the same size, as the pin 106 such that when the pin 106 engages the first notch 108, the pivot member 92 is fixed relative to the stationary member 94. If the pin 106 does not engage a notch in the stationary member 94, the pivot member 92 is permitted to rotate with respect to the stationary member 94. It is further contemplated that the stationary member 94 may comprise a second notch 110. In instances where the second notch 110 is present, the first notch 108 may correspond to the transport position and the second notch 110 may correspond to the patient-care position. In this manner, a caregiver can position and lock the arm assemblies 86 and corresponding accessory support 20 as desired. Additionally, the stationary member 94 may comprise any suitable number of notches to ensure that the arm assemblies 86 are lockable in any number of desired positions. Of course, other configurations of the locking device 100 are also contemplated.

In one embodiment, the locking device comprises a friction disc mechanism described in U.S. patent application Ser. No. 15/267,793 which is hereby incorporated by reference in its entirety.

As an alternative, or in addition to the locking device 100 described above, the arm assembly may comprise a clutch device configured to restrict pivotal movement of the arm assembly relative to the support base. The clutch device may retain the arm assembly in the desired position unless a predetermined frictional force is exceeded. Various clutch device configurations are contemplated.

Figure 5A:
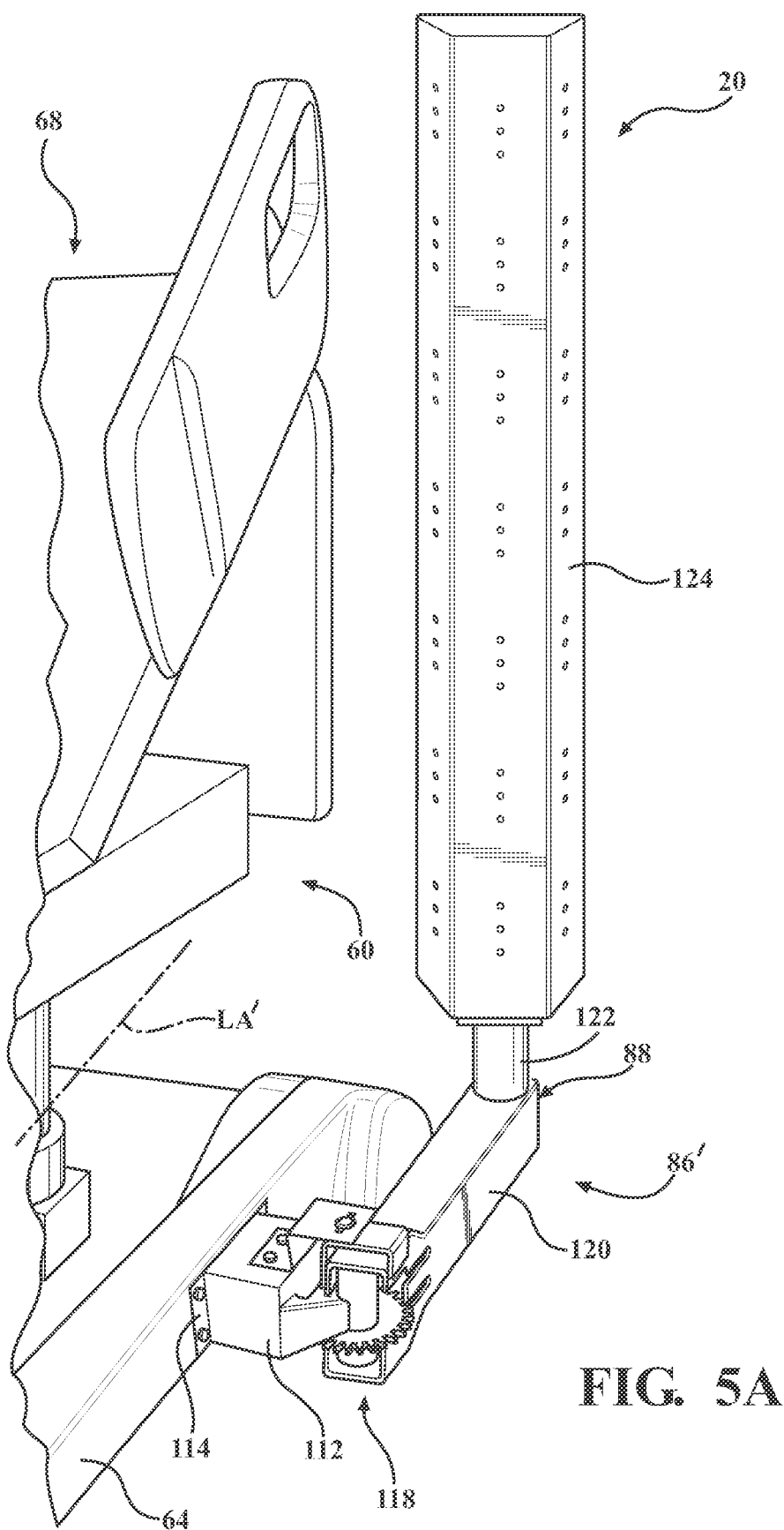
FIG. 5A is a partial perspective view of the patient support apparatus of FIG. 2A shown with another embodiment of the arm assembly shown in a transport position.
Figure 5B:
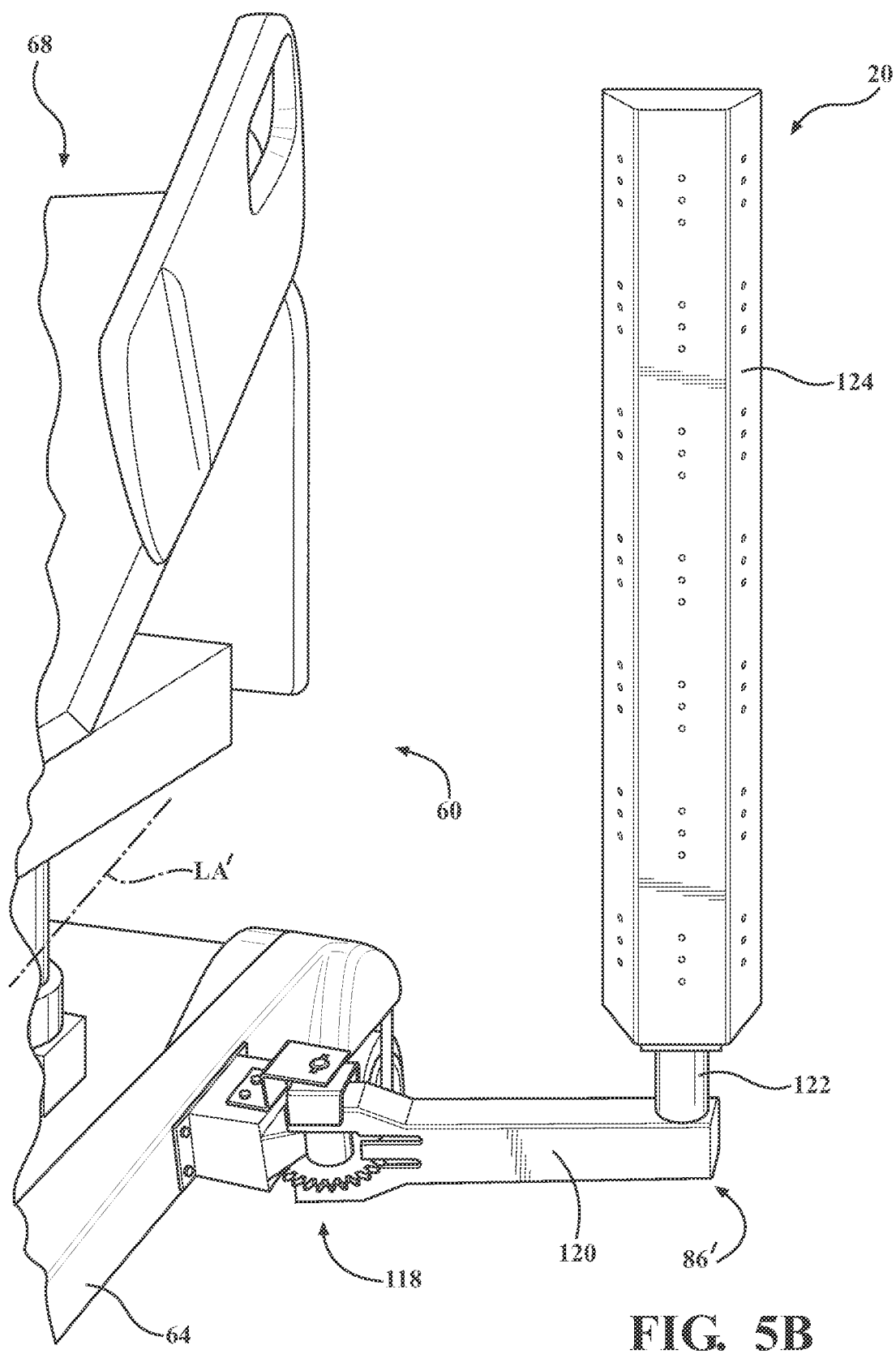
FIG. 5B is a partial perspective view of the patient support apparatus of FIG. 5A shown with the arm assembly in a patient-care position.
Figure 5C:
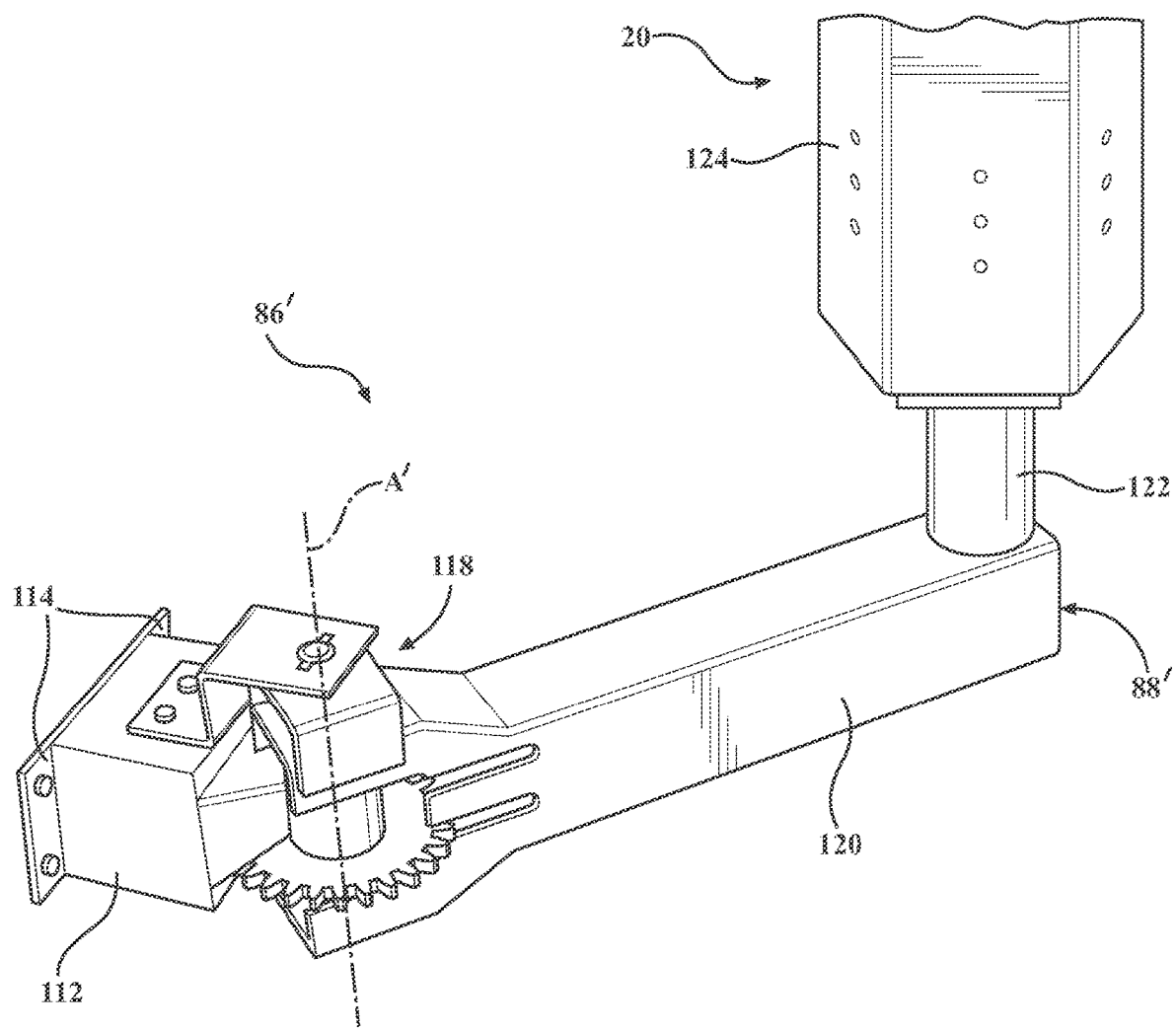
FIG. 5C is a partial view of the arm assembly of FIG. 5A in intermediate position between the transport position and the patient-care position.

In an alternative embodiment, as shown in FIGS. 5A and 5C, an arm assembly 86' comprises a mounting member 112, a pivot linkage 118, and a swing member 120 coupled to the pivot linkage 118. The mounting member 112 is configured to couple the arm assembly 86' to the support base 64 of the patient support apparatus 60 via flanges 114. With reference to FIG. 5C, the pivot linkage 118 is configured to couple to the swing member 120 and allow rotation of the swing member about a pivot axis A'. As shown in FIG. 5A, the swing member 120 further comprises an accessory support mount 122 configured to support and retain the accessory support 20, such as a mounting apparatus 124 (described below) in an upright position.

In the illustrated embodiment, with reference to FIG. 5A, one arm assembly 86' is shown coupled to the patient support apparatus 60. It is to be appreciated that two, or more, arm assemblies 86' may be coupled to the patient support apparatus 60 in a similar manner. Additionally, it should be appreciated that the arm assemblies may include suitable clutching mechanisms or locking mechanisms to retain the arm assemblies in desirable positions.

With respect to FIGS. 5A and 5B, the arm assembly 86' is operable between a transport position (FIG. 5A) and a patient-care position (FIG. 5B). In the transport position (FIG. 5A), the width profile of the patient support apparatus 60, including arm assembly 86', is smaller than the width profile of the patient support apparatus 60 when the arm assembly 86' is in the patient-care position (FIG. 5B). The smaller width profile of the patient support apparatus 60 in the transport position facilitates transport of the patient support apparatus 60 through narrow doors or elevator entrances. In addition, when the arm assembly 86' is in the patient-care position, the proximity of the accessory support 20, and the medical accessories supported thereon, are spaced away from the head end 68 of the patient support apparatus 60 and, accordingly, away from the head of the patient. As will be appreciated, the arm assembly 86' may also be configured to pivot to any number of intermediate positions between the transport position and the patient-care position.

In the patient-care position (FIG. 5B) the arm assembly 86' extends transversely to the patient support apparatus 60.

In addition, when the arm assembly 86' is in the patient-care position, the swing member 120 is neither parallel, nor substantially parallel, with the longitudinal axis LA' of the patient support apparatus 60. It is contemplated that in some instances the mounting apparatus 124 is positioned between the head end 68 and the foot end 70 when then arm assembly 86' is in the patient-care position.

Referring to FIG. 5A, the accessory support mount 122 is adjacent a free end 88' of the swing member 120. It is contemplated that the accessory support mount 122 may be coupled to any suitable location on the patient support apparatus 60 or the arm assembly 86'.

Figure 6A:
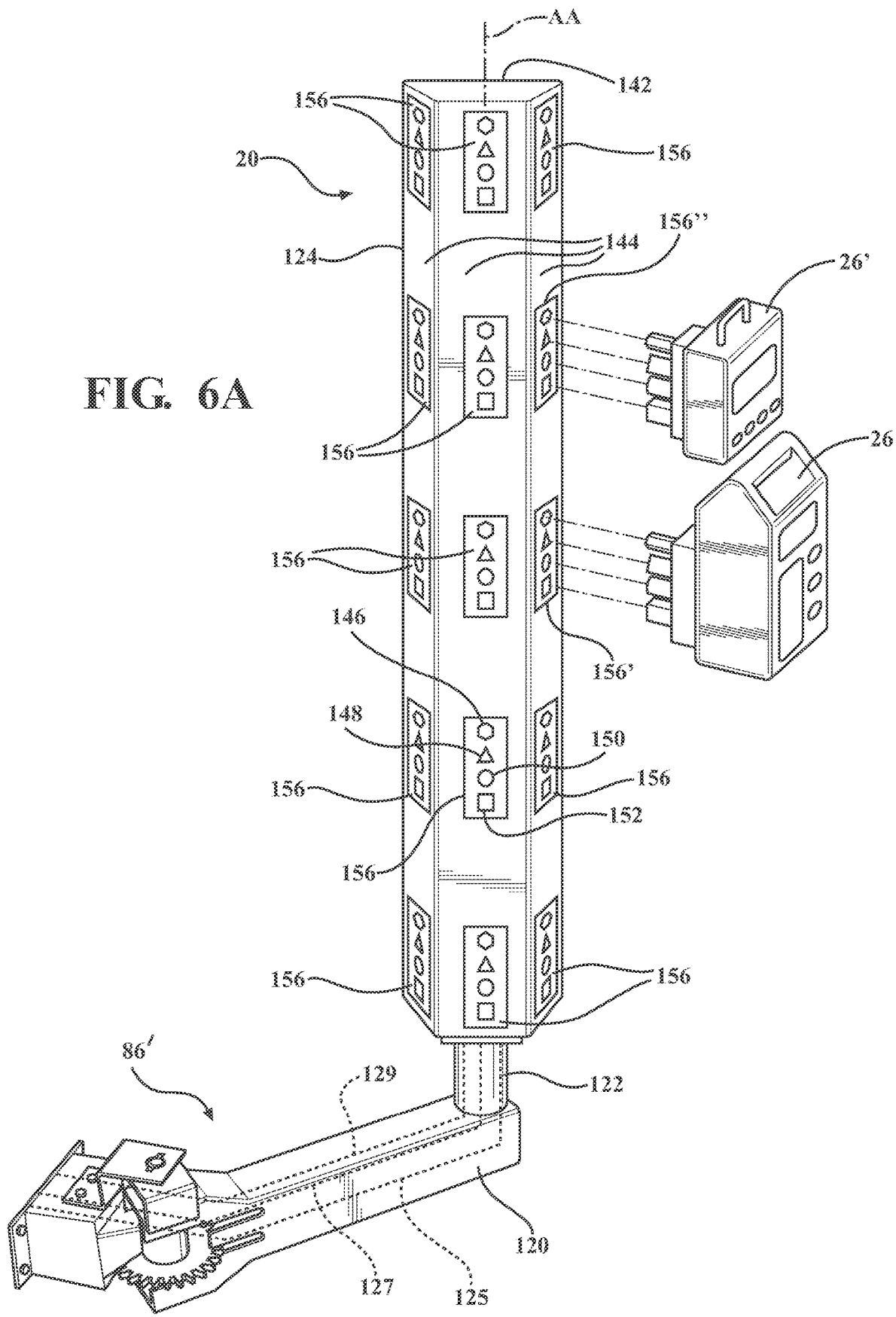
FIG. 6A is a perspective view of the arm assembly of an accessory support of FIG. 5C, depicted schematically with coupling sets, and medical accessories configured to couple to the coupling sets.

Referring now to FIG. 6A, an alternative embodiment of an accessory support 20 is shown as mounting apparatus 124. The mounting apparatus 124 comprises a combination of interfaces configured to mechanically, fluidly, and/or electrically couple to medical accessories 26, 26' that are placed adjacent to the housing 142. In the context of this disclosure, electrically coupled means the medical accessory 26, 26' is coupled to the mounting apparatus 124 such that the medical accessory 26, 26' may receive electrical power from the mounting apparatus 124 and/or exchange data with a controller of the mounting apparatus 124 or other associated medical accessories coupled thereto. The electrical coupling may be implemented through wiring, direct electrical contact through interfacing electrical conductors, and/or through wireless transfer, such as electromagnetic, capacitive, and/or inductive wireless transfer. Referring to FIG. 6A, the mounting apparatus 124 may comprise any combination of mechanical interfaces 146, data interfaces 148, power interfaces 150, and/or fluid interfaces 152 suitable for the expected utilization of the mounting apparatus 124. Thus, when one of the medical accessories 26, 26' is placed adjacent to the housing 142 of the mounting apparatus 124 and engages the one or more interfaces, the medical accessory 26, 26' may be mechanically supported by the housing 142 (the mechanical interface 146), the medical accessory 26, 26' may be coupled to the housing 142 in a manner suitable to exchange data (the data interface 148), the medical accessory 26, 26' may be coupled to the housing 142 in a manner suitable to provide power to the medical accessory 26, 26' (the power interface 150), and/or the medical accessory 26, 26' may be coupled to the housing 142 in a manner suitable to provide fluid to the medical accessory 26 (the fluid interface 152).

In some instances, the medical accessory 26, 26' may receive power from the power interface 150 to power a communication device of the medical accessory 26, 26'. The communication device may provide short-range wireless data exchange with the controller of the mounting apparatus 124 or with communication devices of other medical accessories coupled thereto. Examples of such short-range wireless communication include, but are not limited to, Bluetooth, Zigbee, near field communication (NFC), Wi-Fi, infrared, or the like.

The mounting apparatus 124 may be coupled to the accessory support mount 122 or other suitable structures described throughout. The exemplary mounting apparatus 124 comprises a housing 142. In the illustrated embodiment, the housing 142 has a polygonal shape. The housing 142 comprises number of flat, or substantially flat, faces 144. In the illustrated embodiment, the housing 142 has the shape of a trapezoidal prism, and hence, has four faces 144. However, it is contemplated that the housing 142 may assume any suitable shape, including rectangular and cylindrical shapes, or any other suitable shape for supporting and interfacing with medical accessories 26, 26'. The housing 142 of the mounting apparatus 124 may comprise plastic, metal, such as stainless steel, or a composite material such as, by way of non-limiting example, carbon fiber, or any other material that provides sufficient rigidity to support one or more medical accessories.

The mounting apparatus 124 is configured to couple to the post mount 84' or accessory support mount 122 of the arm assemblies 86, 86' (FIGS. 4A and 5A). Alternatively, the mounting apparatus 124 may replace the post 22 in other configurations and, as such, may be mounted or coupled to the wheeled base 34 (FIG. 1), the headboard 80 of the patient support apparatus 60 (FIG. 2A), or the frame mount 56 of the patient transport chair 38 (FIG. 3B). Moreover, it is contemplated that the accessory support, such as post 22 or mounting apparatus 124, may be mounted or coupled to any location on the patient support apparatus and patient transport chair. Further, the accessory support, such as post 22 or mounting apparatus 124, may be mounted or coupled to any location of any other tables, chairs, beds, and boom stands found within a healthcare facility. In still other embodiments, the mounting apparatus 124 may be coupled to a wall.

With continued reference to FIG. 6A, the mounting apparatus 124 may be configured to rotate about its longitudinal axis AA (not shown extending all the way through mounting apparatus 124 for clarity purposes) relative to the accessory support mount 122 of the arm assembly 86'. This rotation about the longitudinal axis AA can allow the caregiver to orient the different faces 144 of the mounting apparatus 124 as desired depending on the types of interfaces necessary for the medical accessory to be mounted to the mounting apparatus.

Each mechanical interface 146 is configured to mechanically couple one of the medical accessories 26, 26' to the mounting apparatus 124 in a sufficient manner to support the medical accessory 26, 26' on the mounting apparatus 124. In other words, the mechanical interface 146 ensures that the mounting apparatus 124 supports the weight of the medical accessory 26, 26'. In certain embodiments, the mechanical interface 146 can ensure that the medical accessory 26, 26' coupled with the mechanical interface 146 can be lifted, but is otherwise supported. For example, when the medical accessory 26, 26' is coupled with the mechanical interface 146, the mechanical interface 146 may constrain relative moment of the medical accessory 26, 26' to permit only lateral movement (one degree of freedom), upward movement, pivoting upward and downward movement, or lateral movement and pivoting movement, relative to the mounting apparatus 124. This may allow the caregiver to rest the medical accessory 26, 26' on the mounting apparatus 124 and pivot the medical accessory 26, 26' down until the data, power and/or fluid interfaces are engaged without risk of dropping the medical accessory 26, 26'. In other words, the mechanical interface 146 may prevent downward movement (i.e., dropping) of the medical accessory 26, 26'. Moreover, the mechanical interface 146 ensures concurrent movement between the mounting apparatus 124 and the medical accessory 26, 26' attached thereto. This ensures that caregivers can mount one or more medical accessories 26, 26' to the mounting apparatus 124 and the medical accessory 26, 26' will not accidentally become dislodged and fall.

Throughout this disclosure, the term 'support' and its derivatives are used to describe states where some or all of the gravitational forces acting on one or more components are managed through use of other intermediate components. For example, the medical accessory may be supported by the mounting apparatus. Such description should be interpreted to mean that a portion of the gravitational force acting on the medical accessory is transferred to the mounting apparatus. It should be appreciated that, in some cases, the intermediate components may only partially support the weight of other components. For instance, during the process of positioning the medical accessory adjacent the mounting apparatus such that the weight will ultimately be supported wholly by the mounting apparatus. The caregiver and the mounting apparatus may each partially support the weight of the medical accessory. Throughout this disclosure, the term 'supported' should be interpreted to mean 'wholly-supported' and/or 'partially-supported' as described in these exemplary scenarios.

As will be described below, each mechanical interface 146 may be further configured to lock one of the medical accessories 26, 26' into a position relative to the mounting apparatus 124. In such embodiments, the mechanical interface 146 may be configured to support the weight of the medical accessory 26, 26' both in the unlocked arrangement and the locked arrangement.

As will be described in greater detail below, the mechanical interface 146 can be configured in a number of different ways to facilitate releasable coupling of medical accessories 26, 26' to the accessory support, such as the mounting apparatus 124.

In some embodiments, the mechanical interface 146 may be established with a first component and a second component of a coupling system as will be described in further detail below.

The data interface 148 is configured to allow exchange of data between medical accessories 26, 26' coupled to the mounting apparatus 124 and/or the controller of the mounting apparatus 124 that will be described in detail below. In other embodiments, the data interface 148 may be configured to allow exchange of data between medical accessories 26, 26' and the associated patient support apparatus or other device. When one of the medical accessories 26, 26' are placed adjacent to the mounting apparatus 124, the medical accessory 26, 26' may be positioned adjacent to, or in contact with, the data interface 148. The data interface 148 may be configured to allow exchange of data by any suitable transmission modality or protocol between the medical accessory 26, 26', the controller of the mounting apparatus 124, and/or the patient support apparatus. Data transmission may occur using any suitable transmission technique, such as electrical, radio frequency, optical, and combinations thereof. Thus, through the data interface 148, medical accessories 26, 26' can transmit and/or receive various types of information to and/or from the controller, the patient support apparatus or other medical device so as to exchange information, control operation, or otherwise facilitate care of the patient using the medical accessories 26, 26'. For example, infusion pump 26 can communicate data through data interface 148 relating to infusion rate, which can subsequently be transferred to the controller and/or patient support apparatus, and displayed as may be useful on one or more display devices of the patient support apparatus and/or mounting apparatus 124. By way of non-limiting example, the data interface 148 may comprise a Universal Serial Bus (USB) interface, an RFID interface, an optical interface, a serial port interface, a High-Definition Multimedia Interface (HDMI), or IEEE 1394 interface. Still other types of data interfaces are contemplated.

In one embodiment, the data interface 148 may be implemented with a female USB port, and at least one of the medical accessories 26, 26' having a male USB connector that is configured to couple to and engage the female USB port when the medical accessory 26 is placed adjacent to the mounting apparatus 124. Alternatively, the data interface 148 may comprise a cord and plug connection configured to electrically couple the medical accessory 26, 26' to the patient support apparatus and/or controller of the mounting apparatus 124. Alternatively still, the data interface 148 of the mounting apparatus 124 is configured to enable a wireless communication bridge between the controller of the mounting apparatus 124, the patient support apparatus, or other device and the medical accessory 26, such as with Bluetooth, Zigbee, NFC, Wi-Fi, infrared, RFID, or the like. With reference to FIG. 6A, one or more cables 125 may be routed through the swing member 120 and accessory support mount 122 of the arm assembly 86' such that data can be exchanged between the patient support apparatus and the medical accessory 26, 26' via the cables 125.

Figure 13:
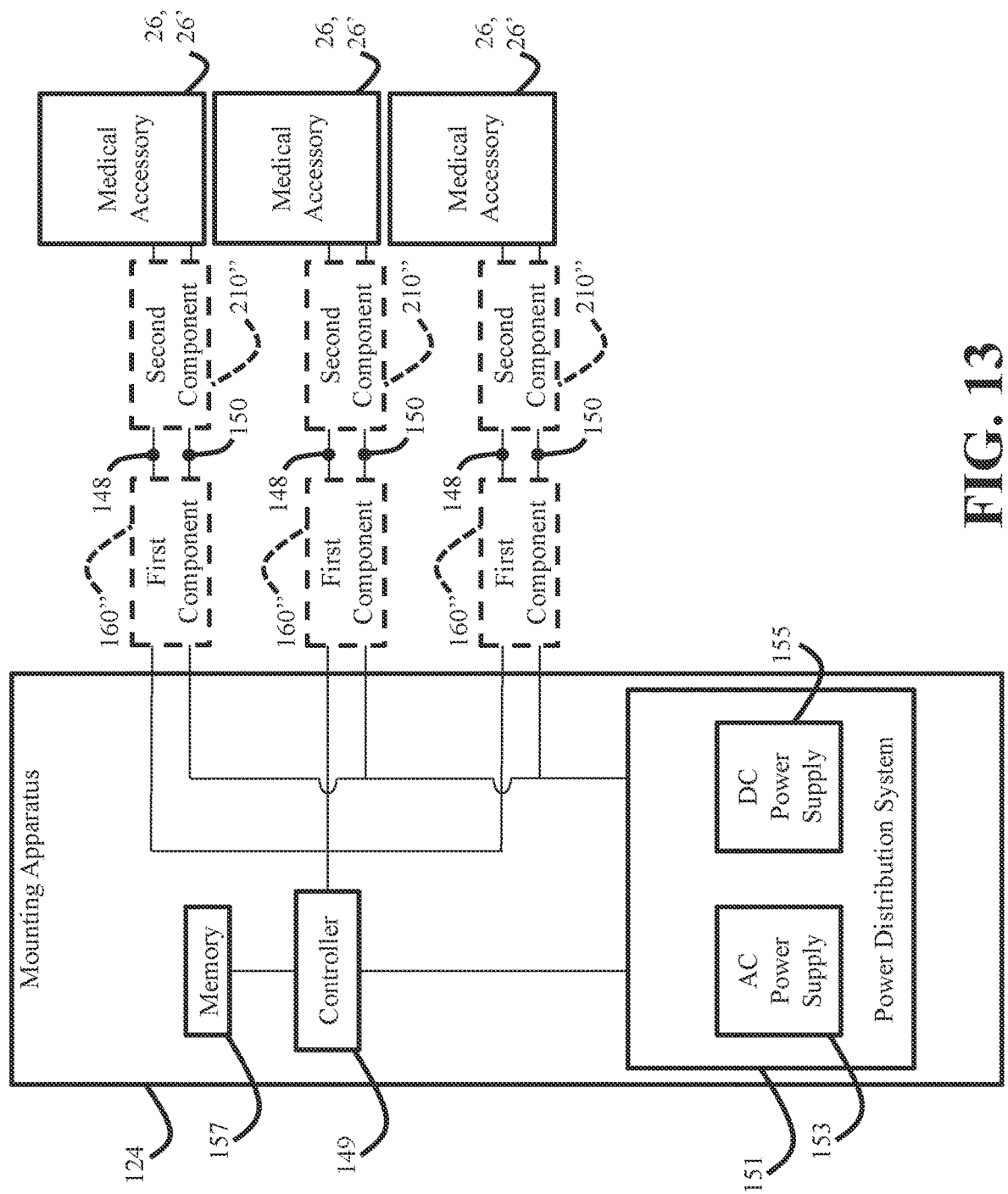
FIG. 13 is an electrical schematic diagram of the mounting apparatus of FIG. 6A with corresponding medical accessories.

With reference to FIG. 13, each power interface 150, if present, is configured to couple medical accessories 26, 26' that are placed adjacent to, or in contact with, the mounting apparatus 124 to a source of electrical power via a power distribution system. Thus, through the power interface 150, the mounting apparatus 124 may provide sufficient operating power to the medical accessory 26, 26' coupled thereto.

With reference to FIG. 13, the power distribution system 151 may be configured to provide direct current (DC) and/or alternating current (AC) to medical accessory 26, 26'. The power distribution system 151 comprises at least one of an AC power supply 153 and a DC power supply 155. In one embodiment, the power distribution system 151 is coupled to the controller 149 of the mounting apparatus 124 and is configured to output AC and/or DC power based on power needs of the medical accessories 26, 26' coupled to the mounting apparatus 124. For example, when multiple medical accessories 26, 26' are coupled to the mounting apparatus 124, the power distribution system 151 may provide AC power to at least one medical accessory 26, 26' and DC power to at least one other medical accessory 26, 26' based on the requirements/configuration of each medical accessory. In some embodiments, the controller 149 may control the power distribution system 151 to selectively supply each medical accessory 26, 26' with AC or DC power based on the identity of each medical accessory 26, 26' as will be described in detail below.

When the power distribution system 151 has only a DC power supply 155, the power distribution system 151 may be referred to as a DC power distribution system. Likewise, when the power distribution system 151 has only an AC power supply 153, the power distribution 151 system may be referred to as an AC power distribution system.

In some instances, the power interface 150 may comprise an AC power interface for providing AC power to the medical accessory 26, 26' from the power distribution system 151. Alternatively, the power interface 150 may comprise a DC power interface for providing DC power to medical accessory 26, 26' from the power distribution system 151.

In one embodiment, the DC power supply 155 is a battery. The battery may be integrated within the mounting apparatus 124. Alternatively, the battery may be disposed onboard the patient support apparatus and may be part of a power system of the patient support apparatus. In such instances, the battery may be coupled to the power interfaces 150 of the mounting apparatus 124 through electrical conductors 127, as shown in FIG. 6A, which are routed through the swing member 120 and accessory support mount 122 of the arm assembly 86'. For example, the electrical conductors 127 may have one end coupled to the power interface 150 and the other end coupled to the power system of the patient support apparatus. The power system of the patient support apparatus may comprise an interface for connecting the battery to an external power supply, such as an electrical outlet, charging station, or the like. Of course, the battery may not be connected to an external power supply, but instead may be readily replaced as the charge depletes. The battery may be primary (non-rechargeable) battery or a secondary (rechargeable) battery.

Furthermore, the power distribution system may comprise an inductive coupler to provide power to the medical accessory 26, 26' at the power interface 150. For example, the power interface 150 and the medical accessory 26, 26' may comprise plates configured with inductive coils whereby electromagnetic induction occurs when the plates are placed in proximity to one another and overlap. When the medical accessory 26, 26' is positioned adjacent to the mounting apparatus 124, the medical accessory 26, 26' may receive power from the inductive coupler. The medical accessory 26, 26' may comprise any suitable components to enable reception of power from the inductive coupler. In certain embodiments, the mounting apparatus 124 may include inductive couplers of various sizes, depending on the power needs of the medical accessories 26, 26'.

It is further contemplated that in some instances the power interface 150 may be configured to provide power for devices other than medical accessories 26, 26' such as, by way of non-limiting example, cell phones, laptops, tablets, and other portable electronic devices. Any of the techniques described herein with respect to the providing power to the medical accessories 26, 26' may apply fully to such other devices.

The fluid interface 152 is configured to couple medical accessories 26 to a source of fluid. Each of the fluid interfaces 152 may be used to provide one of the medical accessories 26, 26' that are placed adjacent to, or in contact with, the mounting apparatus 124 with one or more fluids configured to flow through and move through fluid lines 129 such as one or more liquids or gases. This may be useful when the medical accessory is a respirator assembly that channels oxygen to a patient's airways, where the medical accessory is a pneumatic tool powered by compressed air, or where the medical accessory is an irrigation system that provides water during medical care. By way of non-limiting example, the source of fluid is configured to provide at least one fluid selected from the group comprising a medical gas, a working gas, a liquid for intravenous delivery, a working liquid, and combinations thereof to the medical accessory 26, 26'.

The fluid interface 152 may assume any configuration suitable to provide fluid to the medical accessories 26, 26'. In some instances, the fluid interface 152 comprises one of a male port and a female port such that the one of the male port and the female port are complementary with a fluid port on at least one of the medical accessories 26, 26' such that the medical accessory 26, 26' is coupled to the source of fluid through the fluid interface 152 of the mounting apparatus 124. It is contemplated the source of fluid may be disposed at any suitable location, such as a tank within the mounting apparatus 124, onboard the patient support apparatus, or provided by an adjacent headwall. In certain embodiments the fluid interface 152 of the mounting apparatus 124 may be interconnected to the fluid system of the patient support apparatus. Thus, fluid lines 129 may be routed through the swing member 120 and accessory support mount 122 of the arm assembly 86' to the fluid system of the patient support apparatus.

With continued reference to FIG. 6A, the mechanical interface 146, the data interface 148, the power interface 150, and/or the fluid interface 152 may be arranged in a manner to provide coupling sets 156, which are dedicated to receive one of the medical accessories 26, 26'. Any number of coupling sets 156 may be provided on the mounting apparatus 124 (or the first and second components described below). Furthermore, these coupling sets 156 may be arranged in any suitable manner on the mounting apparatus 124 to provide ease of use and convenience to the caregiver.

In the illustrated embodiment, each coupling set 156 is configured to be engaged directly or indirectly by one of the medical accessories 26, 26'. More specifically, the different interfaces 146, 148, 150, 152 in each coupling set 156 are advantageously spaced and/or oriented to allow coupling of the medical accessory 26 to all interfaces 146, 148, 150, 152 in each single coupling set 156. Additionally, the coupling sets 156 may be spaced and/or oriented about the housing 142 from one another such that a user can easily couple the medical accessories 26 to all of the different coupling sets 156, i.e., the coupling sets 156 are spaced far enough apart such that when a medical accessory 26 is coupled to a first coupling set 156', that medical accessory 26 does not prevent a user from coupling the second medical accessory 26' to a second coupling set 156" adjacent to the first coupling set 156'.

Each coupling set 156 may comprise the power interface 150, the data interface 148, the fluid interface 152, and/or the mechanical interface 146. It is contemplated that certain coupling sets 156 may comprise fewer than all of the mechanical interface 146, the fluid interface 152, the data interface 148, and the power interface 150. This is advantageous as certain medical accessories may not require one or more of a data interface 148, a power interface 150, a fluid interface 152, and a mechanical interface 146. For example, monitors may not require a fluid interface 152 and oxygen bottle holders may not require a power interface 150.

Each coupling set 156 on the mounting apparatus 124 may comprise the mechanical interface 146 in one embodiment. In such a configuration, by coupling the medical accessory 26, 26' to the mechanical interface 146 in the coupling set 156, the medical accessory 26, 26' can be guided into proper engagement with the power interface 150, the data interface 148, and/or the fluid interface 152. For example, if the medical accessory 26 is coupled to the mechanical interface 146, the mechanical interface 146 can ensure that the medical accessory 26, 26' properly aligns with an inductive coupler in the same coupling set 156. As such, the medical accessory 26, 26' can be properly powered by the inductive coupler, by way of sufficient overlap with the inductive coupler, as described above, without interfering with inductive coupler transmission that may exist from other coupling sets 156. If the medical accessory 26, 26' requires engagement with the data interface 148, the mechanical interface 146 can ensure that the medical accessory 26, 26' properly aligns with the data interface 148 such that the medical accessory 26, 26' can effectively transfer data through the data interface 148.

With reference to FIG. 13, the controller 149 may include one or more processors, or microprocessors, for processing instructions stored in memory 157 to control operation of the patient support apparatus and/or medical accessories. Such instructions may be any of the functions, algorithms or techniques described herein performed by the controller 149. Additionally or alternatively, the controller 149 may comprise one or more microcontrollers, field programmable gate arrays, systems on a chip, discrete circuitry, and/or other suitable hardware, software, or firmware that is capable of carrying out the functions described herein. The controller 149 may be carried on-board the mounting apparatus 124 or patient support apparatus. Alternatively, the controller 149 may be located remote from the mounting apparatus 124 and the patient support apparatus, and communicate with the mounting apparatus 124 and/or patient support apparatus through a wired or wireless connection. In one embodiment, the controller 149 is disposed within the housing of the mounting apparatus 124. In other embodiments, the controller 149 is mounted to the faces 144 of the mounting apparatus 124. The controller 149 may comprise one or more subcontrollers configured to control the patient support apparatus and/or all of the medical accessories 26, 26' coupled to the mounting apparatus 124, collectively. Alternatively, the controller 149 may comprise one or more subcontrollers for the patient support apparatus individually, and for certain types of medical accessories 26, 26' coupled to the mounting apparatus 124.

The controller 149 may receive data from the patient support apparatus and/or medical accessories 26, 26' via the data interface 148. While the mounting apparatus 124 in the illustrated embodiment is shown to include the memory 157, controller 149, and power distribution system 151, it should be appreciated that the patient support apparatus may similar components and function in a similar manner. The data received from the patient support apparatus and/or medical accessories 26, 26' may include patient data obtained by the patient support apparatus and/or medical accessories 26, 26', and operating parameters of the patient support apparatus and/or medical accessories 26, 26'. The patient data may include, by way of non-limiting example, blood pressure, temperature, pulse rate, respiratory rate, blood oxygen saturation level, patient weight, etc. The operating parameters may include, by way of non-limiting example, medical accessory ID, input voltage, input current, medical accessory status, output power, temperature, etc.

The controller 149 may be configured to control supply of at least one of AC power and DC power from the power distribution system 151 of the mounting apparatus 124 to a medical 26, 26' accessory coupled thereto. The medical accessory 26, 26' may be coupled to the mounting apparatus 124 such that the medical accessory 26, 26' is supported by the mounting apparatus 124 to establish both the data interface 148 and the power interface 150. In other embodiments, the medical accessory 26, 26' may be coupled to, supported by, and electrically coupled to the mounting apparatus 124 via the first and second components 160", 210" of the coupling system to establish a data and power interface as will be described in further detail below.

The controller 149 may be configured to communicate with the medical accessory 26, 26' to determine how to appropriately power the medical accessory 26, 26'. For example, the controller 149 may determine whether medical accessory 26, 26' is configured to accept AC or DC power. Determining whether the medical accessory 26, 26' is configured to accept AC or DC power may further comprise communicating data indicative of the type of power required by the medical accessory 26, 26' between the medical accessory and the controller 149 through the data interface 148.

In some embodiments, the controller 149 may determine the identity of the medical accessory 26, 26' for power configuration and selection purposes. The identity may be any characteristic or data that is indicative of the characteristics or electrical requirements of that medical accessory 26, 26'. For example, the controller 149 may determine a serial number or unique ID of the medical accessory, and based on that identity, determine the input voltage, input operating frequency, and/or input current required by the medical accessory 26, 26'. This communication can be established between the medical accessory and the controller 149 through the data interface 148 or other accessory support.

When the controller 149 determines the medical accessory 26, 26' identity, the controller 149 may compare the medical accessory ID to a look-up table stored in the memory 157 to determine the electrical requirements of that medical accessory 26, 26'. In other examples, the controller 149 may determine the electrical requirements of the medical accessory 26, 26' on-the-fly using analytical techniques. For example, the controller 149 may enable the medical accessory 26, 26' to consume power initially by enabling the power distribution system 151 to provide such power having characteristics with variable range. Depending on the actual power and characteristics of power consumed by the medical accessory 26, 26', the controller 149 may detect such characteristics and instruct the power distribution system 151 to provide power having characteristics commensurate with the detected actual power consumed by the medical accessory 26, 26'. This may be done without storing information about the medical accessory 26, 26' in memory 157. However, once the power characteristics are detected, the controller 149 may store the detected characteristics in memory 157 for later use.

Any communication protocol suitable to exchange data between the medical accessory 26, 26' and the controller 149 may be used. By way of non-limiting example, a 1-wire communication protocol may be used over the data interface to communicate the data indicative of the type of power required by the medical accessory between the medical accessory 26, 26' and the controller 149. In this manner, the controller 149 can determine the medical accessory 26, 26' and the type of power required by the medical accessory 26, 26' while the medical accessory 26, 26' is not powered. Of course, such communication protocols may be used to transmit data for purposes other than determining the type of power required by the medical accessory 26, 26'.

Once the controller 149 determines whether the medical accessory 26, 26' is configured to accept AC or DC power based on the identity of the medical accessory, the controller 149 is configured to control the power distribution system 151 to supply the medical accessory 26, 26' with AC and DC power from the AC or DC power supplies 153, 155 of the power distribution system 151. In some embodiments, when the medical accessory 26, 26' is mechanically coupled to, supported by, and electrically coupled (i.e., power and data interfaces established) to the mounting apparatus 124 via the first and second components 160",210" of the coupling system, the controller 149 may supply power from power distribution system 151 via the power interfaces of the first and/or second components 160",210".

Similarly, the controller 149 may control the power distribution system 151 to supply the medical accessory 26, 26' with the appropriate input voltage and/or input current in accordance with the data indicative of the voltage and/or current required by the medical accessory 26, 26'. It should be appreciated that some medical accessories may be configured to only accept one type of power, i.e., AC or DC, and in some cases, certain medical accessories contemplated for use with this system may be free from an AC-DC converter. For example, the coupling system may include two or more medical accessories, one being free from an AC-DC converter and one including an AC-DC converter.

Figure 22:
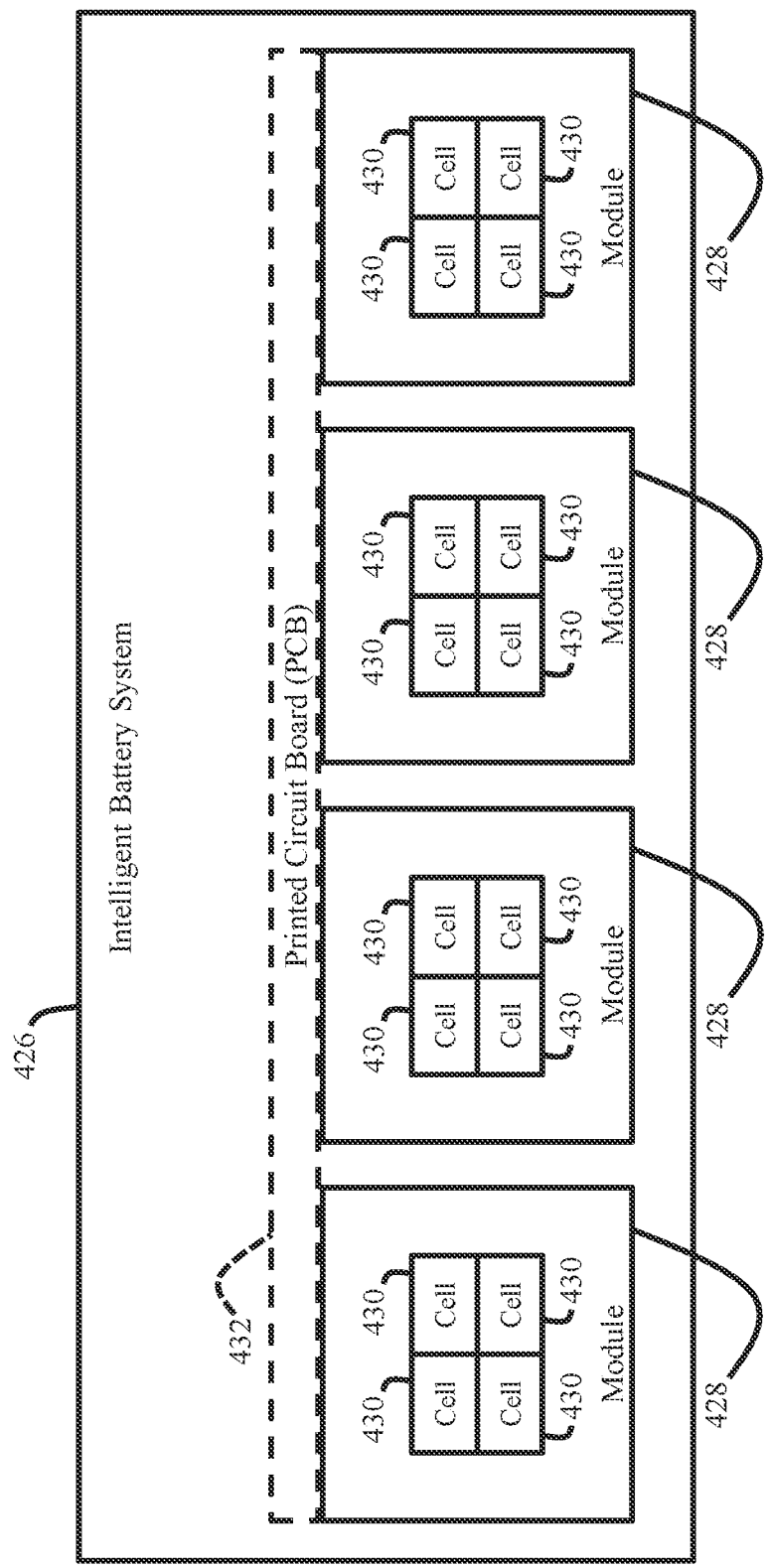
FIG. 22 is a schematic diagram of an intelligent battery system.

As described above, DC power may be supplied to medical accessories 26, 26' from the power distribution system 151 via the battery. With reference to FIG. 22, in some embodiments, the battery may be part of an intelligent battery system 426. The intelligent battery system 426 may comprise two or more battery modules 428. By way of non-limiting example, the intelligent battery system 426 may comprise from one to ten, from two to eight, or from four to six battery modules, such as 12V battery modules. In some embodiments, the battery system comprises four 12V battery modules 428.

As shown in FIG. 22, each battery module 428 comprises at least one cell 430. In the illustrated embodiment, each battery module 428 comprises four cells 430, with the cells 430 being connected in series. Alternatively, the cells 430 may be connected in parallel or series and parallel.

The battery modules 428 may be connected in series, parallel, or series and parallel based on the voltage and current requirements of the medical accessories coupled to the mounting apparatus. The intelligent battery 426 system may be coupled to the controller to provide various levels of DC voltage depending on the requirements of the medical accessory. For example, if the controller determines that the medical accessory requires 12V, then the controller will ensure that the intelligent battery system 426 supplies 12V to the medical accessory. If the controller determines that the medical accessory requires 48V, the controller will ensure that the intelligent battery system 426 supplies 48V from the intelligent battery system 426 to the medical accessory. Of course, it is contemplated that each battery module may be configured at various voltages other than 12V.

In some embodiments, the intelligent battery 151 system may comprise a printed circuit board (PCB) 432 configured to selectively connect the battery modules 428 in series, parallel, or series and parallel.

In other embodiments, the intelligent battery system may comprise a regulator that up-converts or down-converts the voltage output by the battery modules based on the requirements of the medical accessory.

Referring again to FIG. 13, the controller 149 may control the power distribution system 151 to supply power from each battery module of the intelligent battery system to each medical accessory coupled to the mounting apparatus 124. For example, if the controller 149 determines that three medical accessories are coupled to the mounting apparatus that each require 12V, then the controller 149 may control the power distribution system 151 to supply power to each medical accessory from a separate 12V battery module of the intelligent battery system.

Likewise, the controller 149 may determine the electrical current or frequency requirements of each medical accessory and control the power distribution system 151 to vary the electrical current or frequency of power supplied to the medical device from the intelligent battery system based on the determined requirements.

In other embodiments, the medical accessory 26, 26' coupled to the mounting apparatus 124 may be a battery. When the medical accessory 26, 26' is the battery, the battery may be in communication with the power distribution system 151 such that the battery supplements and/or enhances the power distribution system 151. In this manner, the controller 149 may control the battery to supply power to other medical accessories coupled to the mounting apparatus 124 via the power distribution system 151. Moreover, the controller 149 may control the power distribution system 151 to supply power to the other medical accessories by some combination of the battery coupled to the mounting apparatus 124 and the AC and/or DC power supplies 153, 155. Thus, the controller 149 may control the power distribution system 151 to supply power to the other medical accessories by only the battery coupled to the mounting apparatus 124, only the AC and/or DC power supplies 153, 155, or both the battery coupled to the mounting apparatus 124 and the AC and/or DC power supplies 153, 155.

In some embodiments, the controller 149 is configured to monitor the operating parameters of the patient support apparatus and/or medical accessories coupled to the mounting apparatus 124 while they are supplied with power by the power distribution system 151. The controller 149 may be configured to compare the operating parameters such as, by way of non-limiting example, medical accessory status, temperature, and/or output power, to predetermined threshold values such that if one or more of the predetermined threshold values has been reached or exceeded, the controller 149 controls the power distribution system 151 to cease supplying power to the patient support apparatus and/or medical accessories. The predetermined threshold values may be stored in the memory 157 of the mounting apparatus 124. In some embodiments, in response to one or more of the predetermined threshold values being reached or exceeded the controller 149 may control the power distribution system 151 to vary the input voltage and/or input current until the operating parameters drop below the predetermined threshold values. In still other embodiments, in response to one or more of the predetermined threshold values being reached or exceeded, the controller 149 may output a signal to alert the caregiver that the medical accessory requires maintenance. The alert may be audible and/or visual such as, for example, a visual alert displayed on a display unit that will be described in detail below.

It is further contemplated that the mounting apparatus may comprise a display unit (not shown). The display unit may comprise a touchscreen display screen and/or buttons on a housing around a display screen. The display unit may be operable to display patient data and a plurality of icons that are selectable using capacitive touch to control the patient support apparatus and/or medical accessories. The patient data may correspond to data communicated to the display unit from the controller. In some embodiments, the display unit may be operable to the display the patient data and the plurality of icons at the same time. In other embodiments, the display unit may be operable to display the patient data and the plurality of icons at different times. When buttons are provided on the housing around the display screen, the buttons may control dedicated functions of the patient support apparatus and/or medical accessories that are coupled to the mounting apparatus. In some embodiments, the functions associated with the buttons may change in response to changes to the information shown on the display screen. In such embodiments, indicia regarding active functions currently associated with the buttons may be shown on the display screen near the buttons.

The display unit may be coupled to the mounting apparatus by the mechanical interface, the data interface, and/or the power interface described above, or optionally with the first and second components described below. In this manner, the display unit may be mechanically coupled to the mounting apparatus, receive data from the patient support apparatus and/or medical accessories coupled to mounting apparatus, and electrically powered by the mounting apparatus. In some embodiments, the display unit may be mechanically coupled to the mounting apparatus by an adjustable display arm. The adjustable display arm can be a tilt and swivel arm. In other variations, the display unit can be integrated into one of the faces of the mounting apparatus.

In some embodiments, the display unit be positioned at other locations, such as on the patient support apparatus. When the display unit is on the patient support apparatus, the display unit may be used to control the medical accessories coupled to the patient support apparatus and/or mounting apparatus.

It should be appreciated that the display unit and/or other medical accessories may be mounted to the mounting apparatus with a torque limiting feature. When present, the torque limiting feature prevents damage to the medical accessories caused from inadvertent collisions therewith. In other words, if the caregiver is pushing the mounting apparatus down a corridor and the display mounted thereto accidentally catches a doorway or other obstacle, the torque-limiting feature will allow some give such that the display unit can flex relative to the mounting apparatus to prevent damage to the mounting device or the display unit. Various torque-limiting features are contemplated, including clutches, dampers, etc.

Figure 6B:
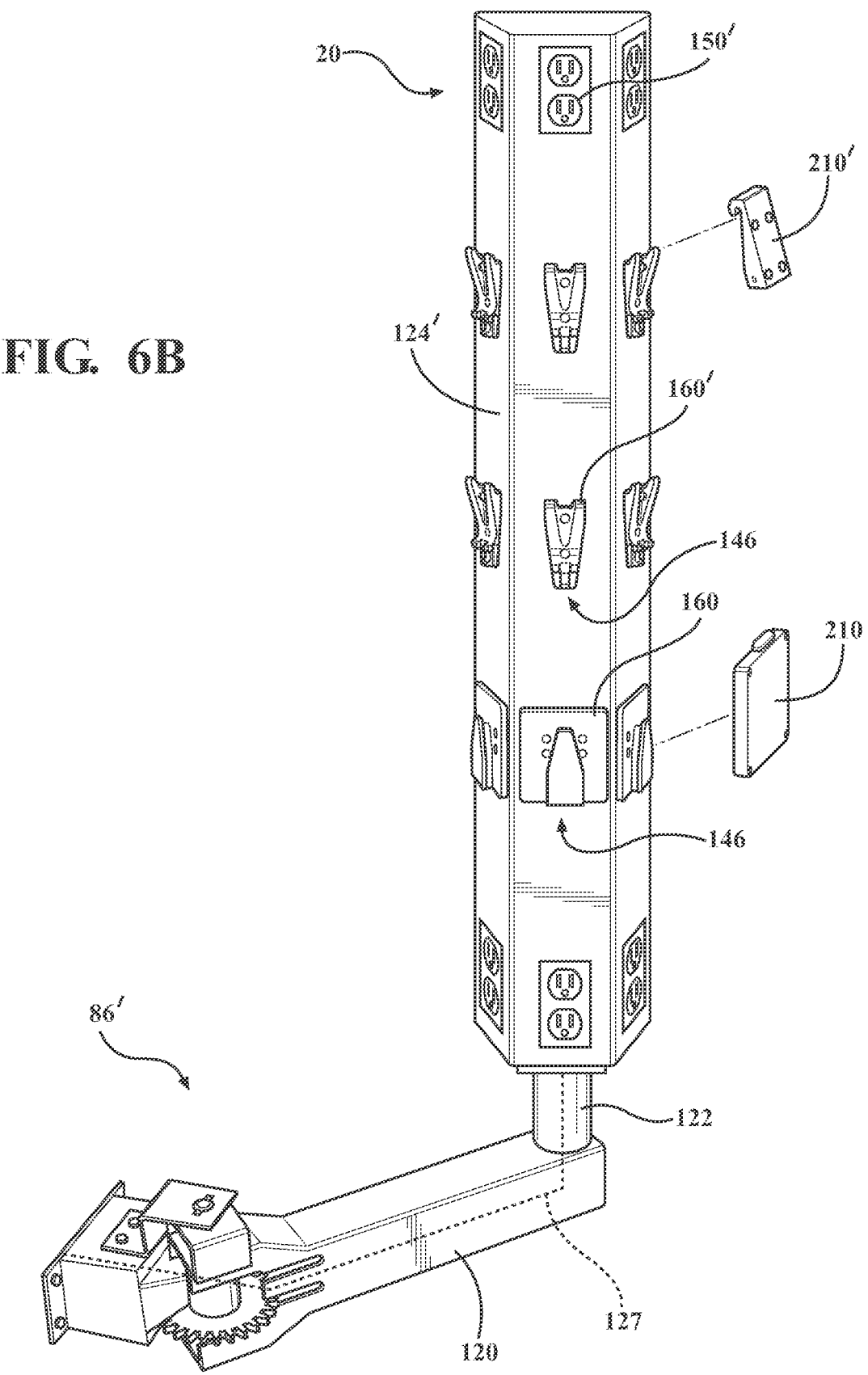
FIG. 6B is a perspective view of the accessory support of FIG. 5C, shown having exemplary power and mechanical interfaces, arranged on first, second, and third faces.

As shown in FIG. 6B, another embodiment of the mounting apparatus 124' is shown with AC power outlets 150' as exemplary power interfaces 150. Furthermore, exemplary mechanical interfaces 146 are shown as first components which will be described in detail below. The first components 160, 160' are generally configured to be engaged by second components 210, 210', which may be coupled or mounted to the medical accessory. Thus, if the medical accessory is coupled to either of first components 160, 160', with the second components 210, 210', the medical accessory will be supported by the first component 160, 160', and be provided power via the associated AC power outlet 150'.

Figure 6C:
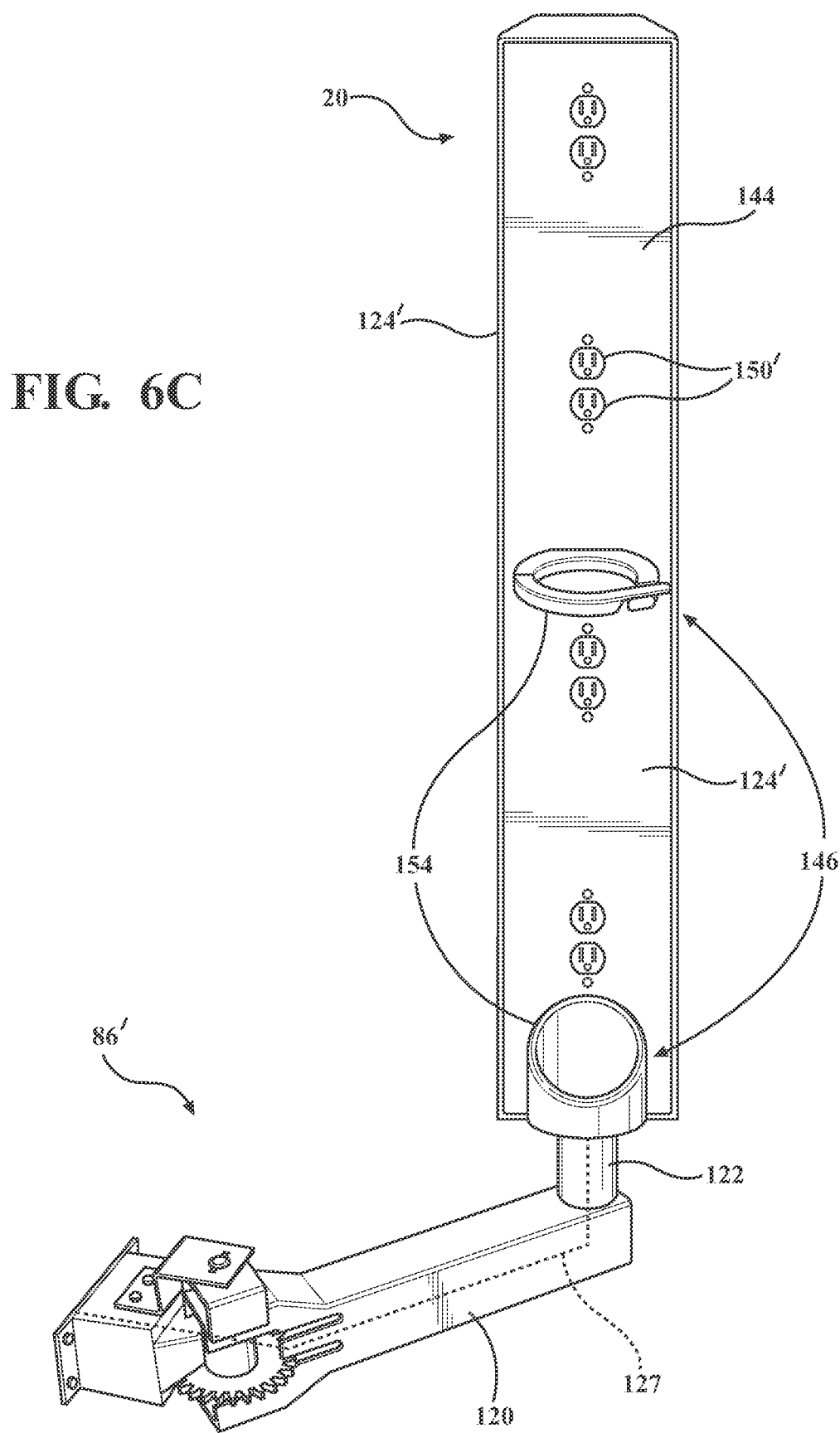
FIG. 6C is an alternate perspective view of the accessory support of FIG. 6B, showing an oxygen bottle holder and AC outlets arranged on a fourth face.

As shown in FIG. 6C in one embodiment, the mechanical interface 146 comprises a gas tank holder 154 coupled to another one of the faces 144 of the mounting apparatus 124. When present, the gas tank holder 154 provides a quick and efficient manner of coupling a gas source that is separable from the mounting apparatus 124.

Figure 6D:
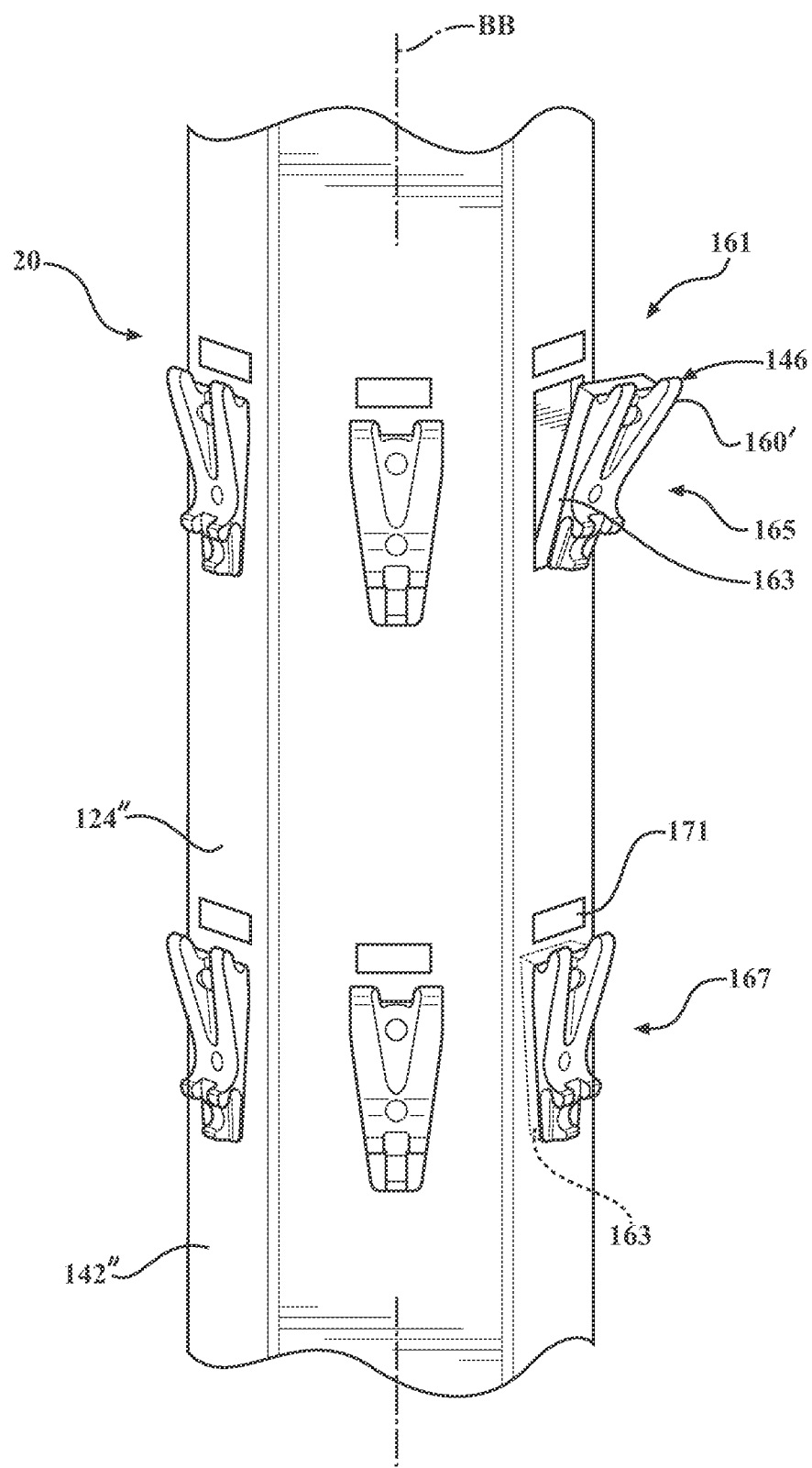
FIG. 6D a partial perspective view of the accessory support of FIG. 6B having deployment devices.

With reference to FIG. 6D in the illustrated embodiment, accessory support 20, such as the mounting apparatus 124", (or the first/second component) may comprise a deployment device 161 coupled to the mounting apparatus 124" and the mechanical interface 146, such as the first component 160', and configured to move a portion of the mechanical interface 146 relative to the mounting apparatus 124" between a deployed state and an undeployed state. The deployment device 161 may comprise an actuator, such as an electric motor, configured to move the first component 160' relative to the mounting apparatus 124". The deployment device 161 may further comprise a mount section 163 coupled to the first component 160'. In the illustrated embodiment, the mount section 163 is configured to move the first component 160' to the mounting apparatus 124". It is to be appreciated the mount section 163 may movably couple any of the other interfaces to the mounting apparatus 124", i.e., the power interface, the fluid interface, and the data interface.

As described above, the deployment device 161 is configured to move the mount section 163 between a deployed state, shown generally at 165, and an undeployed state, shown generally at 167. When the deployment device 161 is in the deployed state 165, the mount section 163 extends outward from the mounting apparatus 124" to facilitate coupling between the first component 160' and the second component 210'. In the illustrated embodiment, the mount section 163 pivots outward from the outermost face of the mounting apparatus 124". The type of movement that the deployment device 161 may provide is not particularly limited, and the deployment device 161 may move the mount section 163 in any suitable manner to facilitate coupling to the medical device, such as pivoting from any edge of the mounting apparatus 124", sliding the mount section 163 outward from the mounting apparatus 124", etc.

When the deployment device 161 is in the undeployed state 167, the mount section 163 may be substantially parallel, or parallel, to a longitudinal axis BB of the mounting apparatus 124". Thus, the deployment device 161 has a reduced dimensional profile in the undeployed state 167 when compared to the deployed state 165. The deployed state 165 facilitates coupling between mechanical interface 146 and the medical accessory by presenting an advantageous orientation of the mechanical interface. The deployment device 161 may be retained in the undeployed state using suitable locking or detent mechanisms.

In illustrated embodiment, the housing 142" of the mounting apparatus 124" defines a deployment device recess 169 configured to receive the mount section 163 such that the mount section 163 is substantially flush, or flush, with the outer surface of housing 142" of the mounting apparatus 124" when the deployment device 161 is in the undeployed state 167. It is also contemplated that the mount section 163 may not be substantially flush, nor flush, with the housing 142" of the mounting apparatus 124" when the deployment device 161 is in the undeployed state 167.

With reference to FIG. 6D when the deployment device 161 is present, the mounting apparatus 124" may further comprise a user input device 171. Actuation of the user input device 171 causes the deployment device 161 to move between the deployed state 165 and the undeployed state 167. By way of non-limiting example, the user input device 171 may be a button. In other still other embodiments, the user input device 171 may be a voice actuation device. It is further contemplated the user input device 171 may also be selected from the group consisting of a motion sensor, a button, a voice actuation device, and combinations thereof.

Alternatively, the deployment device 161 or mounting apparatus may comprise a proximity sensor that may detect a medical accessory within a predetermined proximity of deployment device 161. Thus, when the medical accessory is within the predetermined proximity of the deployment device 161 or mounting apparatus, the deployment device 161 moves from the undeployed state 167 to the deployed state 165. Conventional proximity sensors, such as infrared sensors, may be used.

Referring to FIG. 7A in one exemplary embodiment, the medical accessory 26 comprises a line coupler assembly 162. This line coupler assembly 162 may couple to any of the aforementioned accessory supports, including the mounting apparatus described immediately above. During the course of treatment, it is possible that several intravenous lines may be necessary to deliver fluids to a patient. In addition, a number of medical accessories and their corresponding electrical cords may be required for treatment of the patient. The number of electrical cords and intravenous lines in proximity of the patient and the patient support apparatus may be difficult for the caregiver to navigate.

Figure 7B:
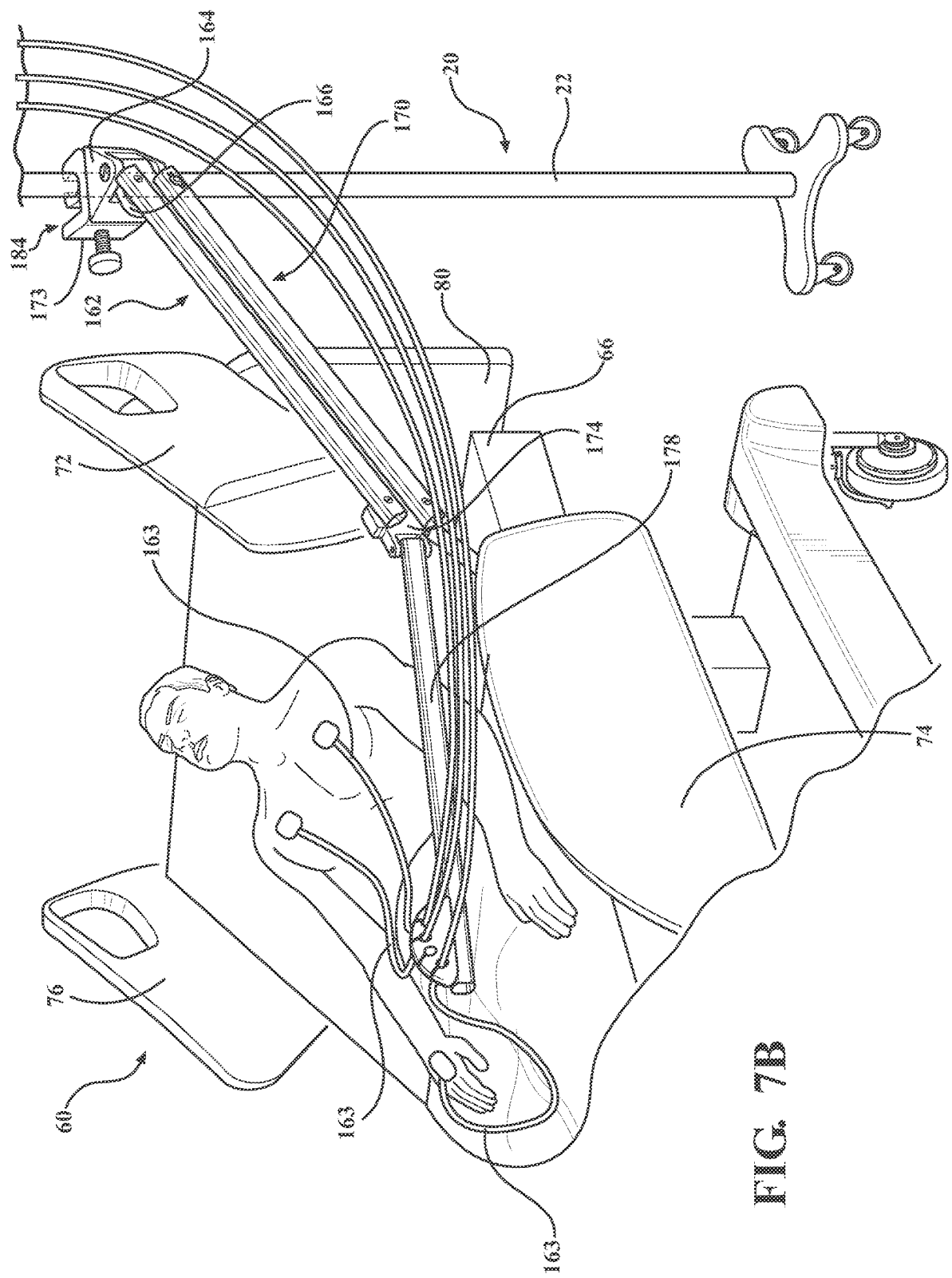
FIG. 7B is a perspective view of the line coupler assembly of FIG. 7A coupled to the accessory support of FIG. 1, and position adjacent another exemplary patient support apparatus.

As shown in FIG. 7B, the line coupler assembly 162 is configured to couple to one or more lines 163 common to the healthcare facility such that caregivers can position the lines as desired, effectively removing the safety concern as described above. The lines 163 may comprise intravenous conduits, cables, and cords. These lines 163 may be coupled to suitable medical accessories, including oxygen tanks, infusion pumps, heart monitors, intravenous fluid containers and other medical accessories.

The line coupler assembly 162 may be configured to attach to any suitable location on the patient support apparatus 60 including, but not limited to, the headboard 80, footboard, one or more side rails 72, 74, 76, the intermediate frame 66, and the like. Alternatively, the line coupler assembly 162 may be coupled to accessory support 20, such as the post 22 or the mounting apparatus described above. Of course, it is further contemplated two or more line coupler assemblies 162 may cooperate to control the lines 163.

Figure 7C:
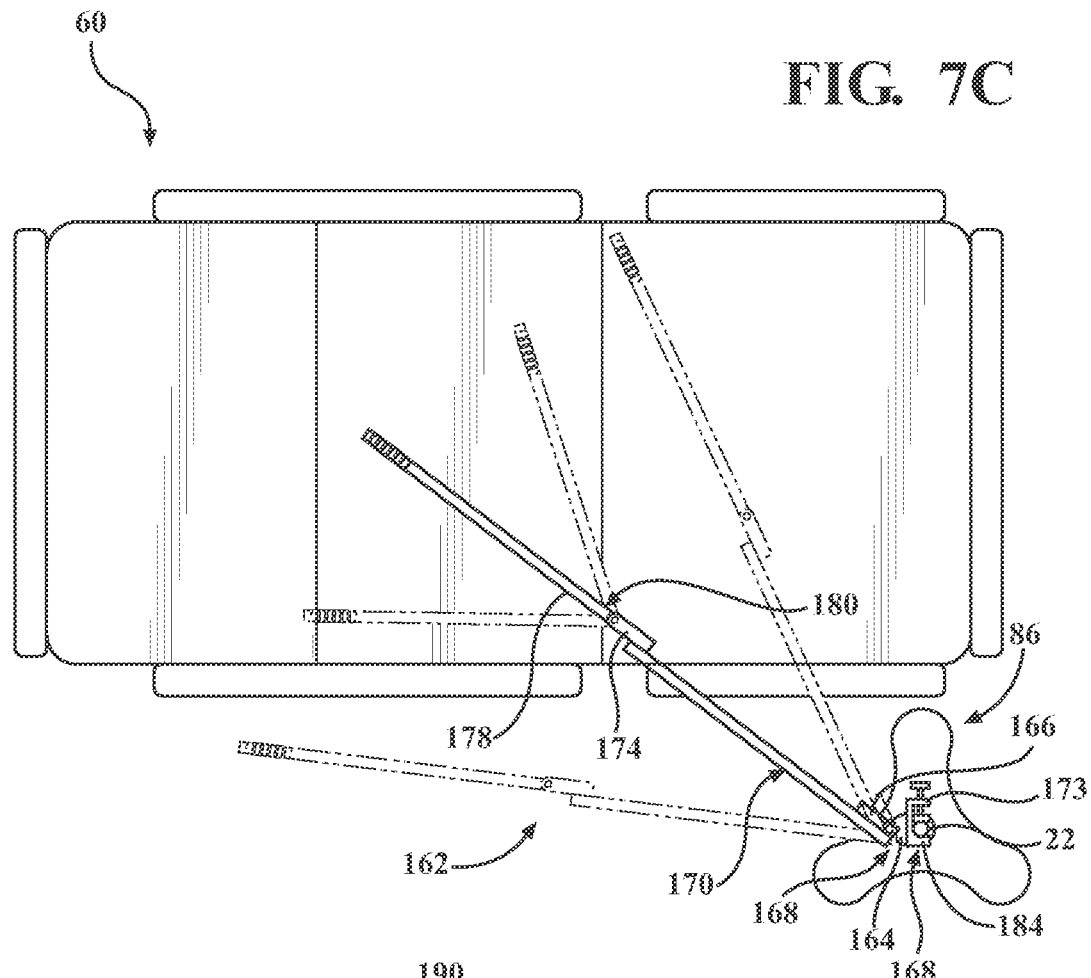
FIG. 7C is a top-side view of the lien coupler assembly of FIG. 7B, depicting representative positions within a range of motion of the line coupler assembly in phantom adjacent to the patient support apparatus.

With reference to FIGS. 7A-7C in the illustrated embodiment, the line coupler assembly 162 comprises an attachment hub 164. The attachment hub 164 cooperates with a first arm section 166 to form a first joint 168. The first arm section 166 has a proximal end adjacent the attachment hub 164 and a distal end opposite the adjacent end. The distal end of the first arm section 166 cooperates with a proximal end of a second arm section 170 to form a second joint 172. A distal end of the second arm section 170 located opposite the proximal end of the second arm section 170 cooperates with a proximal end of a third arm section 174 to form a third joint 176. A distal end of the third arm section 174 located opposite the proximal end of the third arm section 174 cooperates with a proximal end of a fourth arm section 178 to form a fourth joint 180. A line coupler 182 is coupled to a distal end of the fourth arm section 178, located opposite the proximal end of the fourth arm section 178. It should be appreciated that the arm sections 166, 170, 174, 178 and the joints 168, 172, 176, 180 may assume a number of different configurations. Furthermore, it should be appreciated that the line coupler assembly 162 may comprise additional arm sections and/or joints may be included depending on the length and positionability desired.

With reference to FIG. 7A, in the illustrated embodiment, the first joint 168 and the fourth joint 180 enable only lateral rotational movement relative to the adjacent arm sections, whereas the second joint 172 and the third joint 176 provide for only vertical pivotal movement relative to the adjacent arm sections. It should be appreciated that other joint configurations are also contemplated such that the movement allowed by the various joints be interchangeable, i.e., the first joint 168 may enable any vertical movements in certain embodiments. Through the complementary ranges of motion provided by the various joints 168, 172, 176, 180, the distal end of the arm assembly can move into any desired position in both vertical and lateral dimensions, relative to the patient support apparatus 60 or the accessory support 20.

With reference to FIG. 7A, as depicted, the second arm section 170 and the fourth arm section 178 are longer than the first arm section 166 and the third arm section 174. However, it is contemplated that the arm sections may assume any suitable length. In other words, it is contemplated that the first and third arm 166, 174 sections be longer than the second and fourth arm sections 170, 178.

With reference to FIG. 7B in the illustrated embodiment, the attachment hub 164 is fastened to a mounting device 184. The mounting device 184 can be releasably coupled to the accessory support 20, such as post 22. In the illustrated embodiment the mounting device 184 comprises a screw clamp 173. It should be appreciated that the attachment hub 164 can be coupled to any suitable mounting device 184, such as those that will be described below. Alternatively, the attachment hub 164 may be configured to couple directly to the first component of the mechanical interface described above.

Figure 7D:
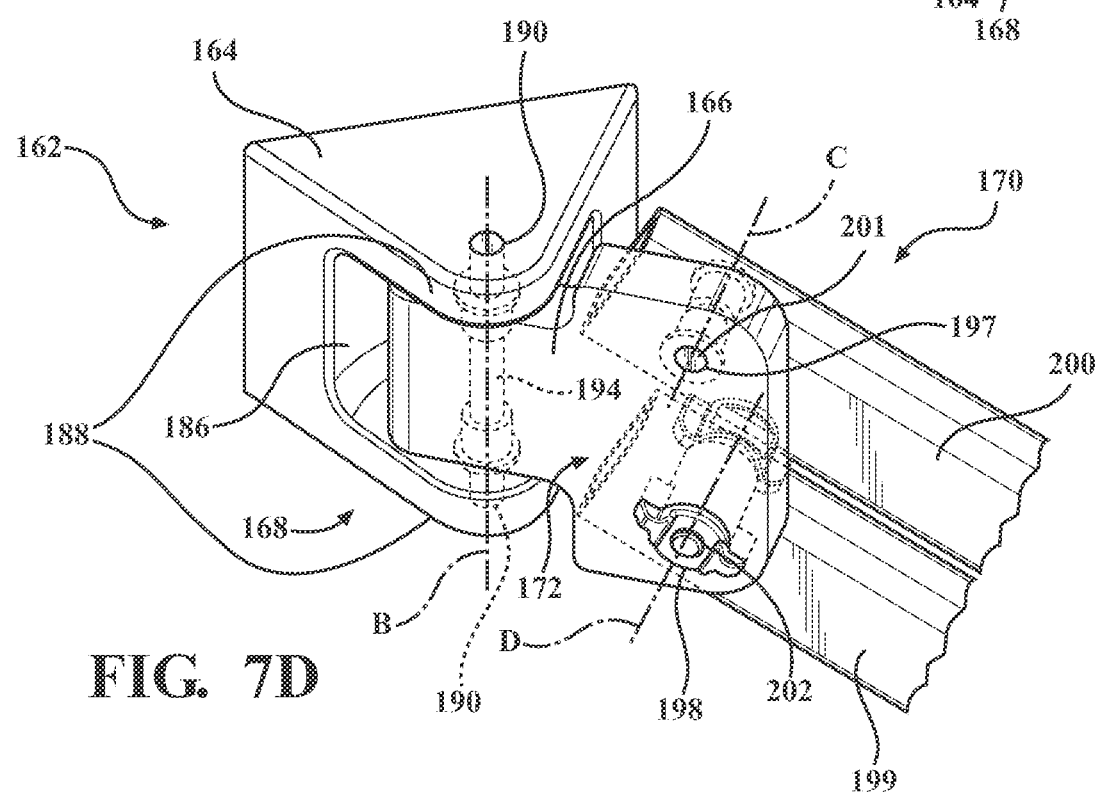
FIG. 7D is a partial perspective view of a first joint of the line coupler assembly of FIG. 7A.

As shown in FIG. 7D in the illustrated embodiment, the attachment hub 164 comprises an attachment hub channel 186 defined by two attachment hub protrusions 188. Both protrusions 188 define attachment hub apertures 190 that are coaxial with respect to each other. In the illustrated embodiment the proximal end of the first arm section 166 comprises a bore. A first pivot pin 194 is disposed within apertures of attachment hub 164 and bore of the first arm section 166 to define a pivot axis B such that the attachment hub 164 is rotatably coupled to the first arm section 166 to form the first joint 168.

In some instances, the attachment hub 164 comprises a lock feature to prevent rotation of the first arm section 166 about the pivot axis B. Alternatively, a friction device such as a clutch may be disposed within the attachment hub apertures 190 of the attachment hub 164 and bore such that the attachment hub 164 is rotatably coupled to the first arm section 166. When present the friction device couples the attachment hub 164 to the first arm section 166 such that in order for the first arm section 166 to be rotated with respect to the attachment hub 164, a force that is greater than that exerted as a result of unintentional contact with the line coupler assembly 162 is required (i.e., the first arm section 166 will remain stationary unless a person, such as the caregiver, intentionally moves the first arm section 166). It is contemplated that the friction device may be configured to provide any amount of frictional force desired.

The exemplary first arm section 166 comprises two first arm section apertures 197, 198 that extend from the first face to the second face. The second arm section 170 comprises a clutch arm 199 and a support arm 200. While it is further contemplated that only a single arm could be utilized, the use of two arms 199, 200 may be useful to provide increased structural rigidity for the line coupler assembly 162. It is further contemplated that more than two arms may be utilized. In addition, the second arm section 170 may comprise other forms other than those explicitly described.

The proximal ends of the clutch arm 199 and the support arm 200 each define a bore. A second pivot pin 201 is disposed within the first arm section aperture 197 and the bore of the support arm 200 to form a pivot axis C and form a second joint 172. Similarly, a friction device 202 is disposed within the first arm section aperture 198 and the bore of the clutch arm 199 to define a pivot axis D for the clutch arm 199. In this manner, the first arm section 166 and the second arm section 170 are pivotably coupled to allow vertical movement of the second arm section 170 relative to the first arm section 166.

The friction device 202 is disposed in the bore of the clutch arm 199 such that in order for the second arm section 170 to be moved vertically relative to the first arm section 166, a force that is greater than the force exerted by gravity on the second arm section 170 is required (i.e. the second arm section 170 will remain stationary unless a person, such as the caregiver, intentionally moves the second arm section 170). This friction device 202 advantageously enables the caregiver to place the second arm section 170 at a desired height and release it, while retaining the position of the second arm section 170. In the illustrated embodiment, the friction device 202 is a friction torque hinge. However, it should be appreciated that the friction device 202 may assume other suitable configurations and provide sufficient resistance to movement to prevent accidental repositioning of the second arm section 170.

Figure 7E:
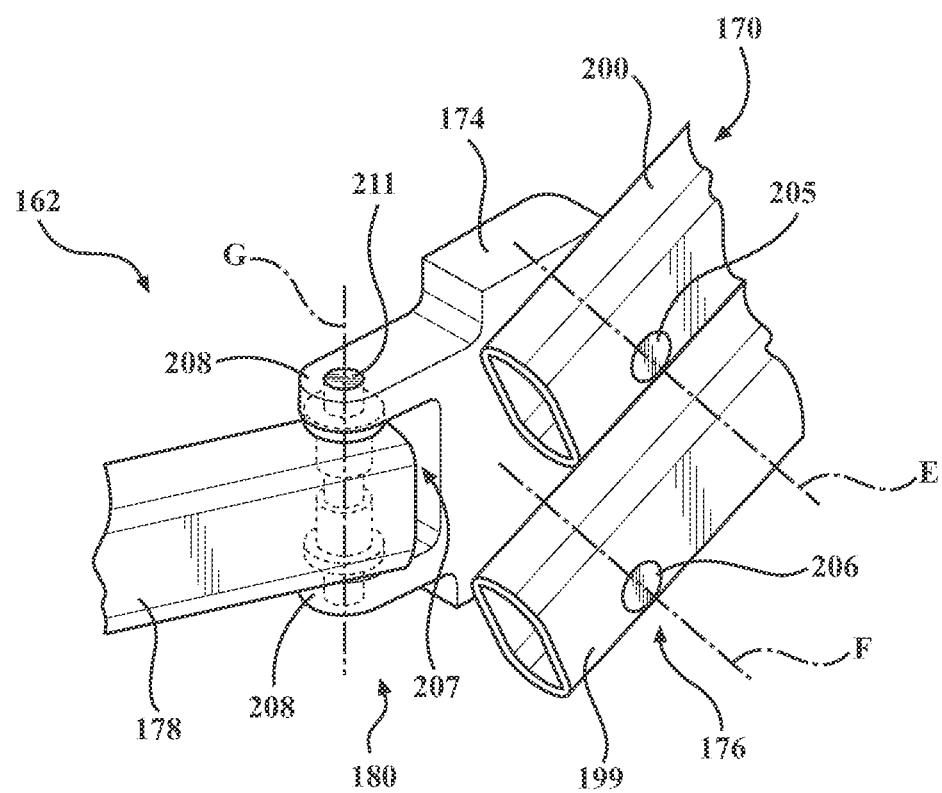
FIG. 7E is a partial perspective view of a third joint of the line coupler assembly of FIG. 7A.

Referring to FIG. 7E in the illustrated embodiment, the distal end of the second arm section 170 is coupled to the proximal end of the third arm section 174. As illustrated, the distal ends of the clutch and support arms 199, 200 each define a bore. The proximal end of the third arm section 174 comprises two apertures. Third and fourth pivot pins 205, 206 are disposed within the bores of the support arm 200 and the clutch arm 199 and the third arm section apertures to pivotably couple the second arm section 170 to the third arm section 174 and form the third joint 176. In this manner, the third arm section 174 can move vertically relative to the second arm section 170 about pivot axes E, F defined by the third and fourth pivot pins 205, 206. In some instances the friction device 202 described above may be used in place of the third and fourth pivot pins 205, 206. It is further contemplated that third joint 176 may comprise a lock feature configured such that these arm sections can no longer be rotated freely about the pivot axes E, F.

The depicted configuration of first, second, and third arm sections 166, 170, 174 establishes a four-bar linkage between the first arm section 166 and the third arm section 174. Other linkage configurations are also contemplated through interaction of the arm sections 166, 170, 174.

As shown in FIG. 7E, the distal end of the third arm section 174 comprises a channel 207 defined by protrusions 208. Each protrusion 208 comprises an aperture. The proximal end of the fourth arm section 178 comprises a bore. In the illustrated embodiment a fifth pivot pin 211 may be disposed within the apertures of the distal end of the third arm section 174 and the bore of the fourth arm section 178 to define a pivot axis G such that the third and fourth arm sections 174, 178 are rotatably coupled to one another to form the fourth joint 180.

With reference to FIG. 7A, the line coupler 182 is coupled to the distal end of the fourth arm section 178. While it is shown that the line coupler 182 is fixedly mounted to the fourth arm section 178, other suitable couplings are contemplated; for example, the line coupler 182 may be movably mounted on the fourth arm section 178. It is further contemplated that the fourth arm section 178 may comprise multiple line couplers 182, or that the line coupler 182 may be coupled to other portions of the line coupler assembly 162, such as the first 166, second 170, third arms sections 174, and combinations thereof.

Figure 7F:
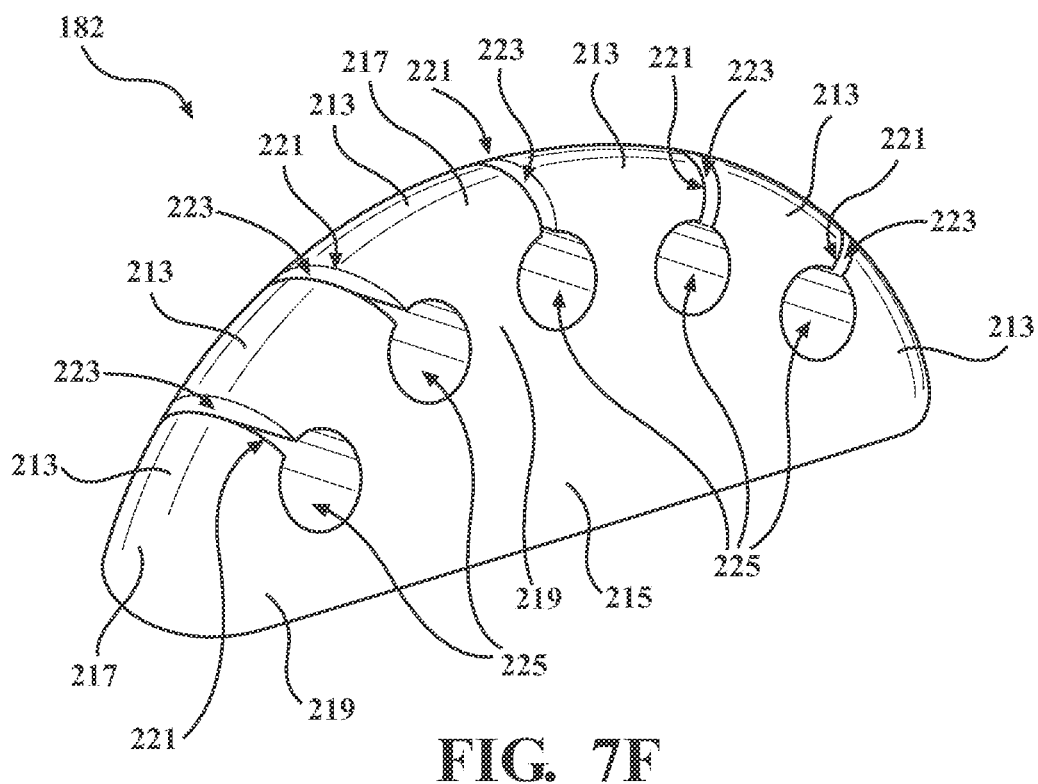
FIG. 7F is a perspective view of a line coupler of the line coupler assembly of FIG. 7A, according to one embodiment.

As shown in FIG. 7F, the first embodiment of the line coupler 182 comprises digits 213 extending away from a base portion 215. Each digit has an upper end 217 and a lower end 219. The upper end 217 of each digit is wider than the lower end 219 of the same digit. Thus, the space between adjacent digits 213 at the lower end 219 of the digits 213 form grooves 221 comprising a narrow portion 223 and a wide portion 225. The line coupler 182 is configured such that medical lines may be disposed within the wide portion 225 of the grooves 221, as shown in FIG. 7B, upon the medical lines being traversed through the narrow portion 223 of the grooves 221 by the caregiver. It will be appreciated that the widths of the grooves 221 may be configured appropriately for each type of medical line 163 (i.e., the grooves 221 may not have the same widths in the same line coupler 182).

Figure 7G:
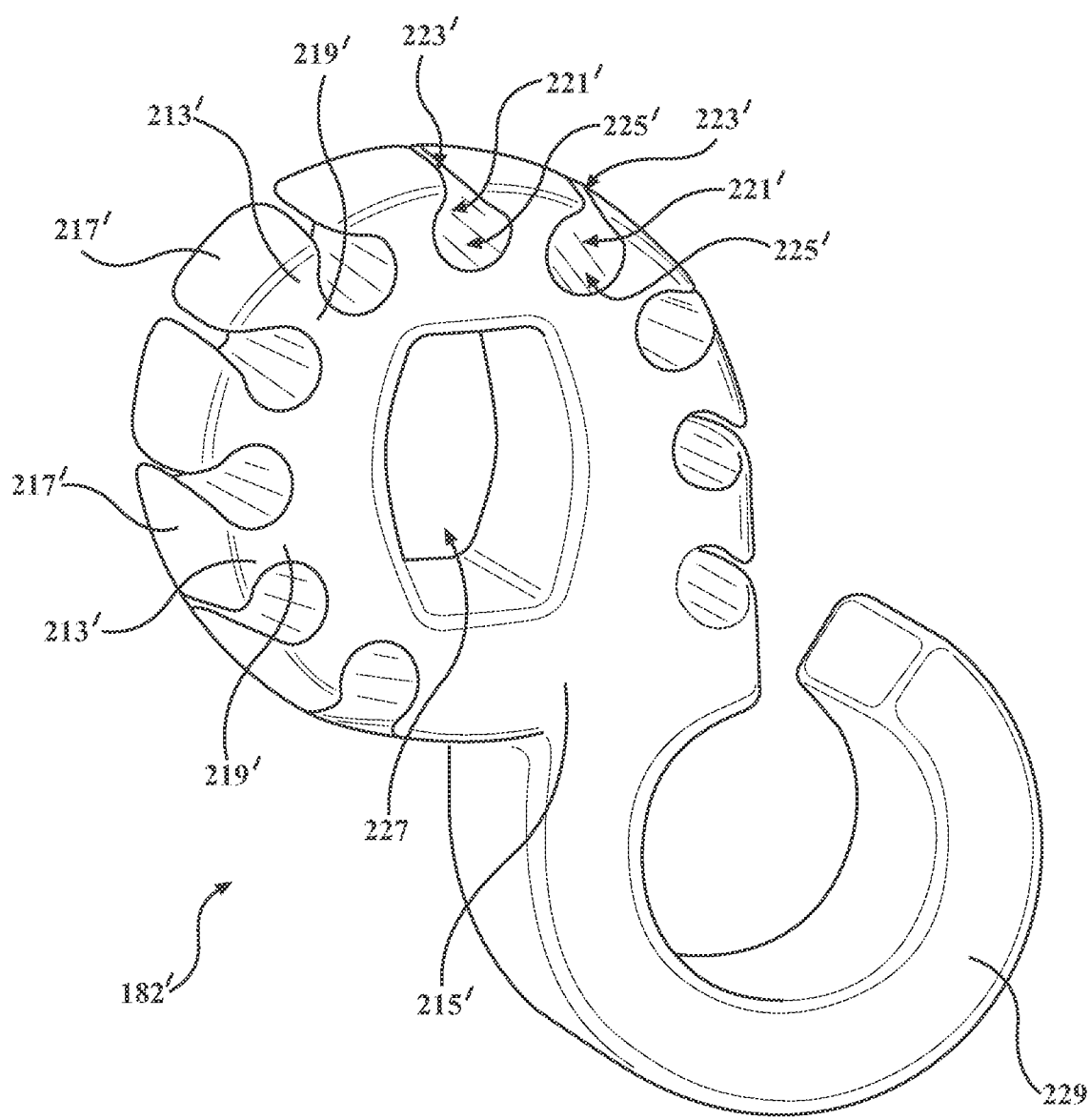
FIG. 7G is a perspective view of another embodiment of a line coupler configured to mount on the line coupler assembly of FIG. 7A.

With reference to FIG. 7G, an alternative embodiment of line coupler 182' is shown. The liner coupler 182' comprises a base portion 215' that defines an arm section void 227 configured to engage the fourth arm section 178 of the line coupler assembly 162 such that the line coupler 182' can slide along the fourth arm section 178. Further, it is contemplated that the line coupler 182' may be coupled to other arm sections instead, such as, the second arm section 170. The line coupler 182' further comprises a hook portion 229 extending from the base portion 215'. The hook portion 229 is configured and dimensioned such that ventilation tubes can be disposed within, supported, and or retained by the hook portion 229.

The line coupler 182' further comprises digits 213' extending away from a base portion 215'. Each digit has an upper end 217' and a lower end 219'. The upper end 217' of each digit is wider than the lower end 219' of the same digit. Thus, the space between adjacent digits 213' at the lower end 219' of the digits 213' form grooves 221' comprising a narrow portion 223' and a wide portion 225'. The line coupler 182' is configured such that medical lines 163 may be disposed within the wide portion 225' of the grooves 221', as shown in FIG. 7B, upon the medical lines being traversed through the narrow portion 223' of the grooves 221' by a user, such as the caregiver. It will be appreciated that the widths of the grooves 221' may be configured appropriately for each type of medical line 163' (i.e., the grooves 221' may not have the same widths).

Referring now to FIGS. 7B, 8A-8C, and FIGS. 9A and 9B, the mounting devices 184 are configured to mount or couple the medical accessory to the accessory support, such as post. By way of non-limiting example, the mounting device 184 may comprise cam clamp 214 (FIGS. 8A-8C), a cleat lock 216 (FIGS. 9A and 9B), or the screw clamp 173 (FIG. 7B). It is to be appreciated that these mounting devices 184 may be fixed to, or integral with, the first component or the second component to allow the first component or the second component to be mounted to/supported by various accessory supports, such as IV poles.

Figure 8A:
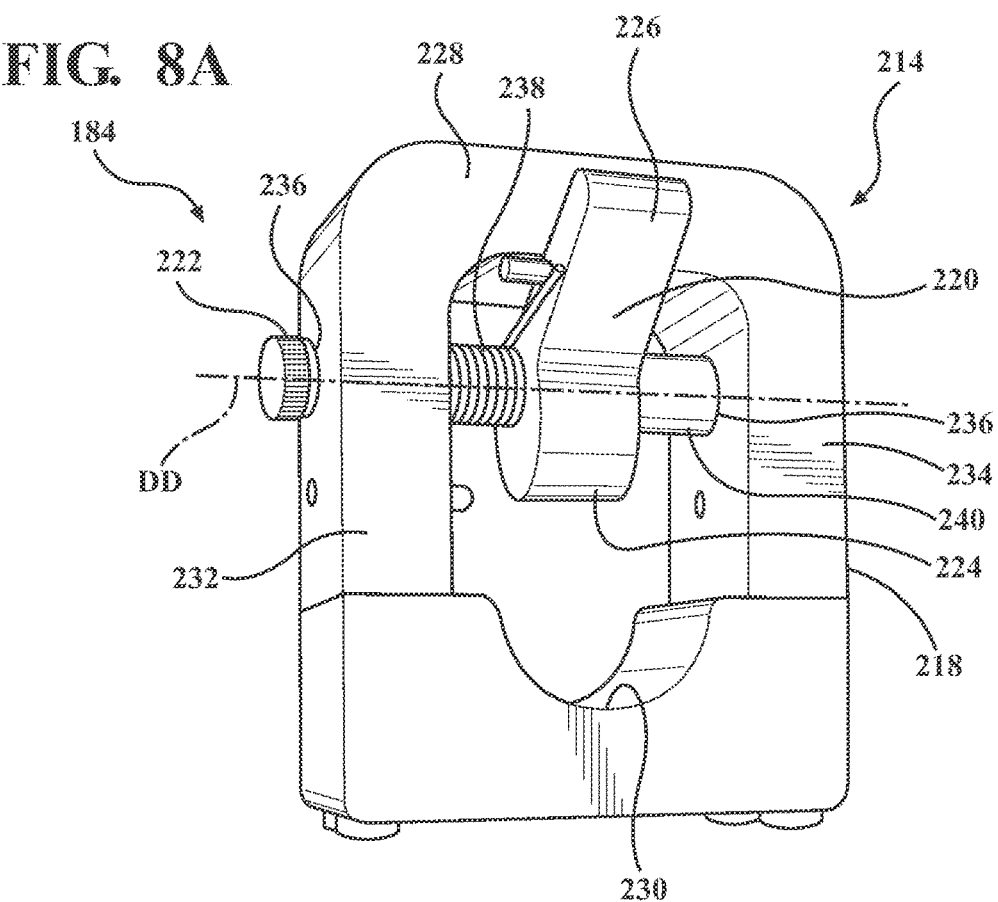
FIG. 8A is a perspective view of one embodiment of a cam clamp.
Figure 8B:
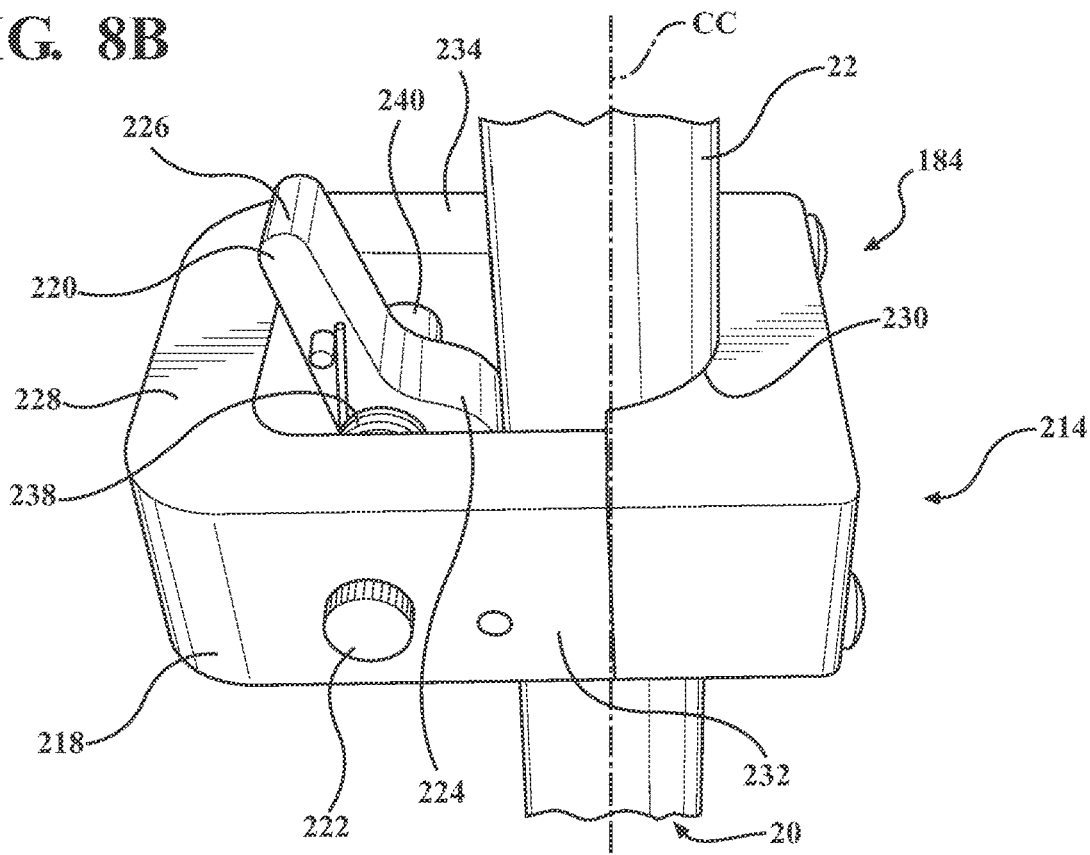
FIG. 8B is a perspective view of the cam clamp of FIG. 8A shown engaging and secured to a portion the accessory support of FIG. 1.

Certain mounting devices 184 may be configured to assume a secured state and an unsecured state. When in the unsecured state, the mounting devices 184 can move freely in the vertical direction relative to a longitudinal axis CC of the post 22, as shown in FIG. 8C. On the other hand, when in the secured state, the mounting devices 184 cannot move freely in the vertical direction, at least not downwardly in the vertical direction, relative to the longitudinal axis CC of the post 22 as shown in FIG. 8B.

In some instances the mounting device 184, such as cam clamp 214, is configured to rotate freely about the longitudinal axis CC of the post 22 in both the secured and unsecured states. Of course, it is also contemplated that rotation of the cam clamp 214 about the longitudinal axis CC of the post 22 may be restricted when the cam clamp 214 is in the secured configuration. In some instances cam clamp 214 may be fixed relative to the post 22 when the cam clamp 214 is in the secured state.

In certain embodiments, the mounting device 184, such as cam clamp 214, is further configured such that the medical accessory coupled thereto can rotate about the longitudinal axis CC of the post 22, while retaining its height relative to the post 22. In other words, the cam clamp 214 may be capable of supporting the weight of the medical accessory on the post 22 and prevent downward movement, while still allowing the medical accessory to rotate about the longitudinal axis CC of the post 22.

In addition, the mounting device 184, such as cam clamp 214, may be configured to be biased into the secured state. In other words as illustrated, upon engagement of the cam clamp 214 with the post 22, the cam clamp 214 automatically engages the post 22 without requiring caregiver actuation.

By way of example, in one embodiment, the mounting device 184 comprises the cam clamp 214. As shown in FIGS. 8A and 8B, the cam clamp 214 comprises a clamp frame 218, a cam member 220, and a cam pin 222. The cam member 220 further comprises an engagement portion 224 and a lever 226. In the illustrated embodiment the clamp frame 218 comprises a U-shaped portion 228 and a pole groove 230 for accommodating the cylindrical shape of the illustrated post 22. The U-shaped portion 228 has a first leg 232 and a second leg 234. As illustrated, the clamp frame 218 comprises two pieces; however, it should be appreciated that the clamp frame 218 may be one-piece.

The first leg 232 and the second leg 234 each define clamp frame apertures 236, and the two ends of the cam pin 222 are disposed in the clamp frame apertures 236. The cam member 220 is rotatably coupled to the cam pin 222 such that the cam member 220 is rotatable about an axis DD defined by the cam pin 222. The cam clamp 214 further comprises a biasing member 238 operably coupled to the cam member 220 to bias the cam member 220 to a secured state where the cam member 220 engages the post 22. The biasing member 238 exerts force on the cam member 220 such that the cam member 220 abuts an alignment member 240 and is aligned in a pre-determined position that is substantially aligned, or aligned, with the pole groove 230 of the clamp frame 218.

In the secured state and as described generally above, the cam member 220 engages the post 22 such that the cam clamp 214 cannot move freely in the downward vertical direction relative to the longitudinal axis CC of the post 22. In some instances the cam clamp 214 may rotate freely about the longitudinal axis CC of the post 22 when the cam member 220 is in the secured state.

As illustrated, the biasing member 238 comprises a torsion spring 238 disposed about the cam pin 222 with one end of the torsion spring 238 engaging the first leg 232 of the U-shaped portion 228 and the second end of the torsion spring engaging the cam member 220. Other types of biasing members are contemplated, and these biasing members may be arranged in a configuration to ensure that the cam member 220 is biased against the post 22.

The clamp frame 218 of the cam clamp 214 may be configured to be attached to a first component, or a second component, of the coupling system that will be described below. Alternatively, the medical accessory may be coupled directly to the clamp frame 218.

The caregiver may operate the cam clamp 214 by rotating the cam member 220 between the secured state and the unsecured state by engaging the lever 226. As shown in FIG. 8B, when in the secured state the engagement portion 224 abuts the post 22 of the cam member 220 and the pole groove 230 of the clamp frame 218 such that the cam clamp 214 is resistant to vertical movement with respect to the post 22. As shown in FIG. 8C, when in the unsecured state, the post 22 abuts only the pole groove 230 such that the cam clamp 214 is able to move freely with respect to the post 22, both vertically and rotationally about the post 22. When the caregiver does not engage the lever 226, the biasing member 238 applies a force that ensures the engagement portion 224 of the cam member 220 engages the post 22 to prevent vertical movement thereabout. Even when the biasing member 238 applies such force the cam clamp 214 can be rotated about the longitudinal axis CC of the post 22.

Figure 9A:
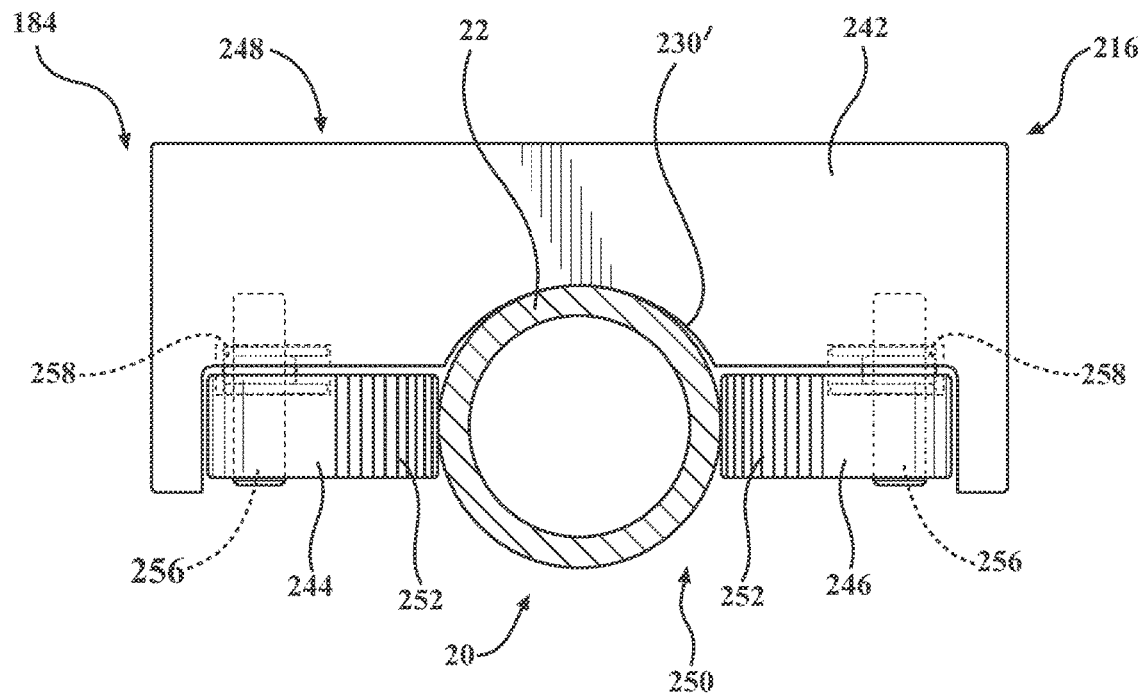
FIG. 9A is a top-side view of one embodiment of a cleat lock shown engaging the accessory support of FIG. 1.
Figure 9B:
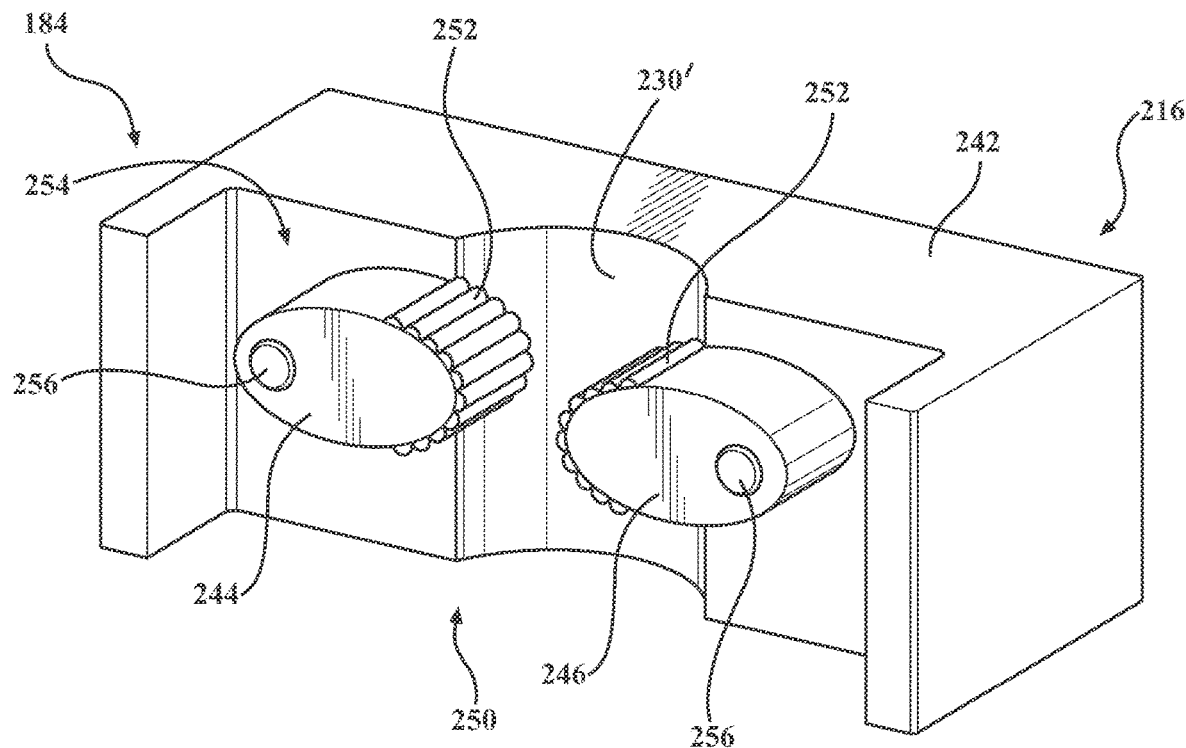
FIG. 9B is a perspective view of the cleat lock of FIG. 9A.

With reference to FIGS. 9A and 9B, in another embodiment the mounting device 184 comprises the cleat lock 216. The cleat lock 216 comprises a cleat lock base 242, a first engaging member 244, and a second engaging member 246. The cleat lock base 242 has a mounting face 248 and an engagement face 250 opposite to the mounting face 248. The mounting face 248 may be coupled to the first component or the second component of the coupling system. Alternatively, the medical accessory may be coupled directly to the mounting face.

Referring to FIG. 9A, the first and second engaging members 244, 246 of the cleat lock 216 each have a grip portion 252 for engaging with the accessory support 20, such as post 22. In some instances, such as in the illustrated embodiment, the grip portion 252 of the first and second engaging members 244, 246 comprises a rib portion 252 to facilitate engagement the first and second engaging members 244, 246 with the post 22.

Referring to FIG. 9B, in the illustrated embodiment, the engagement face 250 further comprises a channel 254. The channel 254 comprises a pole groove 230' for receiving the post 22. The first and second engaging members 244, 246 are movably disposed within the channel 254. In the illustrated embodiment, the first and second engaging members 234, 236 are rotatably coupled to the cleat lock base 242 by coupling pins 256.

A biasing apparatus 258 shown schematically in FIG. 9A urges each of the first and second engaging members 244, 246 into a secured state. As shown in FIG. 9B, in the secured state the biasing apparatus 258 biases the grip portions 252 of the first engaging member 244 towards the grip portion 252 of the second engaging member 246. In the illustrated embodiment, the grip portions 252 of the first and second engaging members 244, 246 are spaced from one another even when no post 22 is positioned there between. However, in other embodiments it is contemplated that the grip portions 252 of the first and second engaging members 244, 246 may abut each other when no post 22 is positioned there between.

In the secured state, the first and second engaging members 244, 246 engage the post 22 when the post 22 abuts the pole groove 230' of the cleat lock base 242. In the secured state the cleat lock 216 and, by association, the medical device, cannot move in the downward direction relative to the post 22. Moreover, the first and second engaging members 244, 246 exert a force, in the upward direction on the post 22 that is equal to or greater than the force exerted on the cleat lock 216, and the accompanying medical accessory attached thereto, by gravity.

To operate the cleat lock 216, the caregiver positions the post 22 such that it abuts the outward surfaces of the first and second engaging members 244, 246. By pressing the cleat lock 216 against the post 22 and simultaneously lowering the cleat lock 216 such that as the post 22 abuts the outward surface of the first and second engaging members 244, 246 the grip portions 252 rotate about the coupling pin 256 towards the bottom of the cleat lock 216.

As the first and second engaging members 244, 246 move away from the post 22, the post 22 can be brought into abutment with the pole groove 230' of the engagement face 250 of the cleat lock 216. When the post 22 abuts the pole groove 230', and the first and second engaging members 244, 246 are not substantially inhibited by the post 22, the first and second engaging members 244, 246 are biased towards the top of the post 22 to prevent movement of the cleat lock 216 downward along the post 22 in the vertical direction.

The caregiver may remove the post 22 from the cleat lock 216 by vertically raising the cleat lock 216 with respect to the post 22 such that the first and second engaging members 244, 246 rotate towards the bottom of the cleat lock base 242 as they no longer inhibit the post 22. In this manner a caregiver can quickly couple and de-couple the cleat lock 216, and attached medical accessories, to and from the post 22.

The present disclosure also provides a coupling system for coupling a medical accessory to an accessory support.

The coupling system comprises the first component and second component described above. The first component is configured to mechanically couple the second component in a manner sufficient for the first component to support the weight of the second component (and the medical accessory or accessory support coupled thereto), or vice-versa. While the phrases 'first component' and 'second component' are used throughout this disclosure and claims to refer to specific structural and functional configurations, the phrases are used interchangeably. In other words, any first component may be configured identically to configurations described with reference to the second component, and vice-versa.

The first component may be mounted to, or integral with, one of the accessory support or the medical accessory. The second component may be mounted to, or integral with, the other of the accessory support and the medical accessory. In some embodiments, the first and second components may be mounted on each of the accessory support via any of the mounting devices described above It is further contemplated that the first or second component may be mounted to any location on any accessory supports, patient support apparatuses, or patient transport chairs described herein. Further, the first or second components may be mounted to any location of any other tables, chairs, beds, and boom stands found within a healthcare facility.

With reference to FIG. 1, a coupling system 212 according to one embodiment is provided. The coupling system 212 permits the quick and efficient support of medical accessories by accessory supports 20, such as post 22, or the mounting apparatus 124 (see FIG. 5A). Generally, the coupling system 212 comprises the first component 160 and the second component 210. The first component 160 is configured to couple to the second component 210 in a manner sufficient for the first component 160 to support the weight of the second component 210, or vice-versa. It should be appreciated that various orientations of the first and second components are contemplated beyond what is illustrated explicitly in the figures. For example, the first and second components may be turned upside down or sideways and still preserve their functionality.

The intersection of the first component and the second component described throughout this disclosure may result in the power, data, fluid, and mechanical interfaces described herein.

In the illustrated embodiment, the second component 210 may couple the first component 160 by approaching the first component from above. However, in some embodiments, the first component may comprise a hanger. When the first component comprises the hanger, the second component may approach the first component from below and hang from the first component 160.

While several exemplary embodiments are shown (see FIGS. 10-12), the design of the first component and the second component is not particularly limited. With reference to FIGS. 10A-B and 11A-D, in one embodiment, the coupling system is configured such that the first component 160 is configured to interact with the second component 210 in a locked arrangement and an unlocked arrangement. More particularly, the first component 160 is configured to support the second component 210 in both the locked arrangement and the unlocked arrangement. The coupling system 212 may be further configured such that the first component 160 prevents downward movement, i.e., falling, of the second component 210 when the second component 210 is supported by the first component 160 and the first and second components 160, 210 are in the unlocked arrangement. It is also contemplated that the first component 160 may prevent lateral movement of the second component 210 relative to the first component 160 when the first and second components 160, 210 are in the locked arrangement.

Figure 10A:
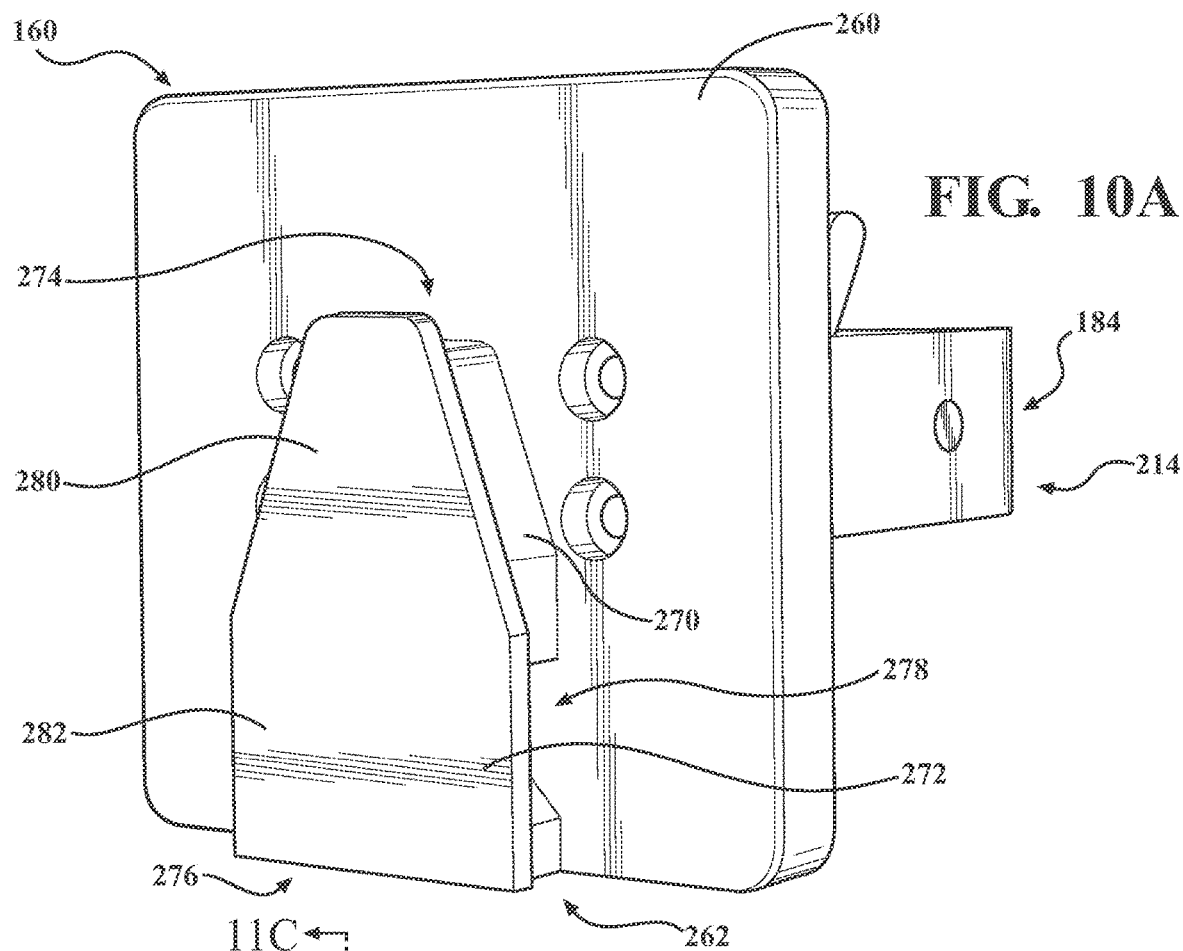
FIG. 10A is a perspective view of a first component according to a first embodiment of a coupling system, the first component including a mounting portion comprising the cam clamp of FIG. 8A.
Figure 10B:
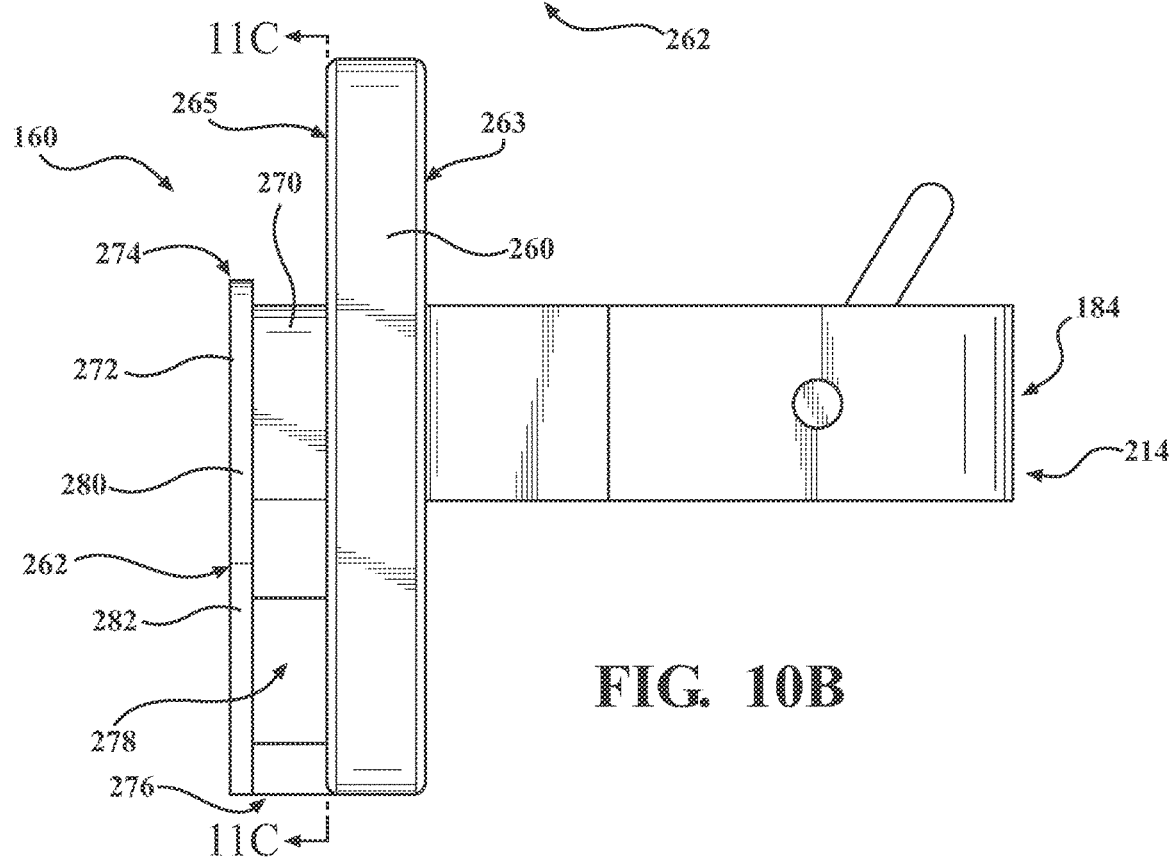
FIG. 10B is a side view of the first component of FIG. 10A and the cam clamp of FIG. 8A.

With reference to FIG. 10A and FIG. 10B, in a first embodiment the first component 160 comprises a first mounting portion 263 and a first coupling portion 265.

In the illustrated embodiment, first component 160 comprises a first base 260 and a projection 262 extending from the first base 260. The first base 260 may be configured such that the first mounting portion 263 of the first component 160 may be mounted to the mounting devices 184, such as cam clamp 214, as described above and shown in FIG. 10A depending on the type of accessory support. Alternatively, the first mounting portion 263 may be directly mounted to the mounting apparatus 124, as shown in FIG. 6B.

The projection 262 comprises a pillar 270, and a lip 272 disposed on the pillar 270. The pillar 270 extends outwardly from the first base 260. The pillar 270 comprises a top 274 and a bottom 276. Between the top 274 and the bottom 276, the pillar 270 comprises a recess 278 on each side. The recess 278 is configured to engage at least a portion of the second component 210. The lip 272 comprises an angled portion 280 and a rectangular portion 282. Because each portion of the lip 272 is generally wider than the adjacent portion of the pillar 270, the lip 272 extends transverse beyond the pillar 270.

Figure 11A:
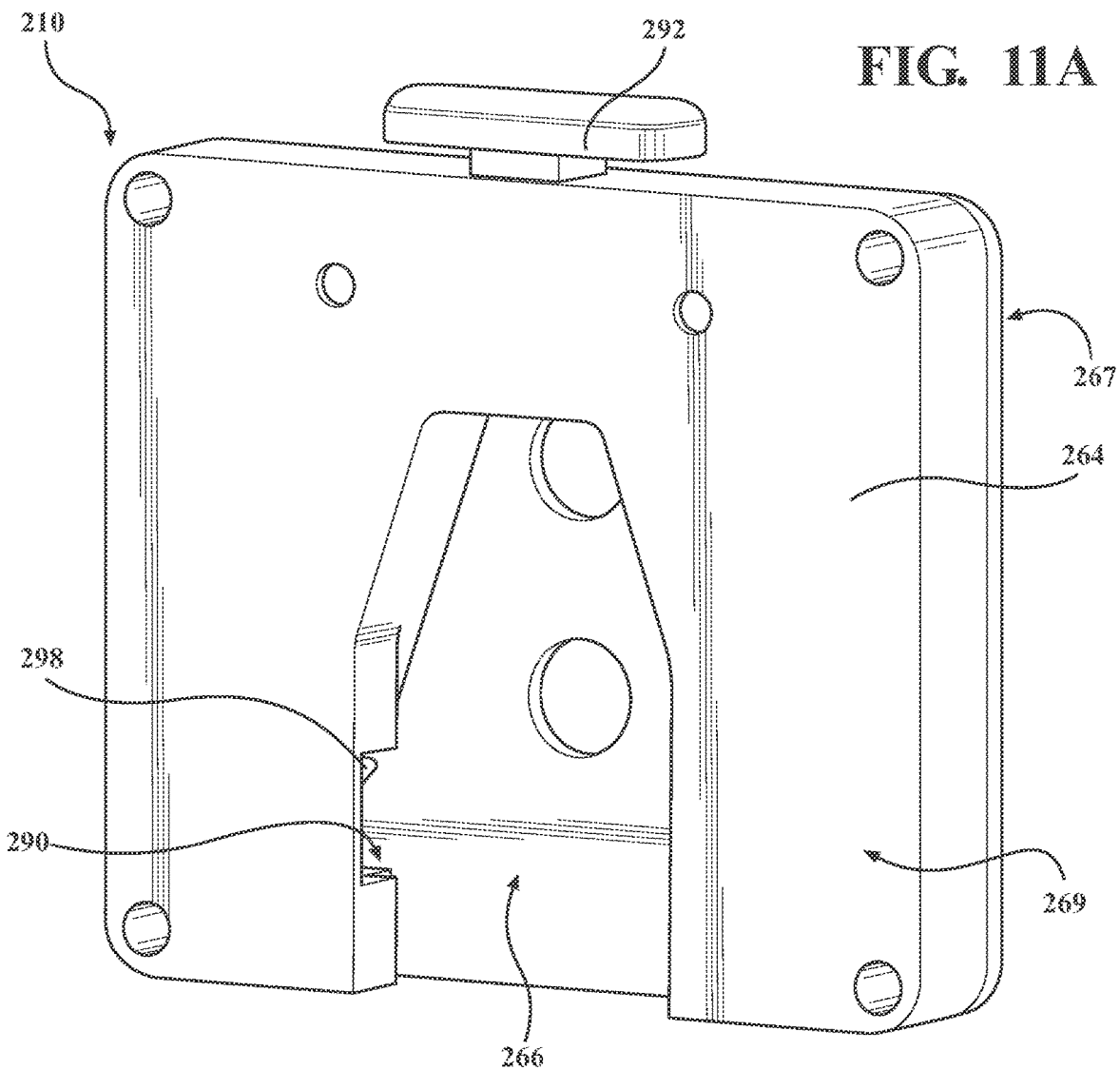
FIG. 11A is a perspective view of a second component according to the first embodiment of the coupling system for coupling to the first component of FIGS. 10A and 10B.
Figure 11B:
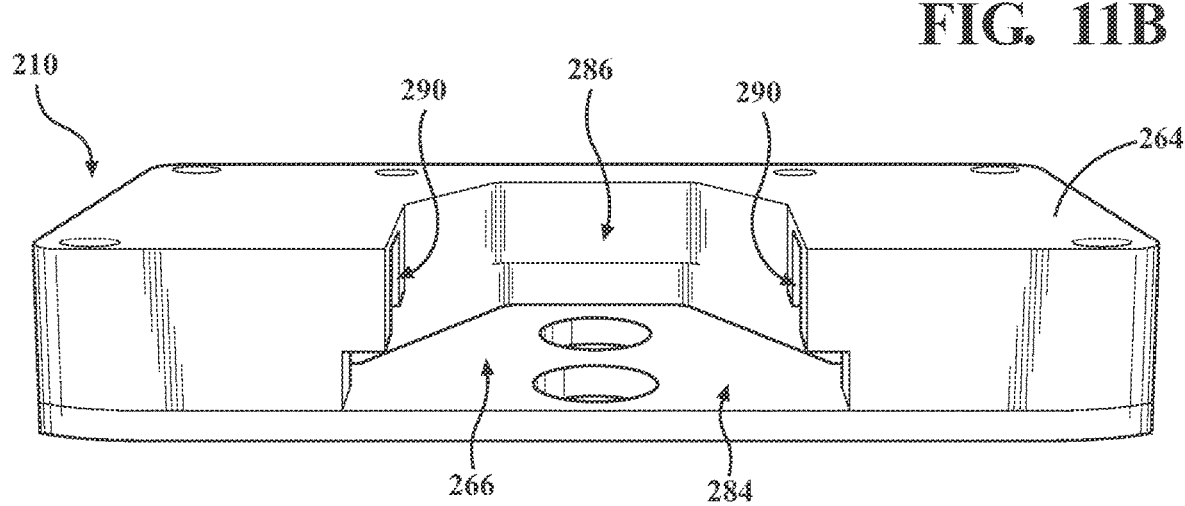
FIG. 11B is a rotated perspective view of the bottom of the second component of FIG. 11A.

Referring now to FIGS. 11A and 11B in the illustrated embodiment, the second component 210 comprises a second mounting portion 267 and a second coupling portion 269. The second mounting portion 267 may be mounted to a medical accessory. The second component 210 further comprises a second base 264. The second base 264 comprises a slot 266 configured to accept the projection 262 of the first component 160 to releasably couple the first component 160 to the second component 210.

Figure 11C:
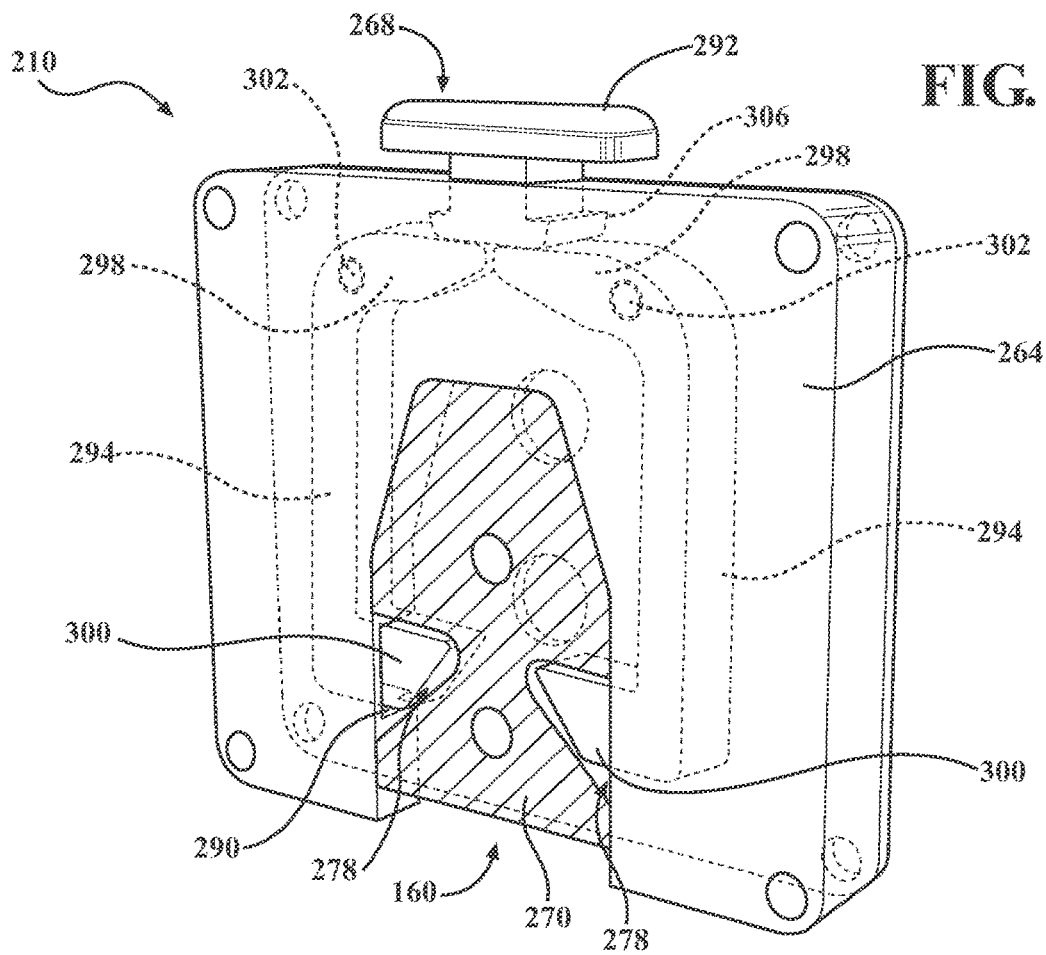
FIG. 11C is a partial perspective view of the second component of FIG. 11A with a locking assembly engaging the first component of FIG. 10A, depicted in section as taken along line 11C-11C of FIG. 10B, in a locked arrangement.

As shown in FIG. 11C, the second component 210 comprises a locking assembly 268 disposed within the second base 264 and configured to selectively engage the projection 262 of the first component 160 to restrict movement of the first component 160 with respect to the second component 210 when the locking assembly 268 is engaged. While one exemplary embodiment of the locking assembly 268 is shown in FIG. 11C, alternative configurations of the locking assembly are contemplated.

Referring now to FIG. 1, when the locking assembly 268 is present, at least one of the first and second components 160, 210 may further comprise an indicator device 380 configured to provide a coupling status of the coupling system 212 to the caregiver. The coupling status may comprise a locked status when the first and second components 160, 210 are in the locked arrangement and an unlocked status when the first and second components 160, 210 are in the unlocked arrangement. Thus, the indicator device 380 may alert a user when the first and second components 160, 210 are in the locked arrangement or the unlocked arrangement. The indicator device 380 may comprise, by way of non-limiting example, a visual indicator, an audible indicator, a tactile indicator, or any indicator configured to alert a user to a status of the coupling system 212. The indicator device 380 may be electrical, mechanical, or electromechanical in nature.

With reference to FIG. 11B as described above, the slot 266 of the second component 210 is shaped to receive the projection 262 of the first component 160. The slot 266 comprises a lip-receiving portion 284 that is shaped to receive the lip 272 of the first component 160 and a pillar-receiving portion 286 that is shaped to receive the pillar 270 of the first component 160. Thus, as illustrated, the lip-receiving portion 284 of the slot 266 comprises a straight portion and an angled portion. Similarly, the pillar-receiving portion 286 of the slot 266 comprises a rectangular portion and an angled portion. The second component 210 may further comprise locking assembly cavities 290.

With reference to FIG. 11C, the locking assembly 268 is disposed within the second base 264 of the second component 210. In the illustrated embodiment, the locking assembly 268 comprises a second user input device 292 partially disposed within the second base 264. The second user input device 292, shown as a button 292 in accordance with one embodiment, may be slidably displaceable relative to the second base 264 between an initial position and a depressed position. Still other second user input devices 292 are also contemplated, including but not limited to, electronic switches, voice actuation device, etc.

As illustrated, the locking assembly 268 in one embodiment, further comprises first and second locking arms 294. The first and second locking arms 294 each have shoulder portions 298 and finger portions 300. The first and second locking arms 294 are configured to rotate about arm pins 302. The button 292 comprises a lock engaging portion 306 disposed substantially within, or within, the second base 264 and configured to engage the shoulder portions 298 of the first and second locking arms 294. A biasing assembly (not shown) urges the first and second locking arms 294 into a locked arrangement, as shown in FIG. 11C. When in the locked arrangement, the finger portions 300 of the first and second locking arms 294 extend through the locking assembly cavities 290 of the second component 210 to engage the recess 278 of the first component 160. Moreover, when the locking assembly 268 is in the locked arrangement, the button 292 is in the initial position and the lock engaging portion 306 does not engage the shoulder portions 298 of the first and second locking arms 294. Other locking assembly configurations are also contemplated.

Figure 11D:
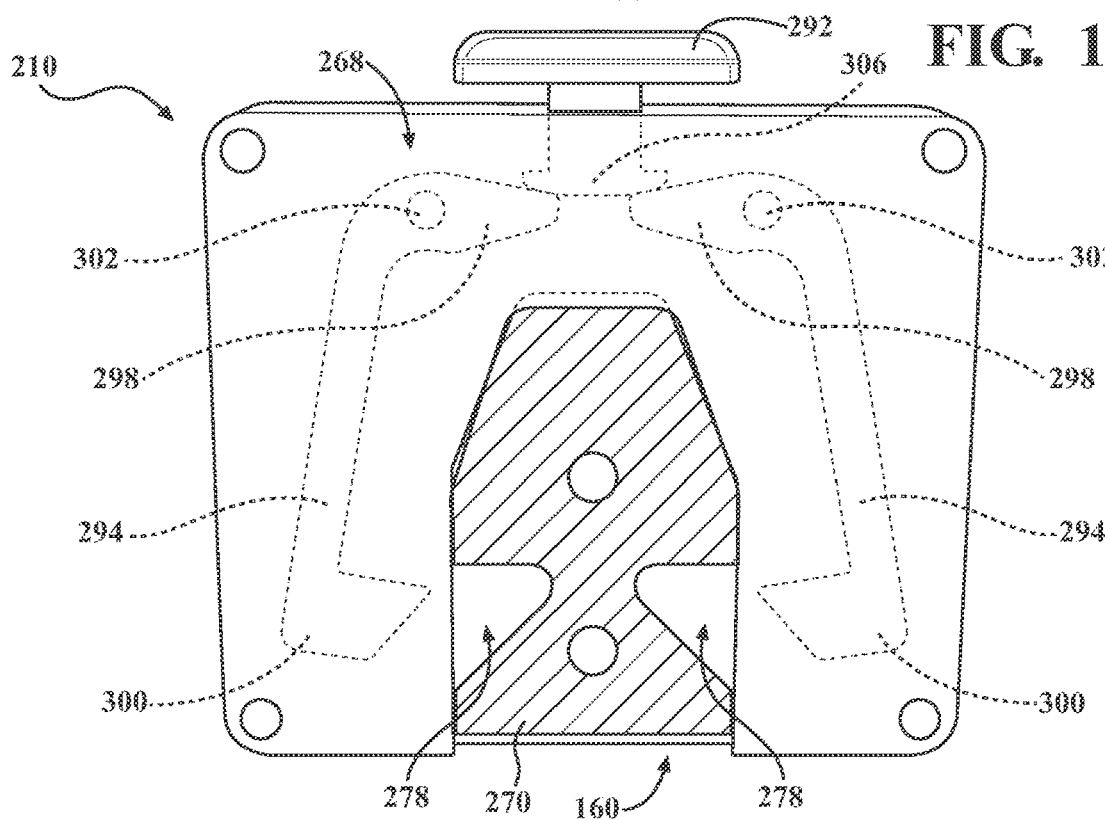
FIG. 11D is partial perspective view of the second component of FIG. 11A shown engaging the first component of FIG. 10A, depicted in section as taken along line 11C-11C of FIG. 10B, in an unlocked arrangement.

The first component 160 and the second component 210 may be coupled together, as shown in FIGS. 11C and 11D. When coupled, the lip of the first component 160 engages the lip-receiving portion of the second component 210, and the pillar 270 of the first component 160 engages the pillar-receiving portion of the second component 210. Referring to FIG. 11C, the locking assembly 268 is shown in the locked arrangement. When the first component 160 and the second component 210 are coupled and the locking assembly 268 is in the locked arrangement, the first component 160 and the second component 210 cannot move relative to each other. Engagement of the locking assembly 268 prevents movement of the first component 160 and second component 210 relative to one another.

Referring now to FIG. 11D, with the locking assembly 268 in an unlocked arrangement, a user may couple the first component 160 and the second component 210 by first engaging the top of the projection 262 with the slot 266 of the second component 210. When coupled to an accessory support 20, either directly or via a mounting device 184 as described above, the first component 160 may support the weight of the second component 210 and a medical accessory coupled to the second component 210 while the locking assembly 268 is in the unlocked arrangement (i.e., the locking assembly 268 does not need to be in the locked arrangement for the weight of the medical accessory 26 coupled to the second component 210 to be operably supported by the first component 160). In other words, even if the locking assembly 268 was absent, the interaction of the pillar 270 and the pillar-receiving portion 286 and the interaction of the lip 272 and the lip-receiving portion 284 prevent relative movement between the first component 160 and second component 210 in all but the upward direction. This ensures that the first component 160 and second component 210 can only disengage from one another if the first component 160 is raised upward relative to the second component 210. Once the first component 160 and the second component 210 are fully engaged, and the locking assembly apertures 290 become open to the recess 278 of the projection 262 of the first component 160, the first and second locking arms 294 move inwards to the locked arrangement, where the finger portions 300 engage the recess 278, as shown in FIG. 11C.

When the first component 160 and the second component 210 are coupled together and the locking assembly 268 is in the locked arrangement, the coupling system permits quick and efficient decoupling. By depressing the button 292, the first and second locking arms 294 move from the locked arrangement to the unlocked arrangement. More particularly, depressing the button 292 causes the lock engaging portion 306 to engage the shoulder portions 298 of the first and second locking arms 294, thereby pivoting the first and second locking arms about arm pins 302 from the locked arrangement to the unlocked arrangement. When the locking assembly 268 is in the unlocked arrangement, the caregiver can lift the second component 210 away from the first component 160, either directly or indirectly via a medical accessory 26 coupled to the second component 210, to cause decoupling.

It is further contemplated that when the locking assembly 268 is present, the locking assembly 268 is biased toward the locked arrangement. Specifically, the locking assembly 268 may not require actuation of the second user input device 292 for the coupling system to be placed in the locked arrangement, but may only require actuation of the second user input device 292 to switch the locking assembly from the locked arrangement to the unlocked arrangement.

Figure 12A:
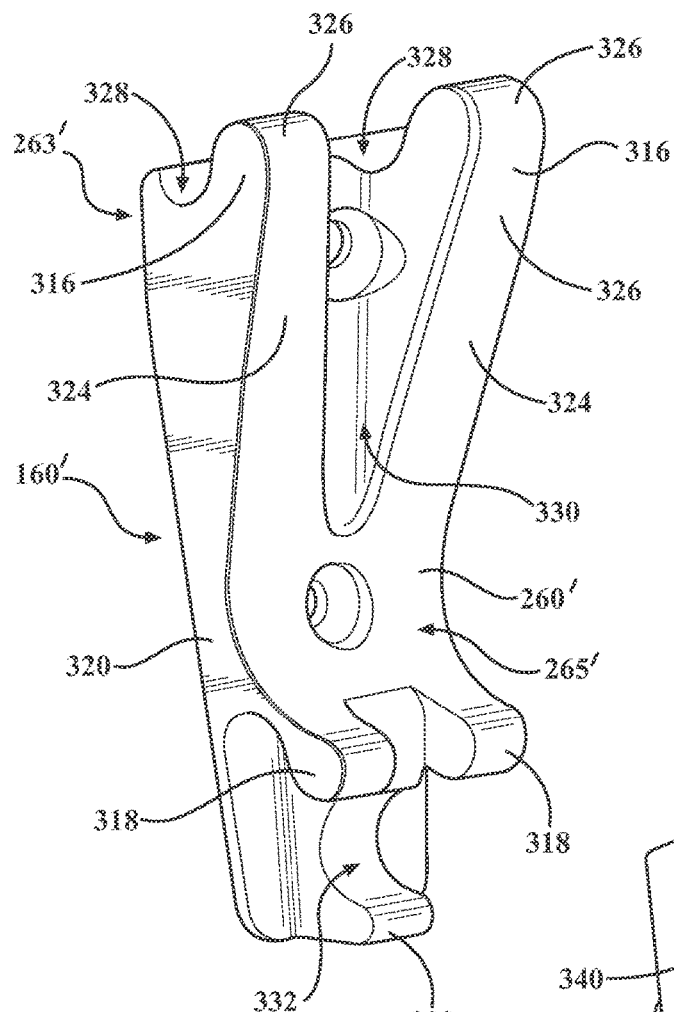
FIG. 12A is a perspective view of a first component in accordance with a second embodiment of a coupling system.

In an alternative embodiment, referring to FIGS. 12A-12E a coupling system 212' comprises a first component 160', and a second component 210'. As shown in FIG. 12A the first component 160' comprises a first base 260'. The first base 260' comprises a first coupling portion 265' and a first mounting portion 263' opposite the first coupling portion 265'. The first mounting portion 263' may be coupled to the mounting devices or the mounting apparatus, as described above. The first base 260' comprises upper guide tabs 316 at the top of the first base 260', intermediate guide tabs 318 at the intermediate portion 320 of the first base 260', and a lower guide tab 322 at the bottom of the first base 260'.

The upper guide tabs 316 comprises a sloped portion 324, a nose 326, and a tab recess 328. As depicted, the upper guide tabs 316 are spaced laterally from one another to define an additional coupling feature 330. The upper guide tabs 316 are angled upward to define the tab recess 328 that rotatably supports the second component 210'. As illustrated, the upper guide tabs 316 comprise a rounded shape to allow easy rotational movement of the second component 210' relative to the upper guide tabs 316.

The intermediate guide tabs 318 are spaced apart from another, and as illustrated, comprise a teardrop shape. The intermediate guide tabs 318 extend downward away from the upper guide tabs 316. The lower guide tab 322 extends outwardly from the first base 260'. The intermediate guide tabs 318 and the lower guide tab 322 cooperate to define a trough 332 that enables locking of the first component 160' relative to the second component 210'.

Figure 12B:
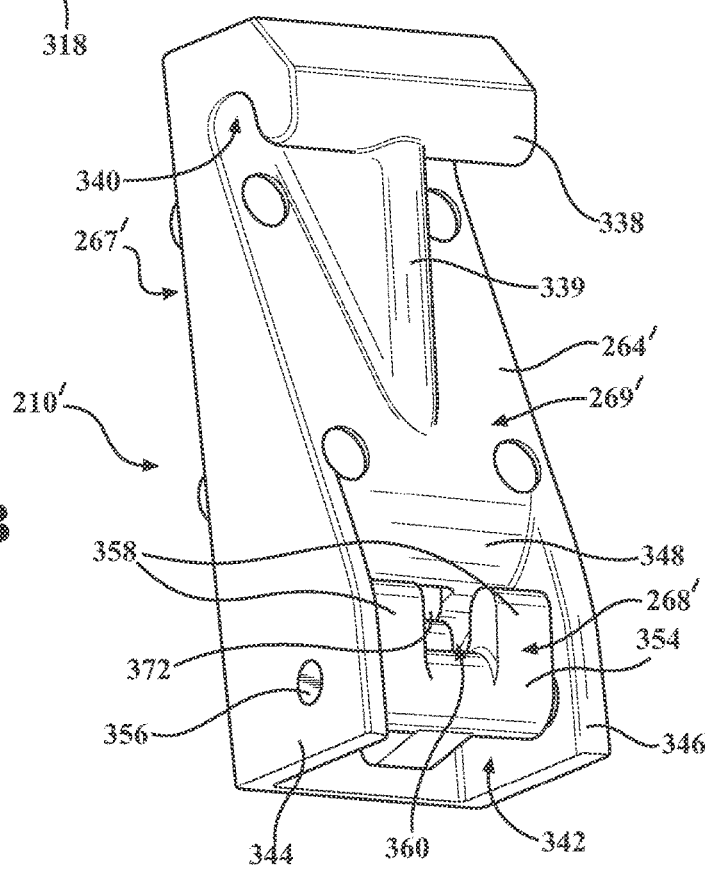
FIG. 12B is a perspective view of a second component for coupling to the first component of FIG. 12A and a locking assembly in accordance with the second embodiment of the coupling system.

With reference to FIG. 12B, the second component 210' comprises a second base 264' having a second mounting portion 267' and a second coupling portion 269' that is opposite the second mounting portion 267'. The second mounting portion 267' may be mounted to a medical accessory.

As shown in FIG. 12B, the second base 264' comprises a hook member 338 extending outward from the second base 264' and shaped to engage the upper guide tabs 316 of the first component 160'. The hook member 338 comprises a hook recess 340. More particularly, the hook member 338 is configured to engage the tab recess 328 of the first component 160' such that the upper guide tabs 316 engage the hook recess 340 of the second component 210'. This engagement allows the weight of the medical accessory, which is coupled to the second component 210' to rest upon the upper guide tabs 316 of the first component 160', whether the first and second components 160',210' are in a locked arrangement or an unlocked arrangement.

The second base 264' further comprises locating feature 339 adjacent the hook member 338 and configured to engage the addition coupling feature 330 of the first component 160, such that the second component 210' cannot move laterally with respect to the first component 160', whether the first and second components 160',210' are in the locked or unlocked arrangement.

Figure 12C:
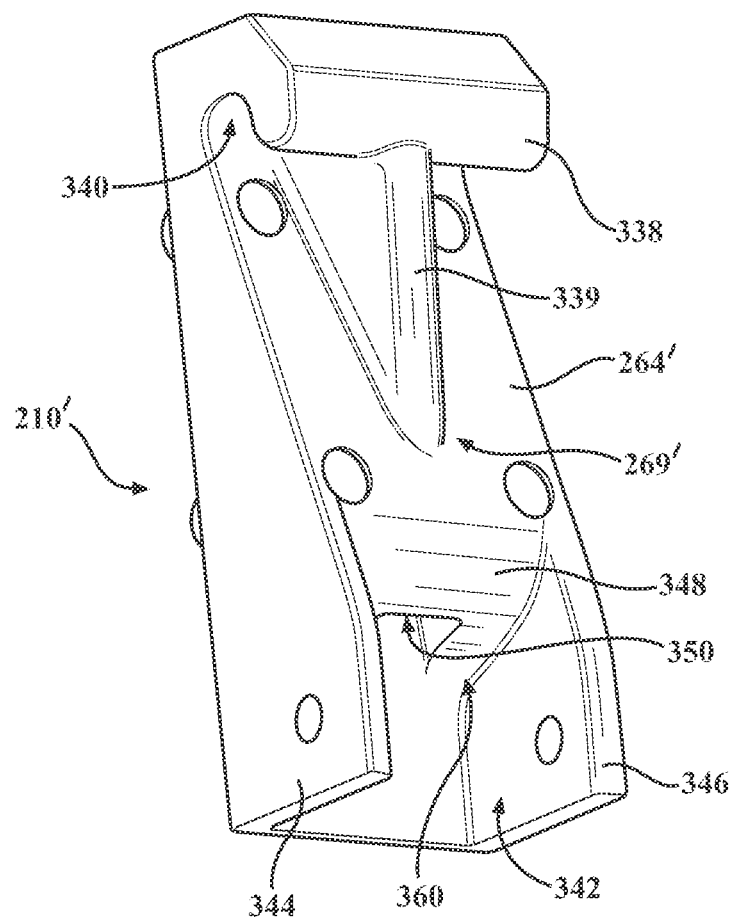
FIG. 12C is a perspective view of the second component of FIG. 12B without the locking assembly.

As shown in FIG. 12C, the second component 210' further comprises a locking chamber 342 at the bottom of the second base 264'. The locking chamber 342 is defined on the two lateral sides by a first wall 344 and a second wall 346. The top of the locking chamber 342 is defined by a ramp 348 that comprises a port 350. The bottom of the locking chamber 342 is open.

With reference to FIG. 12B, the second component 210' further comprises a locking assembly 268' positioned adjacent to the second base 264', at least partially within the locking chamber 342. The locking assembly 268' is configured to releasably secure the first component 160' to the second component 210' when the locking assembly 268' is in the locked arrangement.

Referring to FIGS. 12B and 12D, the exemplary locking assembly 268' comprises a latch 354 at least partially disposed within the locking chamber 342, a detent plunger 372, and a biasing device 374. The latch 354 is pivotable relative to the second component 210' between a locked arrangement and an unlocked arrangement. The latch 354 is rotatably coupled to a latch pin 356. The latch pin 356 is coupled to the first wall 344 and second wall 346 of the female body 314 such that it traverses the locking chamber 342. Thus, the latch 354 rotates about the latch pin 356 between the locked arrangement and the unlocked arrangement.

The latch 354 comprises wings 358 configured to engage the intermediate guide tabs 318. The wings 358 comprise first and second prongs 362, laterally spaced from each other to a define a prong voids 364 such that the first and second prongs 362 engage opposite sides of the intermediate guide tabs 318 of the first component 160', as illustrated in FIG. 12D. With reference to FIG. 12E, the latch 354 further comprises detent member 366 having a tab engaging portion 368 configured to engage the intermediate guide tabs 318 and the lower guide tab 322 of the first component 160', and a cam portion 370 configured to engage the detent plunger 372. The cam portion 370 defines a first nook 376 and a second nook 378 corresponding to the locked arrangement and the unlocked arrangement of the locking assembly 268', respectively.

The detent plunger 372 is at least partially disposed within the port of the second base 264' and is urged by the biasing device 374 in the direction of the latch 354. In the illustrated embodiment, the biasing device 374 is a spring. When in the locked arrangement, the detent plunger 372 engages the first nook 376 of the detent member 366. When in the unlocked arrangement, the detent plunger 372 engages the second nook 378 of the detent member 366.

The first component 160' and the second component 210' may be coupled together, as shown in FIG. 12D. When coupled, the hook member 338 of the second component 210' engages the tab recess 328 of the first component 160', and the intermediate guide tabs 318 and lower guide tab 322 of the first component 160' engage the latch 354 of the locking assembly 268'. Referring to FIG. 12D, the locking assembly 268' is shown in the locked arrangement. When the first component 160' and the second component 210' are coupled and the locking assembly 268' is in the locked arrangement, the first component 160' and the second component 210' cannot move relative to each other. Engagement of the locking assembly 268' prevents movement of the first component 160' and second component 210' relative to one another.

Figure 12F:
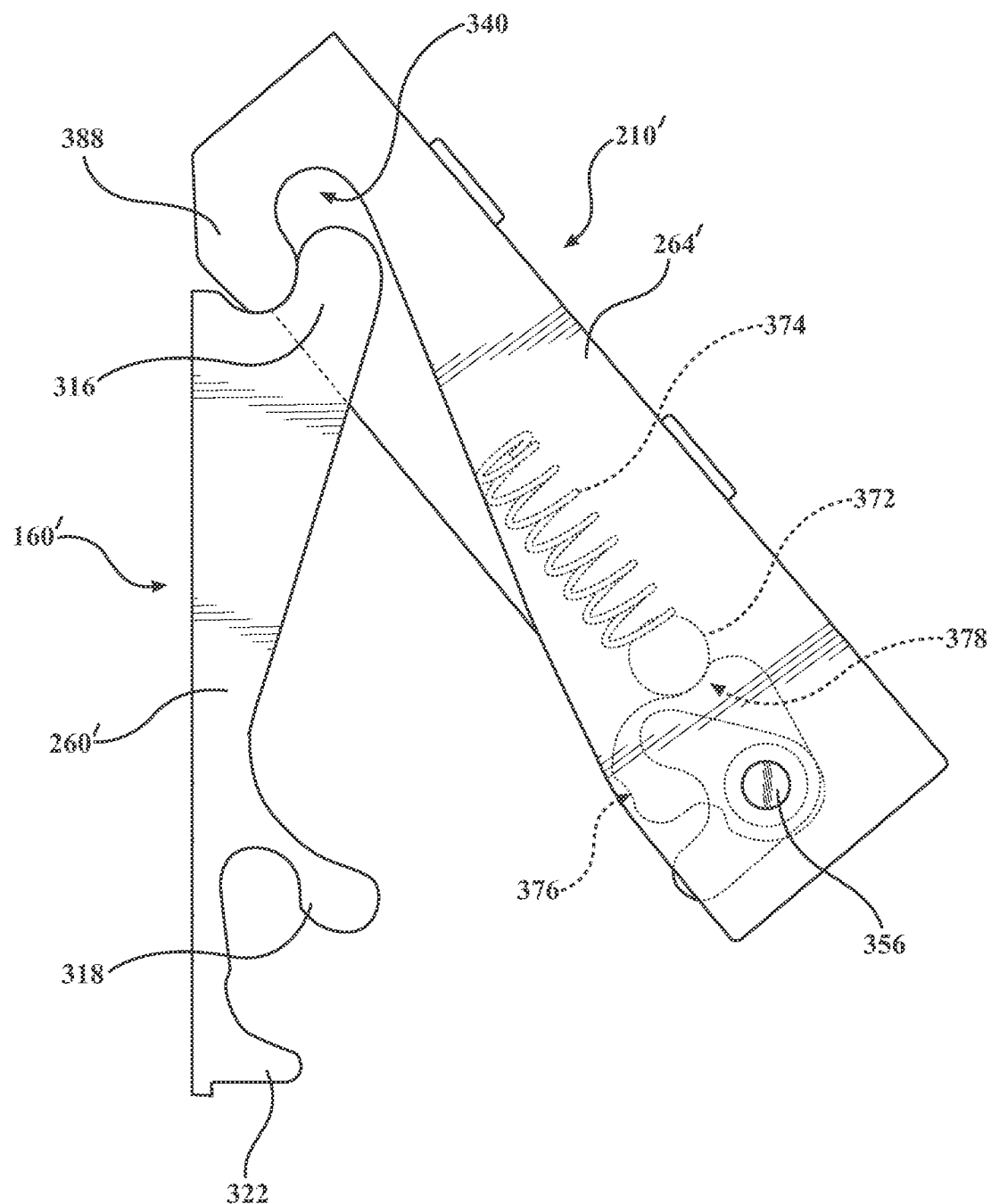
FIG. 12F is a perspective view of the second component of FIG. 12B engaging the first component of FIG. 12A in an unlocked arrangement.

Referring to FIG. 12F, with the locking assembly 268' in the unlocked arrangement, the caregiver may couple the first component 160' and the second component 210' by first engaging the hook member 338 of the second component 210' with the tab recess 328 of the first component 160'. When coupled to an accessory support, either directly or by the mounting devices described above, the first component 160' may support the weight of the second component 210' and a medical accessory coupled to the second component 210' while the locking assembly 268' is in unlocked arrangement (i.e., the locking assembly 268' does not need to in the locked arrangement for the weight of the medical accessory 26 coupled to the second component 210' to be operably supported by the first component 160'). In other words, even if the locking assembly 268' was absent, the hook member 338 of the second component 210' engages the tab recess 328 of the first component 160'. Moreover, the first and second walls 344, 346 engage the intermediate tabs 318 and lower tab 322 such that movement of the second component 210' relative to the first component 160' is prevented in all but the upward direction. The one remaining degree of freedom pertains to raising the second component 210' upward relative to the first component 160'.

Figure 14:
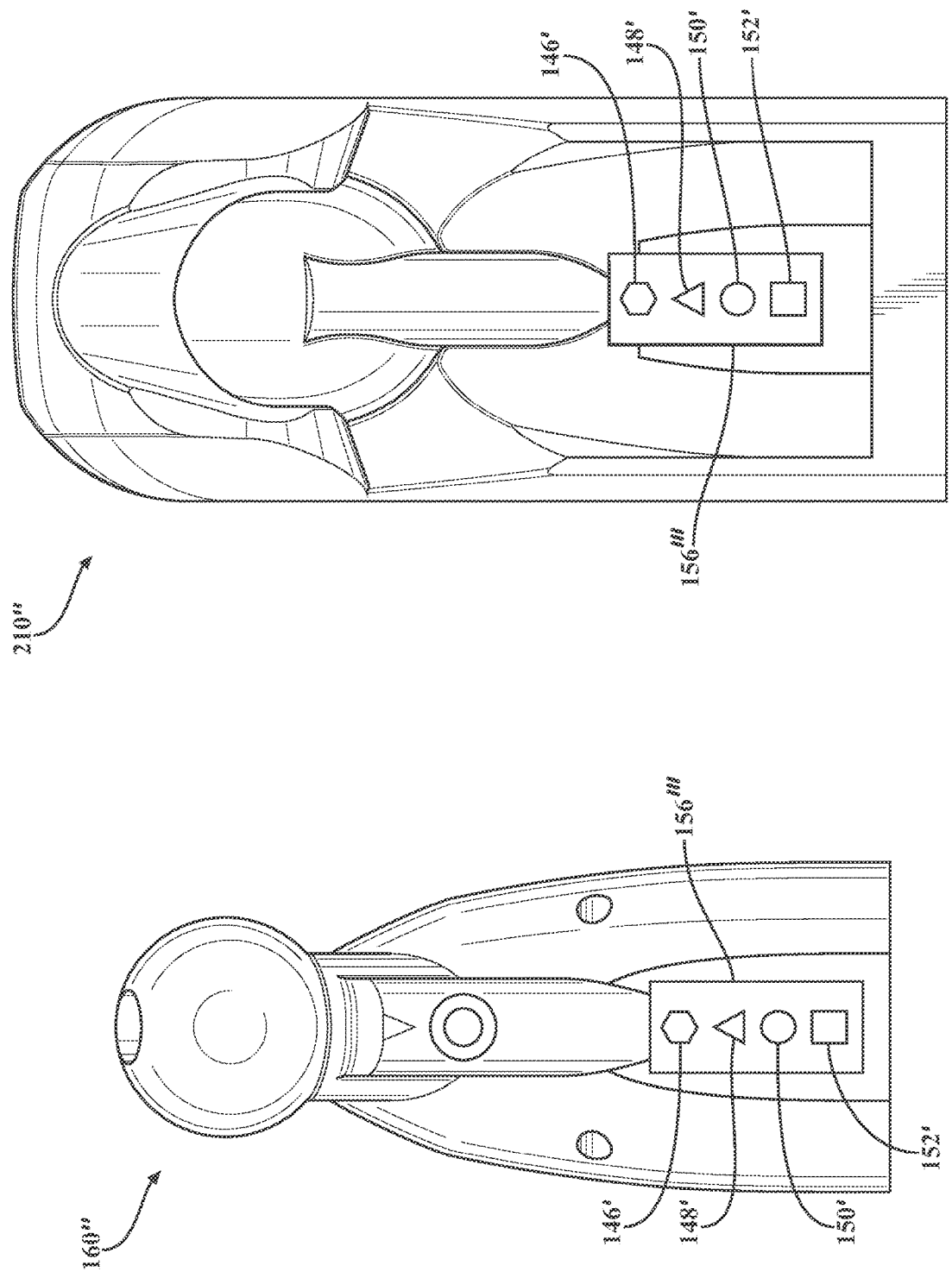
FIG. 14 is a front view of a first and second components of a coupling system according to a third embodiment, depicted schematically with coupling sets.

With reference to FIG. 14, in another embodiment, the coupling system comprises a first component 160", and a second component 210". The first and second components 160", 210" may include a mechanical interface 146', a data interface 148', a power interface 150', and/or a fluid interface 152'. The interfaces 146', 148', 150', 152' may be any type of interface described herein for the mounting apparatus. Thus, the first component 160" and the second component 210" may facilitate the exchange of data between the medical accessory mounted on one of the first and second components 160", 210" and the accessory support mounted on the other of the first and second components 160", 210". Moreover, the first and second components 160", 210" may facilitate supplying power and/or fluid from the accessory support/mounting apparatus to the medical accessory.

In one embodiment, as eluded to above, the first component 160" may be mounted on the accessory support such as the mounting apparatus and the second component 210" may be mounted on the medical accessory. Alternatively, the first component 160" may be mounted on the medical accessory and the second component 210" may be mounted on the mounting apparatus.

The first component 160" may be mechanically, electrically, and/or fluidly coupled to the accessory support. Moreover, the second component 210" may be mechanically, electrically, and/or fluidly coupled to the accessory support. These types of couplings of the first component 160" and the second component 210" are not particularly limited, and may be embodied in any form described herein, including wired or wireless connections.

The mechanical interface 146', the data interface 148', the power interface 150', and/or the fluid interface 152' may be arranged in a manner to provide coupling sets 156'''. The coupling sets 156''' of the first and second components 160", 210" may be advantageously positioned such that when the first component 160" and the second component 210" are mechanically coupled to each other, the medical accessory is electrically and/or fluidly coupled to the accessory support. In some embodiments, the medical accessory is electrically coupled (i.e., power and/or data) and/or fluidly coupled to the accessory support when the first and second components 160", 210" are mechanically coupled to one another in both the locked arrangement and the unlocked arrangement. In other embodiments, the medical accessory is electrically and/or fluidly coupled to the mounting apparatus/accessory support only when the first and second components 160", 210" are in the locked arrangement. Alternatively still, the electrical and fluid connections between the medical accessory and the mounting apparatus can be established even if the first and second components 160", 210" do not include a locking assembly.

Figure 15:
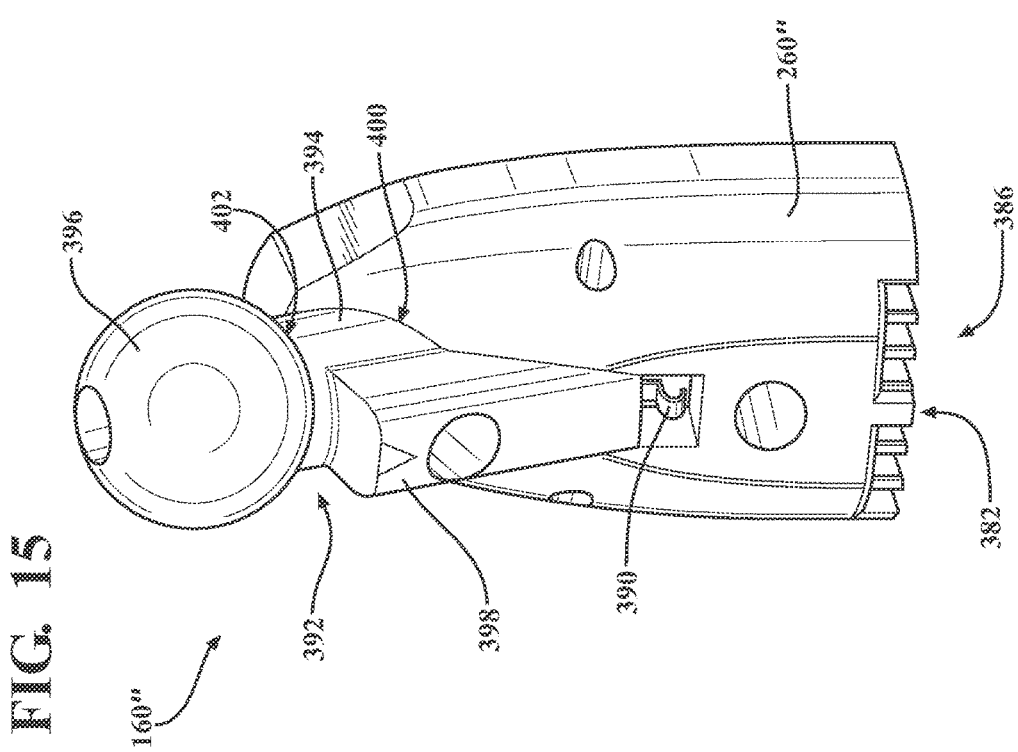
FIG. 15 is a perspective view of a first component of FIG. 14, illustrated with exemplary data, power and mechanical interfaces.
Figure 16:
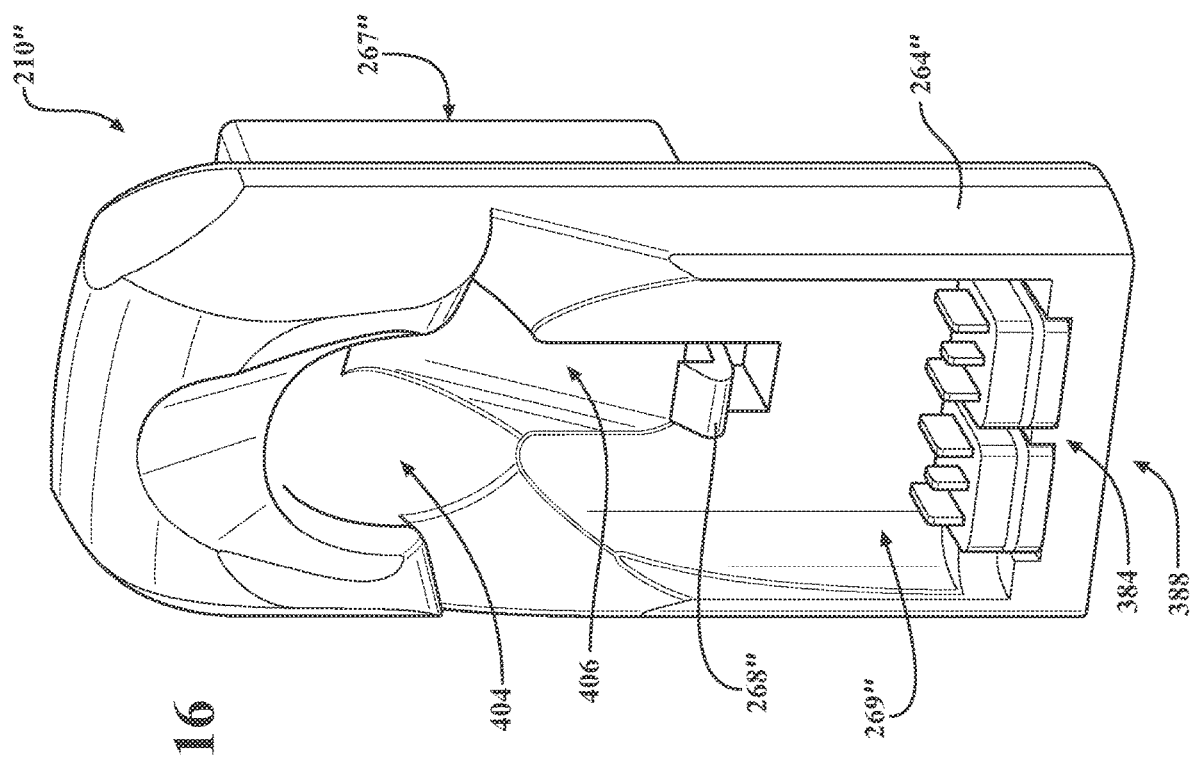
FIG. 16 is a perspective view of a second component according of FIG. 14, illustrated with exemplary data, power, and mechanical interfaces.

As shown in FIGS. 15 and 16, in some embodiments, it should be understood that the data interface 148' and the power interface 150' of the first and second components 160", 210" may be established with first and second electrical connectors 382, 384. Each electrical connector 382, 384, if present, is configured to electrically couple the first and second components 160", 210" to each other when the first and second components 160", 260" are mechanically coupled to one another. Moreover, when the first and second components 160", 210" are electrically coupled to the mounting apparatus and the medical accessory respectively, the first and second electrical terminals or connectors 382, 384 facilitate an electrical coupling between the medical accessory and the controller 149 and/or power distribution system 151 of the mounting apparatus 124, to enable the power interface and/or data interface described throughout.

The location of the first and second electrical connectors 382, 384 may be at any suitable location respectively on the first and second components 160", 210" to enable electrical coupling between the first component 160" and the second component 210". For example, with reference to FIGS. 14 and 15, the first and second electrical connectors 382, 384 may be located at a bottom end 386, 388 of the first and second components 160", 210" respectively. Of course, it is contemplated the electrical connectors 382, 384 may be located in positions other than the bottom end 386, 388.

In other embodiments, the first component may further comprise a third electrical connector and the second component may comprise a fourth electrical connector. When the third and fourth electrical connectors are present, the first and second components may be configured to electrically couple the first and second connectors, and the third and fourth connectors when the first component is coupled to the second component with the mechanical interface. Moreover, the third and fourth connectors may exchange only data whereas the first and second connectors may exchange only power. In other embodiments, both of the first and second connectors and the third and fourth connectors may exchange power and/or data. Of course, still other electrical connectors may be included in the coupling system.

As shown in FIGS. 15 and 16, the first connector 382 may comprise a female electrical connector 382 and the second electrical connector 384 may comprise a male electrical connector 384. Alternatively, the first connector may comprise a male electrical connector and the second electrical connector may comprise a female electrical connector.

In some embodiments, at least one of the first and second components 160", 210" may further comprise a proximity sensor 390 such as the proximity sensor described above for the deployment device. In some embodiments, the proximity sensor 390 may comprise a limit switch 390.

When the proximity sensor 390 is present, the first component 160", mounted on the accessory support, may be electrically coupled to the controller and/or power distribution system of the accessory support based on the proximity of the first component 160" relative to the second component 210". When the first component 160" is in proximity of the second component 210" the controller electrically couples the first component 160" to the controller and/or power distribution system of the accessory support based on the input signal received from the proximity sensor 390.

When the first component 160" is not in proximity of the second component 210", the controller does not electrically couple the first component 160" to the controller and/or power distribution system of the accessory support based on the input signal received from the proximity sensor 390.

When the proximity sensor 390 is present, the first electrical connector 382 of the first component 160", is not energized unless the first component 160" is in within a predetermined proximity of the second component 210". In this manner, the controller advantageously reduces the risk of electrical fires arising from arcing and electrical sparks, and reduces chance of accidental shock through inadvertent contact with the first electrical connector 382.

Referring again to FIG. 14, in some embodiments, the data interface 148' of the first and second components 160", 210" may function as the proximity sensor by facilitating communication from the medical accessory to the controller of the accessory support. For example, the controller may couple the first component to the power distribution system and/or energize the first electrical connector upon verifying the presence of a medical accessory via the data interface 148', such as through the 1-wire connection described above.

Figure 17:
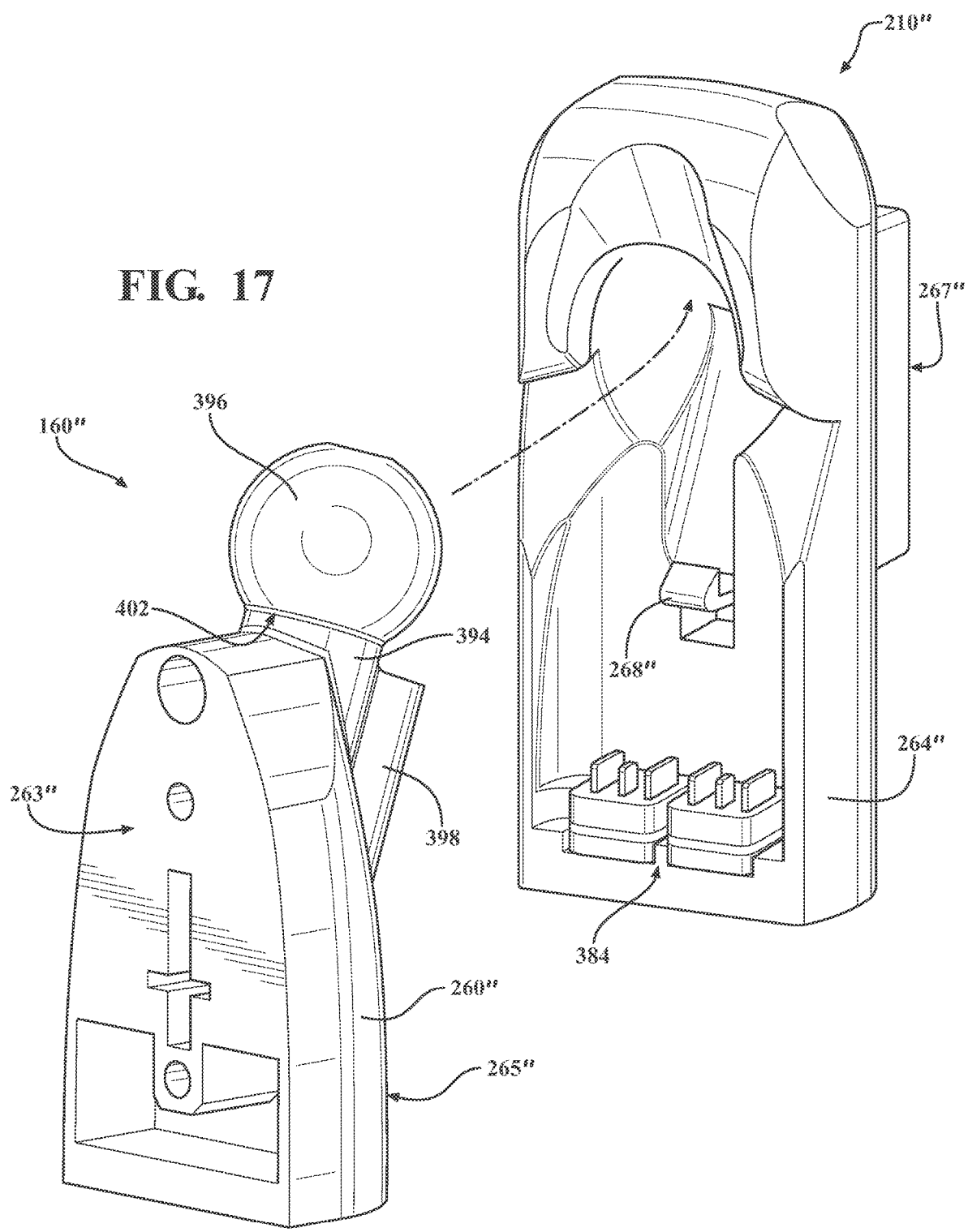
FIG. 17 is a perspective view of the first component of FIG. 15 and second component of FIG. 16 spaced from each other.

With reference to FIGS. 15 and 17-19, in one embodiment, the coupling system 212" comprises a first component 160". The first component comprises a first base 260" and a ball assembly 392 for engaging the second component 210". With reference to FIGS. 15 and 17, the first base 260" comprises a first mounting portion 263" and a first coupling portion 265". The first mounting portion 263" may be coupled to the accessory support such as the mounting apparatus described above. Alternatively, the first mounting portion 263" may be coupled to any medical accessory. It is further contemplated that the first mounting portion 263" may be coupled to the mounting devices described above.

With reference to FIG. 15, the first component 160" comprises proximity sensor 390 partially disposed within the first base 260".

As described above, the first component 160" comprises first electrical connector 382 which is the female electrical connector 382. The female electrical connector 382 is partially disposed in the first base 260". Of course, the female electrical connector 382 may be disposed elsewhere in the first component such as, for example, the ball assembly 392.

With reference to FIGS. 15 and 17, in the illustrated embodiment, the ball assembly 392 comprises an intermediate portion 394, a spherical portion 396, and a guide feature 398. The intermediate portion 394 is coupled to the first base 260" and extends from the first base 260" between a first end 400 adjacent the first base 260" and a second end 402 spaced from the first end 400. In the illustrated embodiment, the intermediate portion 394 is integral with the first base 260", however, it is contemplated the intermediate portion may not be integral with the first base 260". The spherical portion 396 is coupled to the second end 402 of the first base 260". The spherical portion 396 is configured for engagement with the second component 210". The guide feature 398 is coupled to the first base 160" and the intermediate portion 394. The guide feature 394 is geometrically configured to guide the first component 160" into proper engagement with the second component 210", including guiding electrical connectors 382, 384 into engagement with one another. In the illustrated embodiment, the guide feature 398 is integral with the first base 260" and the intermediate portion 394, however, it is contemplated the guide feature 398 may not be integral with the first base 260" and the intermediate portion 394.

Referring to FIGS. 16-19, the second component 210" comprises a second base 264". The second base 264" comprises a second mounting portion 267" and a second coupling portion 269" that is opposite the second mounting portion 267". The second mounting portion 267" may be mounted to a medical accessory, an accessory support such as the mounting apparatus as described above, or any mounting device described above.

As shown in FIG. 16, the second component 210" may comprise the male electrical connector 384 at least partially disposed in the second base 264' for electrically coupling the female electrical connector 382 of the first component 160". Of course, the male electrical connector 384 may be disposed elsewhere in the second component 210".

In some embodiments, the second base 264" may further define a spherical recess 404. As shown in FIGS. 16 and 17, the spherical recess 404 has a spherical configuration for receiving at least a portion of the spherical portion 396 of the first component 160".

In some embodiments, the second base 264" may define a guide feature groove 406 for guiding the first component 160" into the spherical recess 404 and receiving the guide feature 398 of the first component 160" such that the second component 210" is restricted from moving laterally with respect to the first component 160", whether the first and second components 160", 210" are in the locked or unlocked arrangement. Moreover, the guide feature groove 406 may restrict lateral movement of the second component 210" relative to the first component 160" when the first and second components do not comprise a lock assembly.

As shown in FIGS. 16 and 17, the second component 210" comprises a locking assembly 268" disposed within the second base 264". The locking assembly is configured to selectively engage the first base 260" of the first component 160" to restrict movement of the first component 160" with respect to the second component 210" in the locked arrangement. While one exemplary embodiment of the locking assembly 268" is shown in FIGS. 16 and 17, alternative configurations of the locking assembly 268" are contemplated.

When the locking assembly 268" engages the first base 260" such that movement of the second component 210" relative to the first component 160" is constrained, the coupling system 212" is in the locked arrangement. Thus, when the locking assembly 268" does not engage the first base 260" such that movement of the second component 210" relative to the first component 160" is constrained, the coupling system 212" is in the unlocked arrangement.

Figure 18:
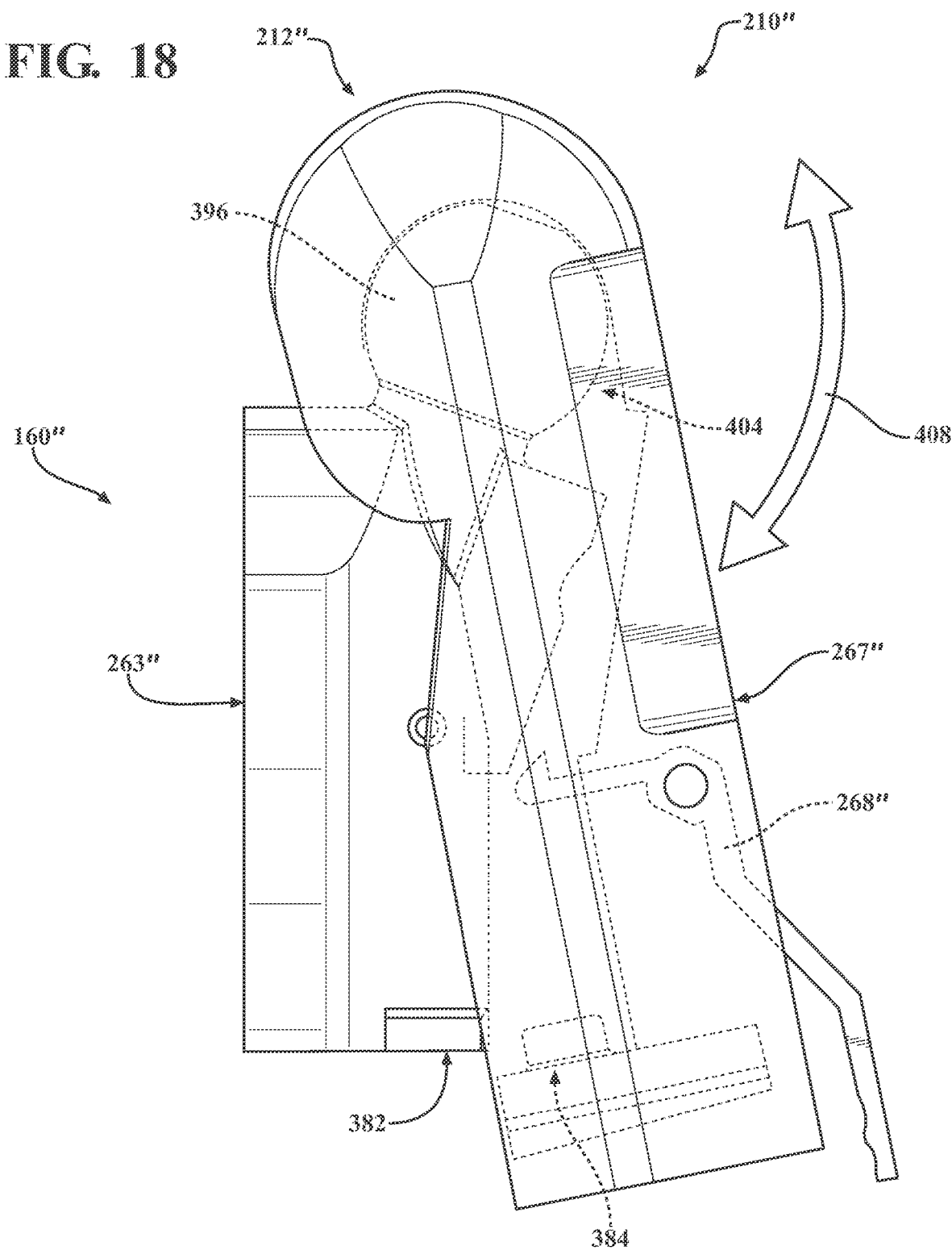
FIG. 18 is a perspective view of the first component of FIG. 15 and second component of FIG. 16 with the power and data interfaces spaced apart.
Figure 19:
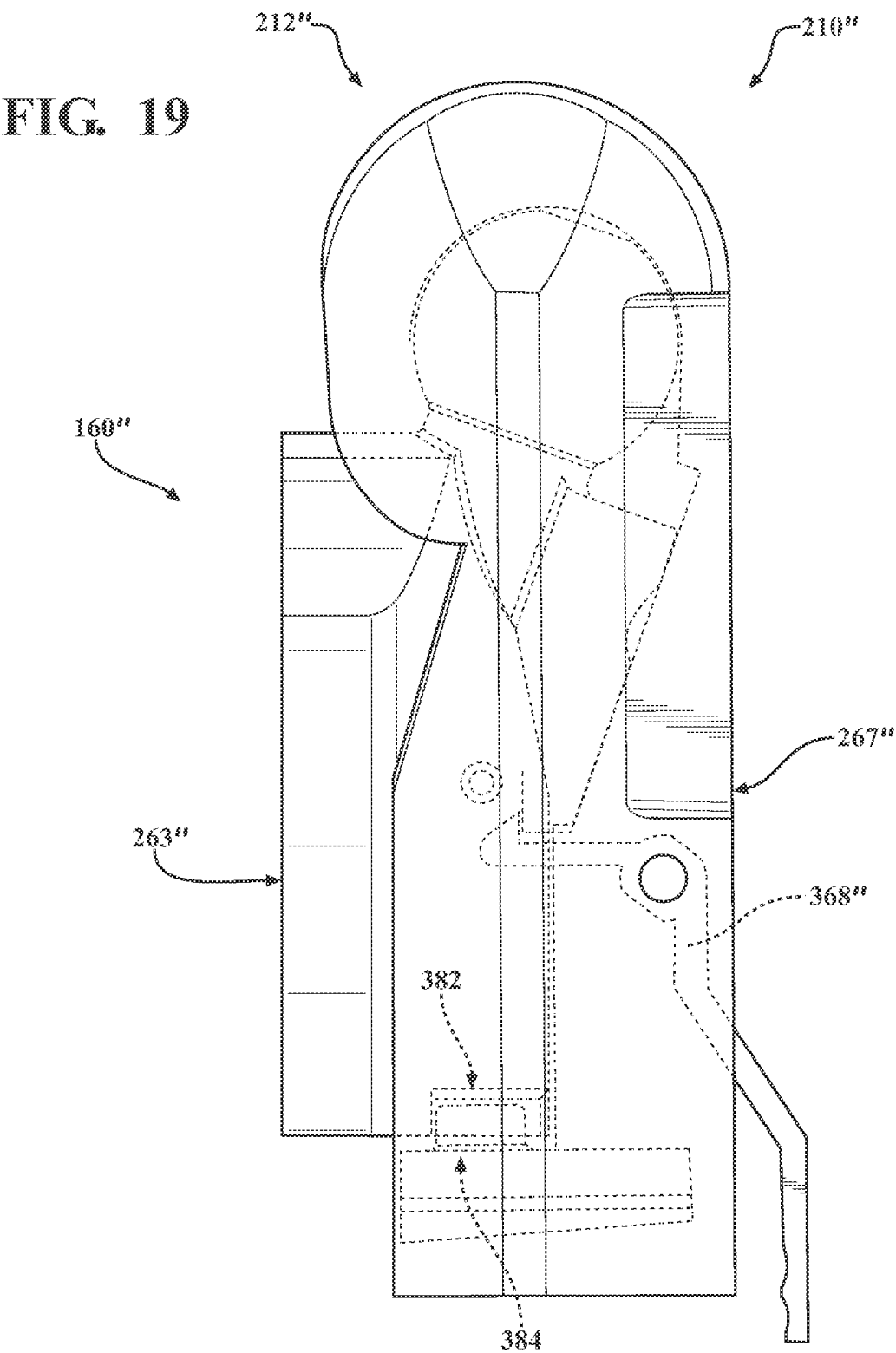
FIG. 19 is a perspective view of the first component of FIG. 15 and second component of FIG. 16 with the power and data interfaces coupled together.

The first and second components 160" and 210" may be coupled together such that the second component 210" may pivot relative to the first component 160" between a first position (see FIG. 18) and a second position (see FIG. 19). In the first position, the female and male electrical connectors 382, 384 of the first and second components 160", 210" may not be electrically coupled with each other. In the second position, the female and male electrical connectors 382, 384 of the first and second components 160", 210" are in communication (i.e., are electrically coupled) with each other.

With reference to FIG. 18, in the first position, the first component 160" and the second component 210" may be coupled together such that the ball assembly 392 of the first component 160" is received by the spherical recess 404, and the guide feature groove 406 of the second component 210". The spherical recess 404 and guide feature groove 406 of the second component 210" cooperate to constrain movement of the second component 210" relative to the first component 160". As shown in FIG. 18, the second component 210" is prevented from lateral movement relative to the first component 160" but can pivot as indicated by motion arrow 408 relative to the first component 160". In this manner, the first component 160" supports the weight of the second component 210" and any medical accessories mounted to the second component 210" while still allowing movement to establish the power and/or data interfaces.

It will be readily appreciated that when only the spherical portion 396 of the first component 160" engages the second component 210", the second component 210" may move laterally with respect to the first component 160" because the guide feature 398 does not engage the second component 210". Thus, the caregiver may partially support the second component 210" on the first component 160" while still retaining lateral movement of the second component 210" relative to the first component 160".

With continued reference to FIG. 18, when the coupling system 212" is in the first position, the male and female electrical connectors 384, 382 are not coupled to each other. In other words, in the first position the first and second components 160", 210" are not electrically coupled to each other despite the fact that the weight of the second component 210" is supported by the first component 160"

When the coupling system 212" is in the first position, the controller 149 may not electrically couple the first component 160" to the controller 149 and/or power distribution system 151 of the mounting apparatus. In other words, when the coupling system 212" is in the first position, electrical energy is prevented from flowing through the female electrical connector 382 of the first component 160".

In the illustrated embodiment, the coupling system 212" may be in the unlocked arrangement when in the first position. Of course, it is contemplated the coupling system 212" is in the locked arrangement when in the first position. In other embodiments, depending on the location of the electrical connectors in the first and second components, the first component may be in electrical communication in both the first position and the second position.

With reference to FIG. 19, in the second position, the female and male electrical connectors 382, 384 of the first and second components 160", 210" electrically couple each other. Thus, the coupling system 212" advantageously allows the caregiver to electrically couple the first and second components 160", 210" to each other quickly and efficiently by pivoting the second component 210" relative to the first component 160". In the second position, the second component 210" is supported by the first component 160" and electrically coupled to the first component 160". The caregiver may pivot the second component 210" between the first and second positions by urging the second component 210" in the upward or downward direction as indicated by motion arrow 408.

When the coupling system 212" is in the second position, the controller 149 electrically couples the first component 160" to the controller 149 and/or the power distribution system 151 based on the input signal from the proximity sensor. In other words, when the coupling system 212" is in the second position, electrical energy is allowed to flow through the female electrical connector 382 of the first component 160". Moreover, the controller 149 may be configured to control the power distribution system 151 to supply AC and/or DC power to the medical accessory when the first component electrically couples to the mounting apparatus. In such instances, the controller may selectively control the power distribution system to supply AC and/or DC power only when the first and second components are in proximity to each other.

In the illustrated embodiment, the coupling system 212" is in the locked arrangement when in the second position. Of course, it is contemplated the coupling system 212" is in the unlocked arrangement when in the second position.

It should be appreciated that the first component and the second component can be coupled to one another using other mechanisms, such as rotational locks or fasteners.

Figure 20:
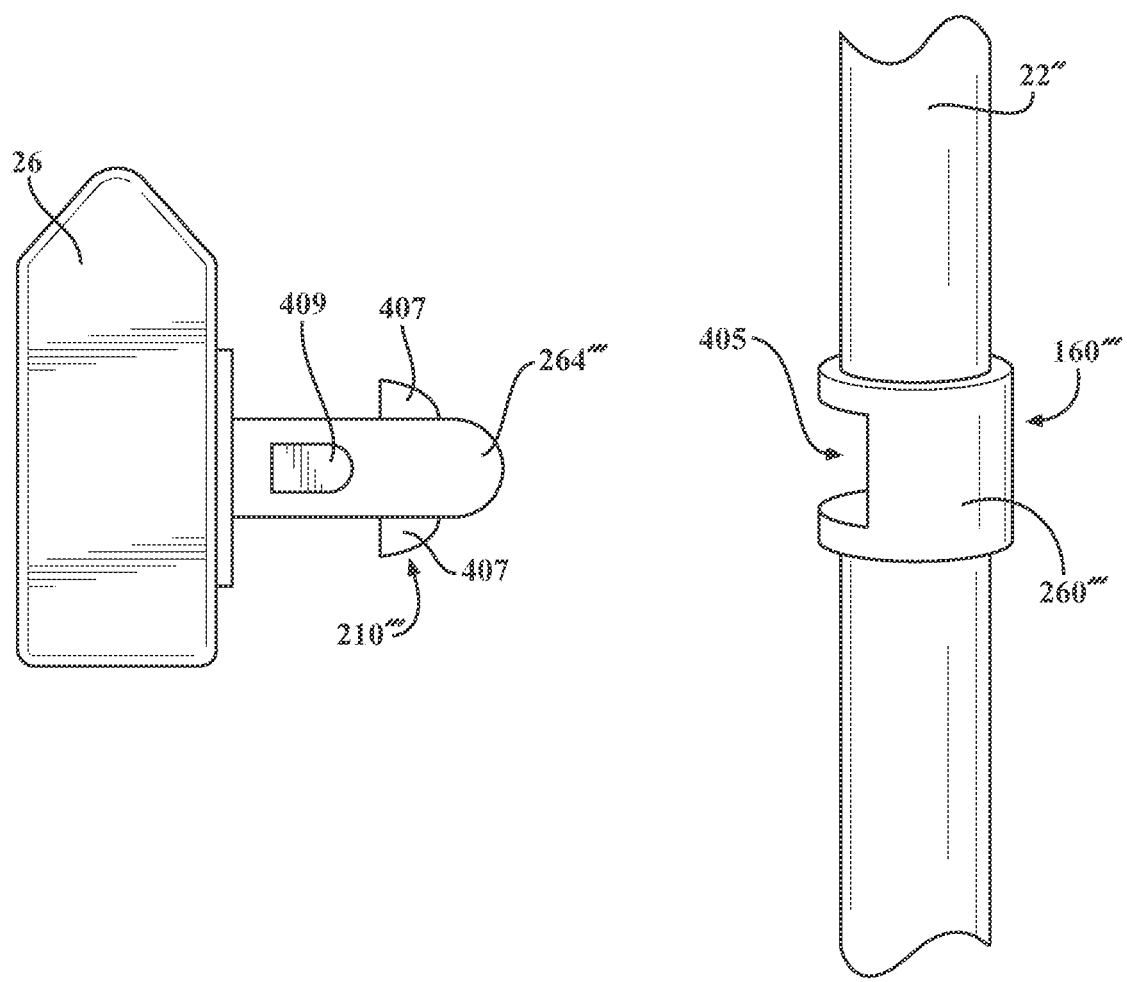
FIG. 20 is a front view of a first and second components of a coupling system according to a fourth embodiment, depicted schematically with coupling sets.

With reference to FIG. 20, in another embodiment, the coupling system comprises a first component 160'" and a second component 210'". In the illustrated embodiment, the first component 160'" is mounted to post 22" and the second component 210'" is mounted to the medical accessory 26. Of course, it is contemplated that the first component 160'" may be mounted to the medical accessory 26 and the second component 210" may be mounted to the post 22".

In the illustrated embodiment, the first component 160'" is integral with the post 22". However, first component 160'" may not be integral with the post 22'. The first component 160'" comprises a first base 260'". The first base 260'" defines a receiving chamber 405 for receiving the second component 210'".

The second component 210'" comprises a second base 264'". The second base 264'" comprises locking tabs 407 partially disposed within the second base 264'" and movable between an expanded position and a retracted position. When the locking tabs 407 are in the expanded position, the locking tabs 407 extend from the second base 264'". When the locking tabs 407 are in the retracted position, the locking tabs 407 are at least partially recessed within the second base 264'" such that the second component 210'" may be received in the receiving chamber 405 of the first component 160'".

The locking tabs 407 may be spring loaded such that the locking tabs 407 are biased into the expanded position. Moreover, the locking tabs 407 may be geometrically configured to move to the retracted position upon contact with the first base 260'". When the locking tabs are received by the receiving chamber 405, the locking tabs 407 are biased into the expanded position to couple the first and second components 160'", 210'" to each other.

The second base 264'" further comprises a push-button 409 to release the locking tabs 407 and allow the locking tabs 407 to transition between the expanded and retracted positions. When the caregiver engages the push-button 409, the locking tabs 407 may be permitted move to the retracted position. In this manner, the caregiver can quickly and efficiently decouple the second component 210'" from the first component 160'".

In some embodiments, the medical accessory may include a handle. The handle may be disposed towards the front of the accessory to allow the caregiver to favorably position the medical accessory adjacent the accessory support to facilitate engagement of any the mounting devices, or first or second components coupled to the medical accessory. Of course, the handle may be disposed in other locations on the medical accessory.

In some embodiments, it is contemplated that the medical accessories may include an integral screw clamp or other mounting device. In such embodiments, it may be useful to provide an adapter to retrofit the screw clamp or other mounting device such that the screw clamp or other mounting device may directly engage the first or second component. More specifically, the adapter may couple the first or second mounting portion of the first or second component. In this manner, the first or second component may be retrofitted to existing medical accessories in the healthcare facility.

In other embodiments, the medical accessory may be integrally formed with the first or second component. In other words, the first or second component coupled to the medical accessory may not have a discrete first or second mounting portion.

Figure 21A:
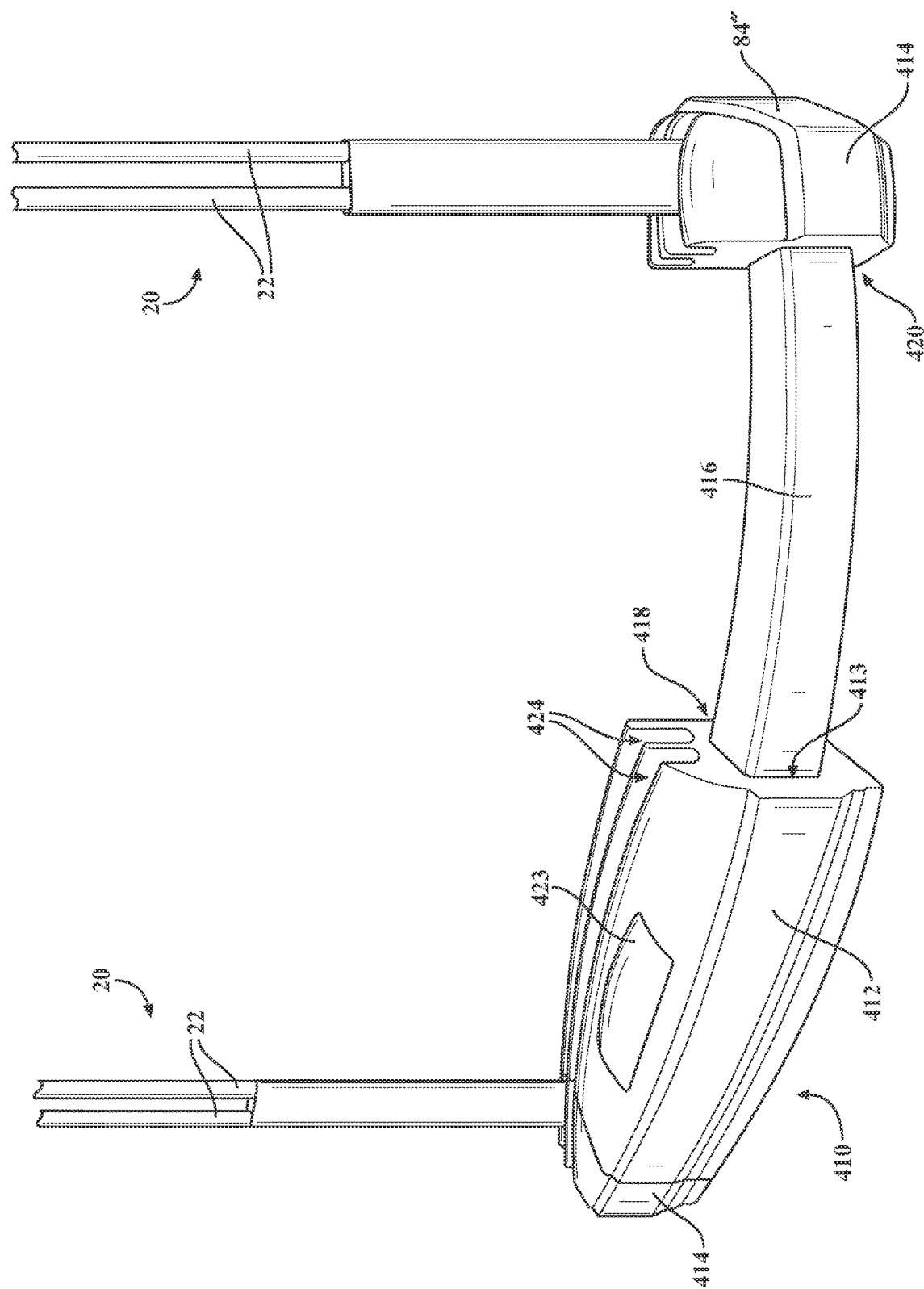
FIG. 21A is a perspective view of another embodiment of an arm assembly with one extendable arm in a patient-care position and the other extendable arm in a transport position.

With reference to FIG. 21A, in another embodiment, the arm assembly may comprise an extendable arm assembly 410. The extendable arm assembly 410 is configured to act as an accessory support for supporting medical accessories.

The extendable arm assembly 410 may comprise a housing 412. In certain embodiments, the footboard or the headboard of the patient support apparatus may serve as the housing 412 for the extendable arm assembly 410. Alternatively, the housing 412 may be used in addition to the footboard or headboard of the patient support apparatus, and may be mounted to any suitable location on the patient support apparatus, such as the base, the intermediate frame, or the deck.

With continued reference to FIG. 21A, the extendable arm assembly 410 comprises support members 414 and extendable arms 416. Each extendable arm 414 comprises a base end 418 and a support end 420 opposite the base end 418. The extendable arms 416 are slidably coupled to the housing 412 to move between a transport position (see FIG. 21B) and a patient-care position (see FIG. 21C).

Figure 21C:
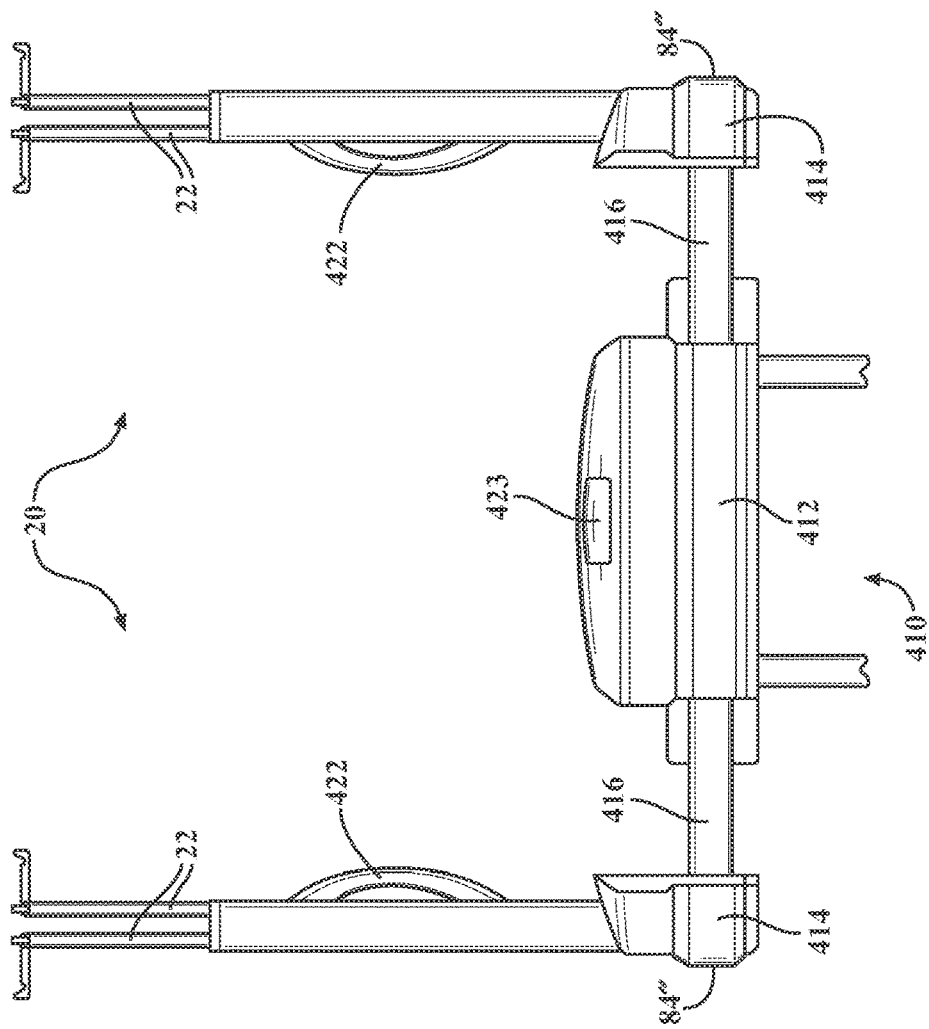
FIG. 21C is a front view of the arm assembly of FIG. 21A with both extendable arms shown in the patient-care position.
Figure 21B:
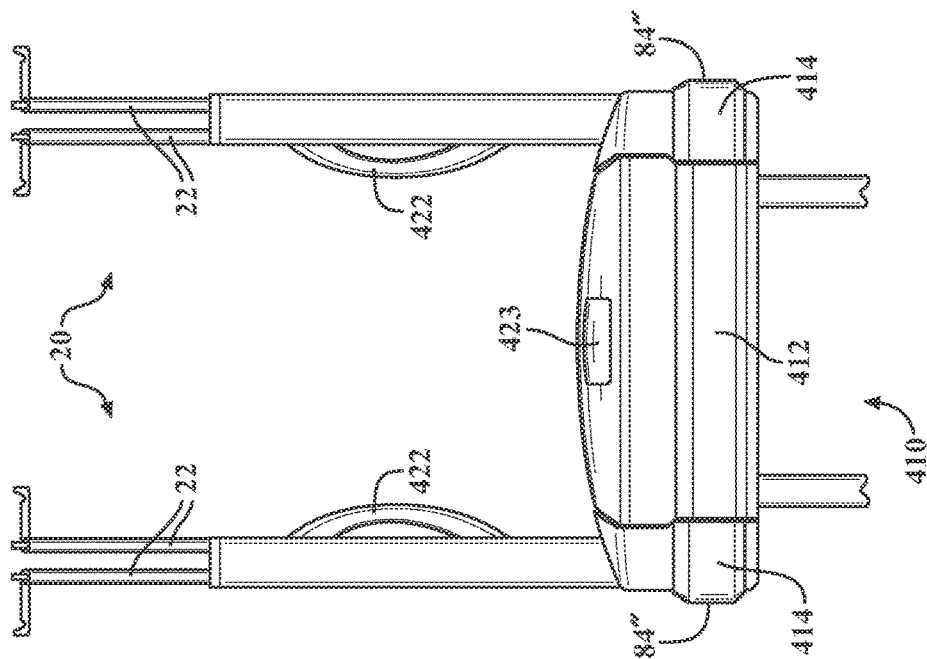
FIG. 21B is a front view of the arm assembly of FIG. 21A with both extendable arms shown in the transport position.

The base end 418 of each extendable arm 416 is disposed within the housing 410. The support member 414 may be mounted to the support end 420 of the extendable arm 416. Each support member 414 may further comprise a post mount 84". The post mount 84" is configured to engage the bottom of the accessory support 20, such as the bottom of the posts 22 to prevent movement of the posts 22 relative to the patient support apparatus. As shown in FIGS. 21B and 21C, and as described above, in some instances the accessory support 20 may comprise handles 422 to allow the caregiver to move the extendable arms 416 between the patient-care position and the transport position.

The housing 412 comprises an arm channel 413 on each side of the housing 412 to accommodate at least a portion of the extendable arms 416. In the illustrated embodiment, both the arm channels 413 and the extendable arms 416 have an arcuate shape. As such, as each extendable arm 416 moves from the transport position to the patient-care position, or vice-versa, the support end 420, and the accessory support 20, move along a curved path relative to the housing 412, and the patient support apparatus. Similarly, the base end 418 moves along a curved path defined by the arm channel 413 in the housing 412 as the extendable arm 416 moves between the patient-care position and the transport position, and vice versa.

Because the extendable arms 416 are retracted to within the housing 412 when the extendable arm assembly 410 is in the transport position, the majority of the length of the extendable arm 416 may be concealed by the housing 412. This concealing may present a more aesthetic appearance. As shown in FIG. 21B, when the extendable arms 416 are in the transport position, the extendable arms 416 are received by the housing 412 such that they are disposed within the housing 412 and the support members 414 abut the housing 412. As shown in FIG. 21C, when the extendable arms 416 are in the extended position, the extendable arms 416 project laterally outward from the housing 412 such that the support members 414 do not abut the housing 412.

In the patient-care position (FIG. 21C), at least one of the extendable arms 416 extend transversely to the patient support apparatus. Because of the arcuate shape, the extendable arms 416 also extend longitudinally toward the foot end of the patient support apparatus. In this position, the accessory supports 20 are spaced apart from the patient support apparatus and, hence, medical accessories coupled thereto are spaced away from a patient's head.

It is contemplated that the extendable arm assembly 410 may comprise a locking device configured to lock the extendable arms 416 in the patient-care position, the transport position, or any number of intermediate positions.

It is further contemplated that the extendable arm assembly 410 comprises an actuator configured to actuate the extendable arms 416 between the transport position and the patient-care position. When the actuator is present, the housing 412 may comprise a user input unit 423 configured to allow the caregiver to move the extendable arms 416 between the transport position and the patient-care position. By way of non-limiting example, the user input unit 423 may be a touchscreen. The user input unit 423 may also serve to control one or more driven wheels in certain embodiments, or control any other features of the patient support apparatus.

In some instances, the accessory support 20 may be pivotably coupled to the support member 414. In such an embodiment, the housing 412 may comprise receiving grooves 424 configured to receive the accessory support 20 such that the accessory support 20 may be stowed when the accessory supports 20 are not required for patient care. In other words, the accessory support 20 may be pivoted to lie substantially horizontal to rest within the receiving grooves 424 when not in use. The receiving grooves 424 may be dimensioned such that the accessory support 20 does not extend beyond either end. Furthermore, the receiving grooves 424 may be dimensioned such that when the accessory support 20 is stowed in the receiving grooves 424, the accessory support 20 does not extend beyond the top of the housing 412. Thus, compared to when the accessory supports 20 are in an upright position, the extendable arm assembly 410 has a reduced dimensional profile when the accessory supports 20 are stowed in the receiving grooves 424. In addition, as shown, the posts 22 may be telescopic such that they can be stowed in a length that can rest within the receiving grooves 424.

When the accessory support 20 is pivotably coupled to the support member 414, the support member 414 may further comprise a locking mechanism configured to lock the accessory support 20 relative to the support member 414 when the accessory support is in an upright position. The locking mechanism may also be configured to lock the accessory support 20 when it rests within the receiving grooves 424, or any number of intermediate positions.

Alternatively, the post mounts 84" may be releasably coupled to the support members 414 such that the post mounts 84" may be decoupled from the support members 414 and stowed in the receiving grooves 424 of the board member 412 when the accessory supports 20 are not required for patient care.

It should be appreciated that any post mount or frame mount described herein may include a clutch feature that allows rotation of the accessory support relative to the post mount. The level of force necessary to trigger the clutch feature may be adjusted by the use of a screw adjustment mechanism or other sufficient adjustment mechanism. The clutch may be disposed coaxially with the post mount/accessory support.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A medical accessory system for removably coupling to an accessory support having a power distribution system with a first component supported by and electrically coupled to the accessory support, the first component including a first coupling portion and a first electrical connector disposed in electrical communication with the power distribution system, said medical accessory system comprising:
   a medical accessory;
   a second component configured to support said medical accessory and be electrically coupled to said medical accessory, said second component including:
      a second coupling portion configured for being removably coupled to the first coupling portion of the first component, and
      a second electrical connector for electrically coupling said medical accessory to the first electrical connector;
   wherein said second coupling portion and the first coupling portion are configured to allow rotating motion of said second component relative to the first component in at least one degree of freedom between a first position and a second position, wherein said second component is supported by the first component in said first and second positions, and wherein, during use, said second component rotates relative to the first component in at least one degree of freedom between said first and second positions such that said second electrical connector is connected to the first electrical connector in said second position.

2. The medical accessory system as set forth in claim 1, wherein said second component comprises a locking assembly configured to place said second component and the first component in a locked arrangement.

3. The medical accessory system as set forth in claim 2, wherein said locking assembly is further configured to place said second component and the first component in an unlocked arrangement.

4. The medical accessory as set forth in claim 3, wherein said second component supports the first component in the locked arrangement and the unlocked arrangement.

5. The medical accessory system as set forth in claim 1, wherein said second component comprises an indicator device configured to indicate a coupling status between the accessory support and said medical accessory.

6. The medical accessory system as set forth in claim 1, wherein said second coupling portion comprises a spherical recess configured to engage a spherical portion of the first coupling portion.

7. The medical accessory system as set forth in claim 1, wherein said second electrical connector is not connected to the first electrical connector in said first position.

8. The medical accessory system as set forth in claim 1, wherein said medical accessory is selected from the group comprising an infusion pump, a fluid warmer, a monitor, a respirator, a physiological sensor, a ventilator, a cardiac monitor, a pulse oximeter, a non-invasive blood pressure measuring device, a digital thermometer, a liquid oxygen module, a defibrillator, a respiratory rate measuring device, and combinations thereof.

9. A medical accessory system for removably coupling to an accessory support having a DC power distribution system with a first component having a first mounting portion supported by the accessory support, a first coupling portion, and a first electrical connector disposed in electrical communication with the DC power distribution system, said medical accessory system comprising:
   a medical accessory free from an AC/DC converter and configured to receive DC power;
   a second component including:
      a second mounting portion supporting said medical accessory,
      a second coupling portion configured for being removably coupled to the first coupling portion, and
      a second electrical connector electrically coupled to said medical accessory;
   wherein said second coupling portion and the first coupling portion are configured to allow rotating motion of said second component relative to the first component in at least one degree of freedom between a first position and a second position, wherein said second component is supported by the first component in said first and second positions, and wherein, during use, said second component rotates relative to the first component in at least one degree of freedom between said first and second positions such that said second electrical connector is connected to the first electrical connector in said second position to enable the power distribution system of the accessory support to provide DC power to said medical accessory.

10. The medical accessory system as set forth in claim 9, wherein said second component comprises a locking assembly configured to place said second component and the first component in a locked arrangement.

11. The medical accessory system as set forth in claim 10, wherein said locking assembly is further configured to place said second component and the first component in an unlocked arrangement.

12. The medical accessory as set forth in claim 11, wherein said second component supports the first component in the locked arrangement and the unlocked arrangement.

13. The medical accessory system as set forth in claim 9, wherein said second component comprises an indicator device configured to indicate a coupling status between the accessory support and said medical accessory.

14. The medical accessory system as set forth in claim 9, wherein said second coupling portion comprises a spherical recess configured to engage a spherical portion of the first coupling portion.

15. The medical accessory system as set forth in claim 9, wherein said second electrical connector is not connected to the first electrical connector in said first position.

16. The medical accessory system as set forth in claim 9, wherein said medical accessory is selected from the group comprising an infusion pump, a fluid warmer, a monitor, a respirator, a physiological sensor, a ventilator, a cardiac monitor, a pulse oximeter, a non-invasive blood pressure measuring device, a digital thermometer, a liquid oxygen module, a defibrillator, a respiratory rate measuring device, and combinations thereof.

\* \* \* \* \*